United States Patent [19]

Shah et al.

[11] Patent Number: 5,705,333

[45] Date of Patent: Jan. 6, 1998

[54] PEPTIDE-BASED NUCLEIC ACID MIMICS (PENAMS)

[75] Inventors: Vibhakar J. Shah; George L. Kenyon, both of San Francisco; Irwin D. Kuntz, Greenbrae, all of Calif.

[73] Assignee: The Regents of The University of California, Oakland, Calif.

[21] Appl. No.: 286,875

[22] Filed: Aug. 5, 1994

[51] Int. Cl.$^6$ .......................... C12Q 1/68; C07H 21/00; C07K 7/00; C07K 1/00

[52] U.S. Cl. .................. 435/6; 435/375; 435/377; 536/23.1; 536/24.3; 536/24.31; 536/24.32; 536/24.5; 530/300; 530/333; 436/86; 436/94

[58] Field of Search ..................... 514/44; 536/24.3, 536/24.31, 24.32, 24.5, 23.1; 530/300, 333; 435/6, 375, 377; 930/10, 20, 21; 436/86, 94

[56] References Cited

U.S. PATENT DOCUMENTS 5,217,866 6/1993 Summerton et al. ................... 435/6

FOREIGN PATENT DOCUMENTS 8605518 9/1986 WIPO ........................ C12Q 1/68

OTHER PUBLICATIONS

R. McGraw et al., BioTechniques, 8(6) ('90) 674–678.
H. Kang et al., Biopolymers, 32 ('92) 1351–63.
F. Flam, Science 262 (Dec. 10, 1993) 1647–9.
P. Wittung et al., JACS 117(41) (Oct. 18, 1995) 10168–73.
B. Hyrup et al., JACS 116 ('94) 7964–70.
E. Uhlmann et al., Chemical Reviews 90(4) (Jun. 1990) 543–84.
J. Milligan et al., J. Med. Chem. 36(14) (Jul. 9, 1993) 1923–37.
C. Stein et al., Science 261 (Aug. 20, 1993) 1004–12.
J. Sambrook et al., "Molecular Cloning, A Laboratory Manual" (Cold Spring Harbor Lab. Press) (1989) pp. 11.2–11.9, 11.45–11.49, 11.52–11.61.
P. Garner et al., Tetrahed. Lett 34 (8) ('93) 1275–8.
J. Goodchild, Bioconj. Chem. 1(3) (May/Jun.–90) 165–87.
P. Nielsen et al., Science, (Dec. 6, 1991) 1497–1500.
L. Kosynkina et al., Tetrahed. Lett 35(29) (Jul. 18, 1994) 5173–6.
Buttrey, et al., "Synthetic Analogues of Polynucleotides–XII(The Resolution of DL–β–(Thymin-1-YL)Alanine and Polymerisation of the β–(Thymin-1-YL)Alanines", Tetrahedron (1975), 31: 73–75.
Cheikh, et al., "Polymerization of Amino Acids Containing Nucleotide Bases", J. Mol. Evol. (1990), 30: 315–321.
Doel, et al., "An Approach to the Synthesis of Peptide Analogues of Oligonucleotides (Nucleopeptides)" Tetrahedron Letters (1969), 27: 2285–2288.
Doel, et al., "The Synthesis of Peptides Containing Purine and Pyrimidine Derivatives of DL–Alanine", Tetrahedron (1974), 30: 2755–2759.

Draminski, et al., "Polypeptides Containing Adenine and Uracil Residues", Makromol. Chem. (1978), 179:2195–2200.
Egholm, et al., "Recognition of Guanine and Adenine in DNA by Cytosine and Thymine Containig Peptide Nucleic Acids (PNA)", J. Am. Chem. Soc. (1992), 114: 9677–9678.
Egholm, et al., "Peptide Nucleic Acids containing Adenine or Guanine recognize Thymine and Cytosine in Complementary DNA Sequences", J. Chem. Soc. Chem. Commun. (1993), 800–801.
Huang, et al., "Acyclic Nucleic Acid Analogues: Synthesis and Oligomerizatin of γ,4–Diamino–2–oxo–1(2H)–pyrimidinepentanoic Acid and δ,4–Diamino–2–oxo–1(2H)–pyrimidinehexanoic Acid", J. Org. Chem. (1991), 56: 6007–6018.
Hyrup, et al., "Modification of the Binding Affinity of Peptide Nucleic Acids (PNA). PNA with Extended Backbones consisting of 2–Aminoethyl–β–alanine or 3–Aminopropylglycine Units", J. Chem. Soc. Chem. Commun. (1993), 518–519.
Koning, et al., "Unconventional Nucleotide Analogues. VI(Syntheis of Purinyl–and Pyramidyl–Peptides)", Recueil (1971), 91: 1069–1080.
Kropachev, et al., "Synthesis of Model Biopolymers by Reactions in Polyphosphite Chains", Makromol. Chem. Suppl. (1985), 9: 47–51.
Lidak, et al., "Peptides of Aminonucleic Acids Polypeptides of β–(1–Pyrimidyl)–α–Amino Acids". Institute of Organic Synthesis, Academy of Sciences of the Latvian SSR. Translated from Khimiya Geterotsiklicheskikh Soedinenii, No. 11, pp. 1560–1563, Nov., 1975. Original article was submitted on Jun. 5, 1974.
Lidak, et al., "Synthesis of Oligopeptides Containing DL–β–(1–Uracilyl)–and DL–β–(9–Adeninyl)–α–Alanine and Lysine Residues and Study of their Reaction with DNA". Institute of Organic Synthesis, Academy of Sciences of the Latvian SSR. Translated from Khimiya Geterotsiklicheskikh Soedinenii, No. 3, pp. 402–405, Mar., 1983. Original article was submitted on Jun. 16, 1982.
Nollet, et al., "Unconventional Nucleotide Analogues–I($N_9$–Purinyl α–Amino Acids)", Tetrahedron (1969), 25: 5971–5981.

(List continued on next page.)

Primary Examiner—Charles C.P. Rories
Attorney, Agent, or Firm—Morrison & Foerster

[57] ABSTRACT

The present invention provides novel nucleic acid mimics (termed "PENAMs") comprising a peptidic backbone and nucleotidic sidechains; the sidechains being oriented in such a way that the PENAM is homomorphous to target nucleic acids with which it can effectively hydrogen bond. Homomorphism is achieved by the incorporation of unusual sterochemical centers, including D-chiral centers and quasi-chiral centers, into the peptidic backbone. The PENAMs are useful for targeting nucleic acid sequences in order to modulate their activity in an "antisense" manner. Targeting can also be used to detect, isolate or modify target nucleic acids.

24 Claims, 14 Drawing Sheets

OTHER PUBLICATIONS

Nollet, et al., "Unconventional Nucleotide Analogues–II-(Synthesis of the Adenyl Analogue of Willardine)", *Tetrahedron* (1969), 25: 5983–5987.

Nollet, et al., "Unconventional Nucleotide Analogues–III($4-N_1$–Pyrimidyl) 2–Aminobutyric Acids)", *Tetrahedron* (1968), 25: 5989–5994.

Olsuf'eva, et al., "Nucleo Amino Acids and Nucleopeptides. IV. Synthesis of Oligonucleopeptides Containing Residues of $\beta$–(Uracilyl–$N^1$)–$\alpha$–Alanine and $\beta$–(Adeninyl–$N^9$)–$\alpha$–Alanine". M.V. Lomonosov Moscow State University. Translated from Zhurnal Obshchei Khimii, vol. 49, No. 5, pp. 1147–1151, May, 1979. Original article was submitted on Jul. 24, 1978.

Olsuf'eva, et al., "Nucleo Amino Acids and Nucleopeptides. V. Interaction of Side Chains in Oligonucleotides". M.V. Lomonosov Moscow State University. Translated from Zhurnal Obshchei Khimii, vol. 49, No. 5, pp. 1151–1156, May, 1979. Original article was submitted on Jul. 24, 1978.

Pitha, et al., "Poly (I–Vinyluracil): The Preparation and Interactions with Adenosine Derivatives", *Biochim. Biophy Acta* (1970), 204: 39–48.

Pitha, et al., "Preparation and Properties of Poly–9–vinyladenine", *Biopolymers* (1970), 9:965–977.

Poritere, et al., "Synthesis of Optically Active 9–Purinyl–$\alpha$–Amino Acids". Institute of Organic Synthesis, Academy of Sciences of the Latvian SSR. Translated from Khimiya Geterotsiklicheskikh Soedinenii, No. 12, pp. 1690–1695, Dec. 1982. Original article was submitted on Dec. 7, 1981.

Raukas, et al., "Interaction of Oligopeptides Containing Residues of DL–$\beta$–(Uracilyl–1)–, DL–$\beta$–(Adeninyl–9)–$\alpha$–Alanines and Lysines with Poly(A) and DNA", *Studia Biophysica* (1982), 89: 187–195.

Semiletov, et al., "Nucleo Amino Acids and Nucleopeptides. VII. Synthesis of Stereoregular Nucleotripeptides of a Mixed Type and Study of their Interaction with Natural Polynucleotides". M.V. Lomonosov Moscow State University. Translated from Zhurnal Obshchei Khimii, vol. 51, No. 1, pp. 230–238, Jan., 1981. Original article was submitted on Jun. 24, 1980.

Shvachkin, et al., "Solid–Phase Synthesis of an Oligonucleopeptide Containing an Unvaried Block of 3–(1–Uracilyl)Alanine Residues". M.V. Lomonosov Moscow State University. Translated from Zhurnal Obshchei Khimii, vol. 45, No. 1, p. 247, Jan., 1975. Original article was submitted on Mar. 20, 1974.

Shvachkin, et al., "Solid–Phase Synthesis of an Oligonucleopeptide Containing a Monotonic Vlock of Adenylyl–$N^9$–$\alpha$–Alanine Residues". M.V. Lomonosov Moscow State University. Translated from Zhurnal Obshchei Khimii, vol. 45, No. 9, p. 2110, Sep., 1975. Original article was submitted on Dec. 27, 1974.

Shvachkin, et al., "Synthesis of Homonucleopeptides by the Polycondensation of Activated Esters of Nucleoamino Acids". M.V. Lomonosov Moscow State University. Translated from Zhurnal Obshchei Khimii, vol. 46, No. 1, pp. 199–200, Jan., 1976. Original article was submitted on May 4, 1975.

Shvachkin, et al., "Preparation of Stereoregular Homonucleopeptides from Activated Derivatives of the Optical Isomers of Uracilyn–$N^1$–Alanine". M.V. Lomonosov Moscow State University. Translated from Zhurnal Obshchei Khimii, vol. 46, No. 11, pp. 2634–2635, Nov., 1976. Original article was submitted on Jan. 23, 1976.

Shvachkin, et al., "Total Synthesis of Willardine Peptides Isolated from *Fagus silvatica*". M.V. Lomonosov Moscow State University. Translated from Zhurnal Obshchei Khimii, vol. 47, No. 11, pp. 2631–2632, Nov., 1977. Original article was submitted on Jan. 10, 1977.

Shvachkin, et al., "Nucleo Amino Acids and Nucleopeptides. II. Synthesis of Protected and Activated Derivatives of Nucleo Amino Acids". M.V. Lomonosov Moscow State University. Translated from Zhurnal Obshchei Khimii, vol. 49, No. 5, pp. 1133–1139, May, 1979. Original article was submitted on Jun. 13, 1978.

Shvachkin, et al., "Nucleo Amino Acids and Nucleopeptides. III. Synthesis of Nucleodipeptides Containing Residues of $\beta$–(Uracilyl–$N^1$)–$\alpha$–Alanine and $\beta$–(Adeninyl–$N^9$)–$\alpha$–Alanine". M.V. Lomonosov Moscow State University. Translated from Zhurnal Obshchei Khimii, vol. 49, No. 5, pp. 1139–1146, May, 1979. Original article was submitted on Jul. 12, 1978.

Stirchak, et al., "Uncharged Stereoregular Nucleic Acid Analogues: 1. Synthesis of a Cytosine–Containing Oligomer with Carbamate Internucleoside Linkages", *J. Org. Chem.* (1987), 52: 4202–4206.

Stirchak, et al., "Uncharged stereoregular nucleic acid analogs: 2. Morpholino nucleoside oligomers with carbamate internucleoside linkages", *Nucleic Acids Research* (1989), 17:6131–6141.

Takemoto, et al., "Nucleic Acids Analogs: Their Specific Interaction and Applicability", *Y. Polym. Mat. Sci. Eng.* (1988) 58: 250–253.

Weller, et al., "Molecular Modeling of Acyclic Polyamide Oligonucleotide Analogues", *J. Org. Chem.* (1991), 56: 6000–6006.

Miller, P.S. and Ts'o, P. O. P. "Oligonucleotide Inhibitors of Gene Expression in Living Cells: New Opportunities in Drug Design" Ann. Rep. Med. Chem. 23:295–304, 1988.

Matteucci, M. D. and Bischofberger, N. "Sequence–defined Oligonucleotides as Potential Therapeutics". Ann. Rep. Med. Chem. 26:287–296, 1991.

Cohen, J. S. Oligodeoxynucleotides: Antisense Inhibitors of Gene Expression. Topics in Molecular and Structural Biology. 1–255, 1989, CRC Press, Boca Raton, Florida. A Title Page and Table of Contents is enclosed herewith.

Ghosh, M. K. and Cohen, J. S. "Oligodeoxynucleotides as antisense inhibitors of gene expression". Prog. in Nucl. Acid Res. and Mol. Biol. 42 (79):79–126, 1992.

Helene, C. and Toulmé, J.–J. "Specific Regulation of Gene Expression by Antisense, Sense and Antigene Nucleic Acids". Biochim. Biophys. Acta. 1049:99–125, 1990.

Stein, C. A. and Cohen, J. S. "Oligodeoxynucleotides as Inhibitors of Gene Expression: A Review". Cancer Res. 48:2659, 1988.

Stein, C. A. and Cheng, Y. "Antisense Oligonucleotides as Therapeutic Agents—Is the Bullet Really Magic?". Science. 261:1004–1011, 1993.

Uhlmann, E. and Peyman, A. "Antisense Oligonucleotides: A New Therapeutic Principle". Chem. Rev. 90(4):544–579, 1990.

Nielsen, P. E., Egholm, M., and Buchardt, O. "Peptide Nucleic Acid (Pna)—A Dna Mimic With A Peptide Backbone". Bioconjugate Chemistry. 5(1):3–7, 1994.

Connolly, B. A. "Synthetic oligodeoxynucleotides containing modified bases". Methods Enzymol. 211(36):36–53, 1992.

Miller, P.S., et al. "Recognition Of A Guanine Cytosine Base Pair By 8–Oxoadenine". Biochemistry. 31(29):6788–6793, 1992.

Sanghvi, Y. S., et al. "Antisense Oligodeoxynucleotides—Synthesis, Biophysical and Biological Evaluation of Oligodeoxynucleotides Containing Modified Pyrimidines". Nucleic Acids Research. 21(14):3197–3203, 1993.

Grein, T., et al. "3–Deaza–And 7–Deazapurines—Duplex Stability of Oligonucleotides Containing Modified Adenine Or Guanine Bases". Bioorganic & Medicinal Chemistry Letters. 4(8):971–976, 1994.

Lin, P. K. and Brown, D. M. "Oligonucleotides containing degenerate bases. Synthesis and uses". Methods Mol Biol. 26(187):187–206, 1994.

Spatola, A. F. "Peptide Backbone Modifications: A Structure–Activity Analysis of Peptides containing Amide Bond Surrogates." Chemistry and Biochemistry of Amino Acids Peptides and proteins. Weinstein ed. 1983 Marccel Dekker Inc. New York.

Gante, J. "Azapeptides". Synthesis.:405–413, 1989.

Nielsen, P.E., et al. "Peptide nucleic acids (PNAs): potential antisense and anti-gene agents". Anticancer Drug Des. 8(1): 53–63, 1993.

Garner, P. and Yoo, J.U. "Peptide–Based Nucleic Acid Surrogates Incorporating Ser[CH$_2$B]–Gly Subunits". Tetrahedron Letters 34(8):1275–1278, 1993.

Lenzi, A., et al. "Synthesis of N–Boc–$\alpha$–Amino Acids with Nucelobase Residues as Building Blocks for the Preparation of Chiral PNA (Peptide Nucleic Acids)". Tetrahedron Letters 36(10):1713–1716, 1995.

Lenzi, A., et al. "Solid Phase of a Self Complementary (Antiparralel) Chiral Peptidic Nucleic Acids Strand". Tetrahedron Letters 36(10):1717–1718, 1995.

Dueholm, K. L., et al. "Peptic Nucleic Acid (PNA) with a Chiral Backbone Based on Alanine". Bioorganic and Medicinal Letters 4(8):1077–1080, 1994.

Zuckerman, R. N. et al. "Efficient Method for the Preparation of Peptoids [Oligo(N–Substituted Glycines)] by Submonomer Solid–Phase Synthesis" J. Am. Chem. Soc. 114:10646–10647, 1992.

Ecker, D. J. et al., "Rational Screening of Oligonucleotide Combinatorial Libraries for Drug Discovery" Nucl. Acids Res. 21(8):1853–1856, 1993.

Nielsen, P. E. et al., "Sequence–Specific Transcription Arrest by Peptide Nucleic Acid Bound to the DNA Template Strand" Gene 149:139–145; 1994.

Takemoto, K. et al, "Synthetic Nucleic Acids Analogs, Preparation and Interaction" Adv. Polymer Sci. 41:1–51, 1981.

Egholm, M. et al., "Peptide Nucleic Acids (PNA). Oligonucleotide Analogues With an Achiral Peptide Backbone" J. Am. Chem. Soc. 114:1895–1897, 1992.

Nielsen, P. E. et al., "Sequence–Selective Recognition of DNA by Strand Displacement With a Thymine–Substituted Polyamide" Science 254:1497–1500, 1991.

Hanvey, J. C. et al., "Antisense and Antigene Properties of Peptide Nucleic Acids" Science 258:1481–1485, 1992.

V. Shah et al. Bioorg. Chem. 24: 201–6 ('96).

DNA/RNA/ONT
B = A, T, G, C, U
R = H, OH; R' = R'' = PROTECTIVE GROUPS

PEPTIDE NUCLEIC ACID MIMIC (PENAM)
E = C, N; X = O, S
B = A, T, G, C, U, & Pu/Py ANALOGS
S1, S2, S3, W, Y = SPACER GROUPS
Z, R = PROTECTIVE GROUPS (D/L)-PEPTIDE NUCLEIC ACID MIMIC (PENAM)
Nu = A, T, G, C, U, Pu/Py ANALOGS
Z, R = PROTECTIVE GROUPS; p = e.g. 2 - 3...; n = e.g. 2 - 8...

(D/L)-NUCLEIC AMINOACID (NuAA)   (D/L)-HALO AMINOACID (XAA)
Nu = A, T, G, C, U, Pu/Py ANALOGS   X = Br, Cl, I, p = e.g. 2 - 3...
p = e.g. 2 - 3...

(D/L)-ω-HYDROXY AMINOACID         (D/L)-HOMOGLUTAMIC ACID
P = e.g. 1 - 3...

(D/L)-α-AMINO-ω-LACTONE
p = e.g. 1, 2, 3...

(D/L)-ASPARTIC ACID (D/L)-GLUTAMIC ACID           (D/L)-METHIONINE

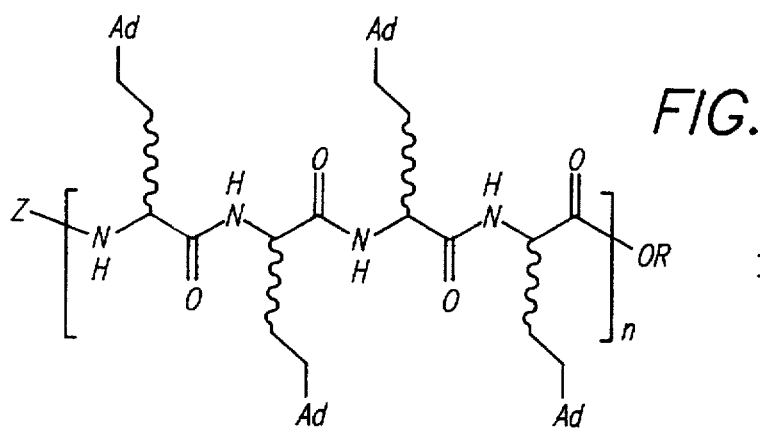
FIG. 4B
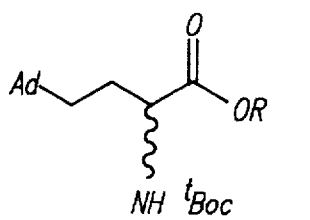
(D/L)-PEPTIDE NUCLEIC ACID MIMIC (PENAM)
Ad = ADENINE
Z, R = PROTECTIVE GROUPS; n = e.g. 2 - 8...
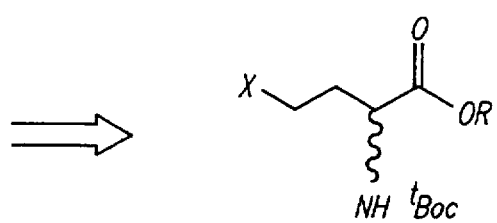
(D/L)-NUCLEICAMINO ACID (AdhAla)
Ad = ADENINE
(D/L)-HALOAMINO ACID (XAA)
X = Br, I, Cl
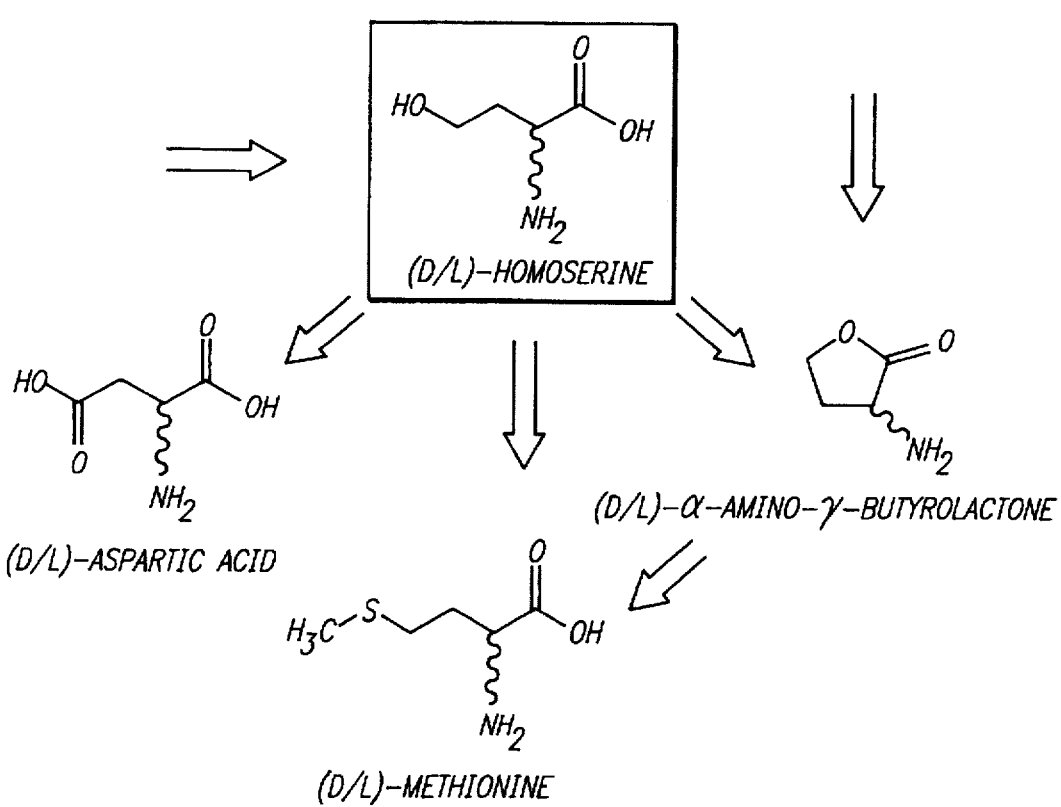
(D/L)-HOMOSERINE
(D/L)-ASPARTIC ACID
(D/L)-α-AMINO-γ-BUTYROLACTONE
(D/L)-METHIONINE

PEPTIDE-BASED NUCLEIC ACID MIMICS (PENAMS)

This invention was funded in part by National Institutes of Health Grant No. GM39552. The United States Government may have certain rights in the invention.

FIELD OF THE INVENTION

The invention generally relates to compounds that are capable of binding to nucleic acids in a sequence-specific manner. More specifically, the invention provides novel chimeric molecules having a backbone that resembles a polypeptide but side chains that resemble the base portions of nucleic acids. The invention also relates to the construction of such chimeric molecules; and to their use in targeting complementary nucleic acids.

BACKGROUND

Nucleic acids can be targeted by virtue of the ability of "antisense" nucleotidic bases to engage in hydrogen bonding with complementary bases of a target nucleic acid, thereby modulating expression of the target. The use of sequence-specific recognition of pathogenic genes to regulate or inhibit their expression in an antisense manner, using short synthetic complementary oligo(deoxy)nucleotides ("ODNs") and their analogs has been an attractive strategy for rational drug design [1, 2]. [Throughout this document, arabic numbers in square brackets refer to one or more references cited in the list of References below.]

A simple illustration of such a technique would be the administration of a DNA oligomer complementary to a target mRNA that encodes a protein necessary for the progression of infection of an agent such as a virus. In such a case, the administered DNA might bind to the target mRNA transcript, resulting in translation arrest, thereby blocking the synthesis of a protein critical to infection. Hybridization to a nascent mRNA may lead to premature termination of transcription. It is also possible to target double-stranded DNA using an appropriate oligomer capable of engaging in the formation of a triple helix via insertion of the oligomer into the major groove of the double-helical DNA.

General approaches to the construction and modification of oligomers useful in antisense therapy have been described in a number of reviews, see, e.g., Miller & Ts'o [1], Matteucci & Bischofberger [2], Cohen & Ghosh [3, 4], Helene & Toulme [5], Stein [6, 7], Uhlmann & Peyman [8], and the papers reviewed therein. In addition, a publicly available bibliography of citations relating to antisense oligonucleotides is maintained by Dr. Leo Lee at the Frederick Cancer Research Facility in Frederick, Md. which references are hereby incorporated herein.

Although there have been some promising results from the use of antisense ODNs in cell culture, suggesting the potential of this methodology for inhibiting gene expression, ODNs are subject to two significant limitations: (i) relatively poor transport across cellular membranes and (ii) sensitivity to cellular nucleases [4].

There have been a number of attempts to circumvent these problems by modifying the oligomers. For example, since nucleases are known to attack the phosphodiester linkage, a number of modified oligonucleotides have been prepared which contain alternate linkages, such as methylphosphonates (wherein a phosphorous-linked oxygen has been replaced with a methyl group), phosphorothioates (wherein a phosphorous-linked oxygen has been replaced with a sulfur group), and various amidates (wherein $NH_2$ or an organic amine replaces one of these oxygen atoms); see e.g., the work primarily reviewed by Uhlmann & Peyman [8] and others [9–14].

Other efforts have been focused on changing or replacing phosphodiester groups or other parts of the sugar phosphate backbone by variety of linkages which include, for example: carbamate derivatives and morpholine derived carbamate derivatives [15, 16]; polyvinylic derivatives [17, 18]; polyphosphate derivatives [19]; polylysine derivatives and polyethylene amine derivatives [20]; peptidic derivatives [21–33]; nylon-based derivatives [34, 35]; and polyamide derivatives [36–42].

In some of these cases the modified oligomers were capable of hybridizing to the target nucleic acid, but exhibited shortcomings related to stability, sensitivity to degradative enzymes and/or cellular uptake. In some other cases, the modified oligomers were relatively stable, and fairly resistant to degradative enzymes (due to the unusual linkages), but hybridization between these modified oligomers and their nucleic acid targets was sub-optimal. (As described below, we believe that some of these shortcomings may be due to the electrostatic and/or spatial properties of these oligomers.)

Accordingly, there remains a need for molecules that are: (i) relatively easily taken up and transported by cells; (ii) relatively stable and resistant to cellular degradative enzymes; and (iii) effective at binding to complementary nucleic acids.

SUMMARY OF THE INVENTION

It is a primary object of the present invention to provide a molecule that is able to function like a nucleic acid in antisense targeting but which overcomes certain of the disadvantages associated with the use of oligonucleotides (ODNs) for antisense targeting.

The present invention provides a chimeric molecule referred to as a "peptide-based nucleic acid mimic" (or "PENAM"). These chimeric molecules have a peptide-like backbone with side chains that contain bases resembling those normally found in nucleic acids. The bases on the nucleic side chains of the PENAM allow the molecule to engage in hydrogen bonding with a target nucleic acid having a substantially complementary sequence of bases; or to engage in triple helix formation, as described below.

The chimeric PENAMs of the present invention also have an unusual stereochemical composition that facilitates binding to the target nucleic acid. In particular, the PENAMs of the present invention have a peptidic backbone that incorporates unusual chiral centers (including D-chiral centers and quasi-chiral centers) that can be used to orient the nucleic side chains in such a way that the nucleotidic bases are spatially homomorphic to bases in targeted nucleic acids. The ability to enhance binding by spatial homomorphism is especially significant given that hydrogen bonding interactions between biomolecules typically depend on an aggregation of many relatively weak bonds. The PENAMs are also much less susceptible to electrostatic charge repulsion (because of the replacement of the normally charged backbone). Also, by virtue of their unusual structural and stereochemical features, the PENAMs of the present invention are resistant to degradative enzymes that are expected to be present in most biological systems. In particular, the PENAMs do not possess the phosphodiester backbone which is the standard target of the nucleases. Moreover, the peptidic backbone is unlike that of naturally occurring peptides because of the presence of unusual chiral centers including D-chiral centers and/or quasi-chiral centers.

In addition, the peptidic backbone is assembled from monomers (termed "NuAA monomers", described below) which can themselves be conveniently linked using peptide synthetic techniques. These building block NuAA monomers thus allow for the rapid production of a variety of "antisense" oligomers (exhibiting differing sequences for targeting particular complementary nucleic acids), via an automated peptide synthesizer.

Thus, one aspect of the present invention is a novel chimeric oligomer having bases that resemble those in ODNs, but in which the entire ribose- or deoxyribose-phosphate backbone has been replaced with a peptidic backbone that has been designed to incorporate unusual chiral centers including D-chiral centers and/or quasi-chiral centers. The resulting peptidic backbone is capable of orienting the side chains such that the nucleic acid mimic can effectively bind to a complementary target nucleic acid. These novel chimeras, termed "peptide-based nucleic acid mimics" (or "PENAMs") are stable under physiological conditions and resistant to degradative enzymes, and are electrostatically and spatially designed for enhanced transport across cellular membranes and effective binding to target nucleic acids.

One aspect of the invention is a composition useful in targeting a nucleic acid comprising a stereochemically-selected population of peptide-based nucleic acid mimics (PENAMs) each member of which comprises a sequence of at least about 4 NuAA monomers, wherein at least one of said PENAMs is a homomorphically-preferred PENAM comprising a D-chiral center or a quasi-chiral and wherein said homomorphically-preferred PENAM makes up at least about 10% of the stereochemically-selected population of PENAMs. The NuAA monomers are each of the following formula:

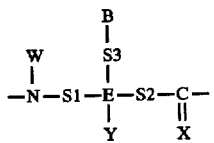

wherein:

E is carbon (C) or nitrogen (N);

W is hydrogen or a spacer group;

Y is hydrogen or a spacer group (when E is carbon), or Y is a lone pair of electrons (when E is nitrogen);

S1 is a bond or a first spacer group;

S2 is a bond or a second spacer group;

S3 is a bond or a third spacer group;

X is oxygen (O) or sulfur (S);

B is a base segment comprising a nucleotidic base or an analog thereof; and

N is nitrogen.

Preferably, the homomorphically-preferred PENAM makes up at least about 30% of the stereochemically-selected population of PENAMs; more preferably at least about 50%; still more preferably at least about 80%.

Another aspect of the invention is free NuAA monomer that is a precursor of a NuAA monomeric subunit comprising a quasi-chiral center wherein said NuAA monomeric subunit comprising a quasi-chiral center is of the following formula:

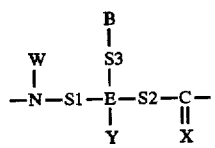

wherein:

E is nitrogen (N);

W is hydrogen or a spacer group;

Y is hydrogen or a spacer group (when E is carbon), or Y is a lone pair of electrons (when E is nitrogen);

S1 is a bond or a first spacer group;

S2 is a bond or a second spacer group;

S3 is a bond or a third spacer group;

X is oxygen (O) or sulfur (S);

B is a base segment comprising a nucleotidic base or an analog thereof; and

N is nitrogen;

wherein said free NuAA monomer is of the same formula except that it has an amine group or a protected amine group at its N-terminus and it has a carboxyl group or a protected carboxyl group at its C-terminus.

Another aspect of the invention is a free NuAA monomer that is a precursor of a NuAA monomeric subunit comprising a D-chiral center wherein said NuAA monomeric subunit comprising a D-chiral center is of the following formula:

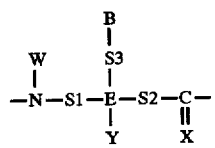

wherein:

E is carbon (C);

W is hydrogen or a spacer group;

Y is hydrogen or a spacer group;

S1 is a bond or a first spacer group;

S2 is a bond or a second spacer group;

S3 is a third spacer group with a backbone of at least two atoms;

X is oxygen (O) or sulfur (S);

B is a base segment comprising a nucleotidic base or an analog thereof; and

N is nitrogen;

and wherein at least one of S1 and S2 is a spacer group, and wherein S3 is a spacer group with a backbone of at least two atoms;

wherein said free NuAA monomer is of the same formula except that it has an amine group or a protected amine group at its N-terminus and it has a carboxyl group or a protected carboxyl group at its C-terminus.

Another aspect of the invention is a method of preparing a PENAM composition for targeting a target nucleic acid comprising: (a) providing at least about 4 NuAA monomers, preferably at least about 6 NuAA monomers, wherein at least one of said NuAA monomers comprises a D-chiral center or a quasi-chiral center; and (b) synthesizing an oligomer of the monomers such that the arrangement of bases in the oligomer is substantially complementary to a sequence of nucleotidic bases in a portion of the target nucleic acid. Preferably step (a) involves providing at least about 6 NuAA monomers, more preferably at least about 10 NuAA monomers, still more preferably at least about 14 NuAA monomers. The NuAA monomers can be linked to each other directly forming peptide bonds, or indirectly via an intervening residue such as an amino acid residue.

Another aspect of the invention is a method of targeting a target nucleic acid comprising: (a) providing a PENAM composition; and (b) contacting said PENAM composition with the target nucleic acid.

Another aspect of the invention is a method of modulating a target nucleic acid in an antisense manner comprising: (a) providing a PENAM composition wherein the sequence of bases in said NuAA monomers is substantially complementary to a sequence of bases in the target nucleic acid; and (b) contacting said PENAM composition with the target nucleic acid.

Another aspect of the invention is a method of modifying a target nucleic acid comprising: (a) providing a PENAM composition wherein said homomorphically-preferred PENAM further comprises a target modifying group; and (b) contacting said PENAM composition with the target nucleic acid.

Another aspect of the invention is a method of detecting a target nucleic acid comprising: (a) providing a PENAM composition wherein the sequence of bases in said NuAA monomers is substantially complementary to a sequence of bases in the target nucleic acid; and (b) contacting said PENAM composition with the target nucleic acid; and (c) detecting a target complex comprising said nucleic acid mimic and said target nucleic acid or detecting a modification in the target nucleic acid.

Another aspect of the invention is a method of isolating a target nucleic acid comprising: (a) providing a PENAM composition wherein the sequence of bases in said NuAA monomers is substantially complementary to a sequence of bases in the target nucleic acid; and (b) contacting said PENAM composition with the target nucleic acid; and (c) isolating PENAMs bound to said target nucleic acid or isolating a modified target nucleic acid.

BRIEF DESCRIPTION OF THE DRAWINGS

FIGS. 4a and 4b are illustrative examples of the retrosynthesis of PENAMs and NuAA monomers from α-amino-α-carboxylic acids.

DETAILED DESCRIPTION OF THE INVENTION

Definitions

Figure 1:
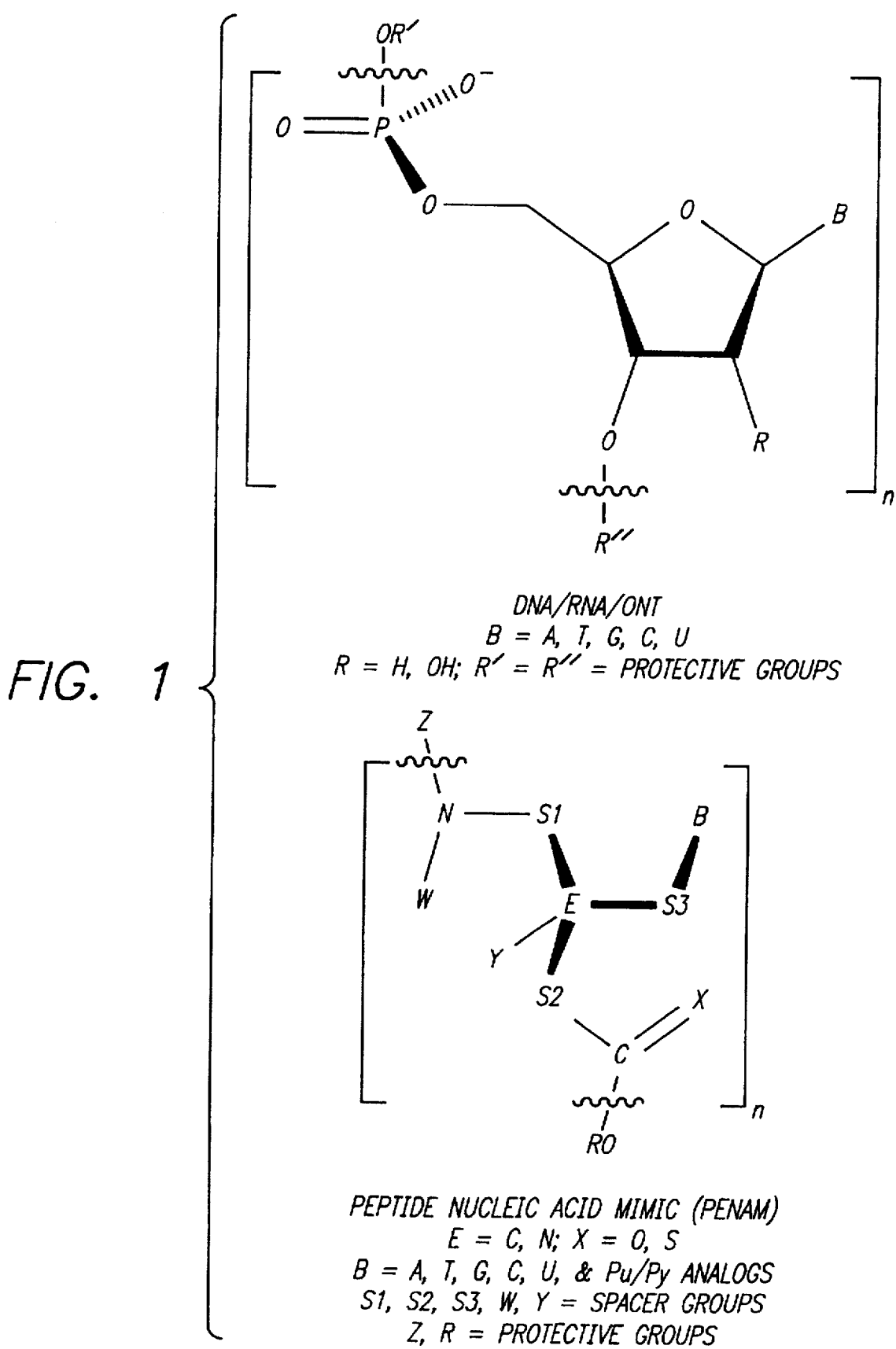
FIG. 1 is a comparison of monomers in oligo(deoxy) nucleotides (such as DNA and RNA, collectively referred to as "ODNs"), and the NuAA monomers that form the peptide nucleic acid mimics (PENAMs) of the present invention.

The following definitions are intended to supplement, not to replace, the detailed descriptions of these and other aspects of the invention which are described herein.

A "peptide-based nucleic acid mimic" (or "PENAM", sometimes referred to as a "peptide nucleic acid mimic" or "nucleic acid mimic"), refers to a molecule having a peptidic backbone with side chains having nucleotidic bases that are capable of engaging in hydrogen bonding with a nucleic acid having a complementary sequence of bases. The PENAMs of the present invention are assembled from NuAA monomers, but may also contain other chemical groups such as "target modifying groups", natural amino acids or peptides, and other groups as described below. Such additional groups may be located within an individual NuAA monomer, or may occupy positions either between NuAA monomers or outside of a string of NuAA monomers. The term "monomer" is used to refer to individual molecules that can be incorporated by polymerization into larger molecules; and is also used to refer to the corresponding monomeric subunits (i.e. after incorporation into the larger molecule).

The term "complementary" indicates that a particular sequence of bases is able to pair (as in Watson-Crick base-pairing) with corresponding bases in a given target sequence. The term "substantially complementary" indicates that at least about 80% of the bases in a particular sequence are able to engage in base-pairing with corresponding bases of the target sequence. The term "partially complementary" indicates that at least about 60% of the bases in a particular sequence are able to engage in base-pairing with corresponding bases of the target sequence.

A "target nucleic acid" refers to a nucleic acid comprising a sequence of bases that is at least partially complementary to a sequence of base groups on a targeting PENAM.

The "peptidic backbone" refers to the portion of a PENAM that comprises peptide bonds derived from the aminoacyl portions of the NuAA monomers and/or intervening aminoacyl monomers such as natural or unnatural amino acids.

The "nucleic side chains" refer to portions of the PENAM that comprise nucleotidic bases which are capable of engaging in hydrogen bonding with corresponding bases on a target nucleic acid.

A "nucleic aminoacyl monomer" (or "nucleic aminoacyl monomeric subunit") refers to a monomeric subunit of the following formula:

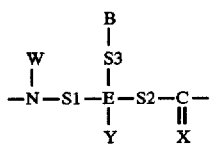

wherein:

E is carbon (C) or nitrogen (N);

W is hydrogen or a spacer group;

Y is hydrogen or a spacer group (when E is carbon), or a lone pair of electrons (when E is nitrogen);

S1 is a bond or a first spacer group;

S2 is a bond or a second spacer group;

S3 is a bond or a third spacer group;

X is oxygen (O) or sulfur (S);

B is a base segment comprising a nucleotidic base or an analog thereof; and

N is nitrogen.

A "free nucleic amino acid monomer" (or "free NuAA monomer") refers to a precursor of a nucleic aminoacyl monomer. The precursor monomer is essentially of the same formula as shown above except that the N-terminus (i.e. the N with a free bond in the formula) is in the form of an amine or protected amine (e.g. a carbamate); and the C-terminus (i.e. the C with a free bond in the formula) is in the form of a carboxylic acid or, e.g., an ester.

"NuAA monomer" is used to refer to both free NuAA monomers and to corresponding NuAA monomeric subunits after incorporation into a larger molecule.

An "aza-NuAA monomer" refers to a NuAA monomer of the formula shown above in which E is nitrogen. The nitrogen at position E forms a "quasi-chiral center" as discussed herein.

An "L-NuAA monomer" refers to a NuAA monomer in which E is carbon and is a chiral center that is in a stereochemical configuration corresponding to that of an analogous L-amino acid (i.e., an L-amino acid having an R group in place of S3-B and having carbonyl and amide groups oriented in the directions as shown in the formula above).

A "D-NuAA monomer" refers to a NuAA monomer in which E is carbon and is a chiral center that is in a stereochemical configuration corresponding to that of an analogous D-amino acid (i.e., a D-amino acid having an R group in place of S3-B and having carbonyl and amide groups oriented in the directions as shown in the formula above). The carbon at position E in a D-NuAA monomer forms a "D-chiral center" as discussed herein.

An "aminoacyl monomer" (or "AA monomer") refers to a structure that resembles a NuAA monomer as shown in the formula above, but lacks the base segment at position B. Thus, AA monomers are derived from amino acids such as a natural or unnatural amino acids. Such AA monomers can be incorporated into PENAMs and can (either singly or in strings) occupy positions between NuAA monomers. Such AA monomers can, like NuAA monomers, comprise D-, L- and/or quasi-chiral centers.

An "aza-aminoacyl monomer" (or "aza-AA monomer") refers to an analog of an AA monomer in which the chiral center (i.e. the carbon at position E) is replaced with a quasi-chiral center (i.e. a nitrogen at position E).

A "stereochemically-selected population of PENAMs" refers to a population of PENAMs each member of which comprises a sequence of at least about 4 NuAA monomers, wherein at least one of said PENAMs, denoted a "stereochemically-prevalent PENAM" makes up at least about 10% of said population of PENAMs, preferably at least about 30%, more preferably at least about 50%, still more preferably at least about 80%. Generally, the remaining PENAMs in the stereochemically-selected population will be diastereomers of the stereochemically-prevalent PENAM(s); although the population may also include PENAMs of other lengths and/or structure. Stereochemically-selected populations of PENAMs can be most conveniently prepared by utilizing enantiomerically pure starting reagents (preferably at least about 90% enantiomeric excess, more preferably at least 95%, still more preferably at least about 99%), such as D- or L-amino acids, as described herein. Alternatively, one could resolve selected stereochemical intermediates or products, or employ stereoselective synthetic techniques.

A "homomorphically-preferred" PENAM refers to a PENAM that exhibits structural and stereochemical properties that facilitate binding between a sequence of nucleotidic bases in the PENAM and a substantially complementary sequence of bases on a target nucleic acid. Homomorphically-preferred PENAMs of the present invention comprise at least one D-chiral or quasi-chiral center. Homomorphically-preferred PENAMs can comprise various combinations of monomers including, e.g., NuAA monomers and AA monomers (both of which can contain D- and/or L-chiral centers); and aza-NuAA monomers and aza-AA monomers (both of which contain quasi-chiral centers).

The term "flanked" or "flanking" refers to the two positions in the peptidic backbone immediately adjacent to a particular NuAA monomer.

A "spacer group" refers to a relatively small chemical group, or series of small chemical groups, that may be included in the peptidic backbone or nucleic side chains either between adjacent atoms (i.e., at positions S1, S2, and/or S3), or dependent from atoms (i.e. at W and/or Y) in the formula shown above; and that is unlikely to inhibit hydrogen bonding between the targeting PENAM and the target nucleic acid. These spacer groups contain a backbone of 1–6 atoms (not counting hydrogen atoms), preferably selected from carbon, nitrogen, oxygen, and sulfur. Typically, such spacer groups are substituted or unsubstituted alkyl, alkenyl, alkynyl groups. However spacer groups can also comprise for example: carbonyl (C=O), thiocarbonyl (C=S), amine (NH), substituted amine (NR), amide {C(=O)NH}, substituted amide {C(=O)NR}, carbamate {NHC(=O)O}, urea {NHC(=O)NH}, thioamide {C(=S)NH}, substituted thioamide {C(=S)NR}, hydrazine (NH—NH), substituted hydrazine {N(R)—N(R)}, ether (C—O—C), thioether (C—S—C), disulfide (S—S), sulphone {S(=O)} and sulphoxide (SO2) groups. The spacer group backbone can also be substituted with one or more small chemical groups, for example, small chain alk(ane, ene, yne)s, hydroxyl (OH), alkoxyl (OR), ketone (COR), aldehyde (CHO), thiol (SH), amine (NH2), and halogen (F, Br, Cl) groups. A single NuAA monomer may contain more than one spacer group (at W, Y, S1, S2 and S3 for example) and these need not be identical to each other. Currently preferred spacer groups are selected from methylene, ethylene and propylene groups.

A "base segment" refers to a chemical group comprising the base portion of a nucleotidic base or an analog thereof, as described below.

A "nucleotidic base" or "nucleic base" refers to a nitrogenous heterocyclic group typically found in nucleic acids (such as the purine bases adenine and guanine, or the pyrimidine bases cytosine, thymine and uracil) or an analog thereof. An "analog" of a nucleotidic base refers, for example, to an analog of a purine base in which the ring substituents are other than those found in adenine or guanine, or an analog of a pyrimidine base in which the ring substituents are other than those found in uracil, thymine and cytosine. Examples of such analogs are described below and in the art.

A "target modifying group" refers to a chemical group on a PENAM that is capable, after the PENAM has hydrogen bonded to a target nucleic acid, of modifying the target nucleic acid. Such modifying groups include for example groups which label, reconform, cleave, covalently bind or intercalate into nucleic acids. Examples of such target modifying groups are described below.

A nucleic acid "labeling group" refers to a group on a PENAM which, as a result of the interaction between the mimic and its target, facilitates labeling and thus detection of the target nucleic acid. Examples of such labeling groups are described below.

A nucleic acid "intercalating group" refers to a group on a PENAM which, as a result of the interaction between the mimic and its target, intercalates into double helical target nucleic acid. Examples of such intercalating groups are described below.

A nucleic acid "cleaving group" refers to a group on a PENAM which, as a result of the interaction between the mimic and its target, facilitates the cleavage of the target nucleic acid. Examples of such cleaving groups are described below.

The phrase "modulating in an antisense manner" refers to modulating the expression and/or activity of a nucleic acid via hydrogen bonding interactions analogous to those described in systems involving antisense oligonucleotides.

The term "homomorphic" (or "homomorphous") refers to the stereochemical fit between a sequence of bases in the targeting portion of a PENAM and a target nucleic acid wherein at least about ½ of the bases of the targeting portion of the mimic are positioned to allow hydrogen bonding with complementary bases on the target nucleic acid. Preferably at least about ⅔ of the bases are so positioned; more preferably at least about ¾ of the bases are so positioned; most preferably all of the bases are so positioned.

All publications cited herein, including scientific papers, published patent applications and issued patents, are incorporated herein by reference in their entirety.

1. Nucleic Aminoacyl Monomers (NuAA Monomers)

The peptide-based nucleic acid mimics ("PENAMs") of the present invention comprise a sequence of nucleic aminoacyl monomers ("NuAA monomers"). NuAA monomers are chimeric molecules and/or monomeric subunits of the following formula:

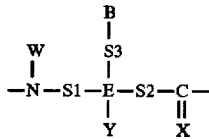

wherein:
E is carbon (C) or nitrogen (N);
W is hydrogen or a spacer group;
Y is hydrogen or a spacer group (when E is carbon], or a lone pair of electrons (when E is nitrogen];
S1 is a bond or a first spacer group;
S2 is a bond or a second spacer group;
S3 is a bond or a third spacer group;
X is oxygen (O) or sulfur (S);
B is a base segment comprising a nucleotidic base or an analog thereof; and
N is nitrogen.

In free NuAA monomers (i.e. before incorporation into a polymer), the N-terminus (i.e. the N with a free bond in the formula) is in the form of an amine or protected amine (e.g. a carbamate); and the C-terminus (i.e. the C with a free bond in the formula) is in the form of a carboxylic acid or, e.g., an ester.

Nucleotidic bases include the usual bases found in nucleic acids (i.e., the purine bases of adenine and guanine, and the pyrimidine bases of cytosine, thymine and uracil) and analogs thereof. A number of analogs of nucleotidic bases are well known in the art; many of which have been tested as chemotherapeutic agents. Some of these are described herein; see also, e.g., Beilstein's Handbuch der Organischen Chemie (Springer Verlag, Berlin), and Chemical Abstracts, which provide references to publications describing the properties and preparation of such compounds, which publications are incorporated herein by reference.

Thus, a large variety of analogs have been described that exhibit properties that may be advantageous in particular targeting schemes. For example, in some cases, it may be desirable to incorporate a base that binds non-specifically at a particular position. The base present in inosine is an example of such a non-specific analog. This can be used to incorporate degeneracy into the PENAM at particular positions which might be particularly useful, for example, in targeting a closely related family of target nucleic acids that are homologous except for one or a few positions in the base sequence. Inosine can pair with all four natural bases although the strength of binding varies: dC>dA>dG/T. See, e.g., [43].

Other types of modified bases that may be of particular interest are those which enhance binding affinity. For example, diaminopurine can form three hydrogen bonds with thymine, whereas adenine and thymine form only two [44]. Similarly, pyridopyrimidine bases can be used in place of cytosine to provide stronger base pairing with guanine [45].

Bases can also incorporate any of a variety of "target modifying groups". By way of illustration, base analogs can function as cross-linking moieties. For example, 6-bromo-5,5,-dimethoxyhexanohydrazide can be introduced into the $C^4$ position of cytidine to alkylate and thereby cross link guanosine [46]. $N^4,N^4$-Ethano-5-methyl-cytosine can be used to similar effect [47, 48].

Another example of base analogs that can be incorporated into a PENAM are fluorescing analogs such as the base of pyridopyrimidinedeoxynucleosides [45]. Such bases can thus be used as labeling groups.

A wide range of purine and pyrimidine analogs exhibiting various properties is known in the art [see, e.g., references 49–62]. An exemplary but not exhaustive list of such analogs includes: 1-methyladenine, 1-methylguanine, 1-methylinosine, 1-methylpseudouracil, 2-methylthio-$N^6$-isopentenyladenine, 2-thiocytosine, 2-methyladenine, 2-methylguanine, 2-thiouracil, 2,2-dimethylguanine, 2,6-diaminopurine-3-methylcytosine, 3-(3-amino-3-N-2-carboxypropyl)-uracil-4-acetylcytosine, 4-thiouracil, 5-fluorouracil, 5-iodouracil, 5-bromouracil, 5-methyluracil, 5-methyl-2-thiouracil, 5-methoxyaminomethyl-2-thiouracil, 5-chlorouracil, 5-carboxymethylaminomethyl-2-thiouracil, 5 - m e t h y l a m i n o m e t h y l u r a c i l, 5 - c a r b o x y h y d r o x y l m e t h y l u r a c i l , 5-carboxymethylaminomethyluracil, 5-methoxyuracil, 5-methylcytosine, 7-methylguanine, 7-deazaguanine, 7-deazaadenine, β-D-mannosylqueosine, β-D-galactosylqueosine, dihydrouracil, hypoxanthine, inosine, N-uracil-5-oxyacetic acid methylester, $N^6$-methyladenine, $N^6$-isopentenyladenine, pseudouracil, queosine, uracil-5-oxyacetic acid methylester, uracil-5-oxyacetic acid, and xanthine.

Particular spacer groups, e.g., at S1, S2, S3, W and/or Y in the formula, are as described above. The incorporation of spacer groups at S1 and S2 will affect the relative distance between adjacent bases on NuAA monomers. Preferably, the distance between adjacent bases is at least about 4 carbon-carbon bond lengths, more preferably at least about 5, still more preferably about 6. This spacing can be achieved by including a corresponding number of atoms between the E position of one NuAA monomer and the E position of the next NuAA monomer. Thus, to incorporate about 6 bond lengths, for example, one can include 5 atoms along that length of the backbone. The desired "spacer" atoms can be incorporated within NuAA monomers (for example, by using monomers with a propylene moiety at S2 or S1, or e.g. a methylene at S1 and an ethylene at S2). Most preferably, however, S1 is a bond since that will facilitate the synthesis of NuAA monomers from naturally occurring amino acids and their derivatives. As described below there are a number of commercially available amino acids that can be used as precursors for the synthesis of NuAA monomers having a variety of spacer groups at S2. As described in Example 2, molecular modelling can be used to assess the likely impact of, for example, lengthening the spacer group at S2. Preferably, S2 is a methylene group, more preferably an ethylene group, still more preferably a propylene group.

Alternatively, the spacer atoms can be provided by monomers located between NuAA monomers. Since aminoacyl monomers derived from natural amino acids will provide a three-atom backbone, these can be conveniently used between adjacent NuAA monomers. Such spacer AA monomers can also be used to provide D- or L-chiral centers. Similarly, aza-AA monomers can be used to provide quasi-chiral centers between adjacent NuAA monomers. Thus, individual PENAMs can include one or more types of monomers and/or chiral centers.

The spacer group at S3 is used to affect the distance between the nucleic base and the peptidic backbone. Molecular modelling has been used to show that, in order to mimic the homomorphism of native nucleic acids, the nucleic base is preferably substituted on the side chain at least two carbon units distance from the peptidic backbone (e.g., γ-substituted), and is preferably not more than four carbon units away from the backbone. Such NuAA monomers can be easily synthesized from commercially available starting materials, for example, natural alpha-amino acids, as illustrated below.

The atom at E will generally be a carbon, in which case E can be a chiral center analogous to the alpha carbon of a natural amino acid (other than glycine). When E is a chiral center, then the NuAA monomers can be L- or D-NuAA monomers depending on whether the configuration of groups around the chiral center is analogous to that found in an L- or D-amino acid (where the base segment is in the position normally occupied by an amino acid "R" group and the carbonyl and amide groups are in the directions shown in the formula). As described herein, the PENAMs of the present invention contain D-chiral and/or quasi-chiral centers.

If E is carbon, then W and Y can be hydrogen or a spacer group as defined above. Most preferably, W and Y are hydrogen atoms.

When the atom at E is replaced isosterically with trivalent nitrogen in place of carbon, the resulting NuAA monomer (termed an "aza-NuAA monomer") can adopt configurations between D- and L- amino acids. Thus, there will generally be a lone pair of electrons at position Y; and, since the electrons are not fixed, the resulting center around E can adopt a variety of spatial configurations and is referred to as a quasi-chiral center.

NuAA monomers can be conveniently synthesized from generally available starting materials such as natural amino acids, unnatural amino acids and the derivatives thereof, see, e.g. [63–65]. As will be appreciated, a variety of possible synthetic routes can be employed. "Retrosynthesis" techniques can be used to identify particularly convenient pathways; some of which are illustrated below.

As described below, the design of such mimics can be tested by well-known molecular modelling techniques in order to assess the likely impact of a particular group on binding of the targeting bases of the side chain to their nucleic acid target.

2. Assembly of Particular PENAMs from NuAA Monomers

The PENAMs of the present invention contain strings of NuAA monomers (although they may also contain other groups, as described herein). The sequence of bases in the PENAM can be made to complement any target nucleic acid sequence by simply incorporating the corresponding NuAA monomers into the PENAM. Thus, where a gene or other nucleic acid target has already been at least partially sequenced, then PENAMs can be designed to interact with such a target nucleic acid according to the standard "rules" of Watson-Crick base-pairing (i.e., a single-stranded nucleic acid comprising a nucleotide sequence CCGGTTAA could be targeted by a PENAM comprising a base sequence GGCCAATT; note that longer sequences are generally used, as described below).

Several basic considerations guide selection of a suitable number of bases to include. Two particularly important consequences of increasing the length of the complementary region are an increase in specificity and an increase in affinity. The increased specificity derives from the fact that the general probability of occurrence of a particular target sequence will be $(¼)^n$, where n is the number of bases in the target sequence. Thus, the probability (P) that a particular sequence of n bases will occur in a nucleic acid containing a total of N bases can be estimated from the following formula:

$$P=N/4^n$$

For example, the probability that a 10 base sequence will occur in a nucleic acid of 30,000 nucleotides (30 Kb) would be estimated to be $3 \times 10^4/4^{10}$ or about 0.03; and the probability of a 15 base sequence occurring would be approximately 0.0000279. Thus, for targeting sequences in a viral genome, most of which have less than 300 kb of unique-sequence nucleic acid, a sequence of less than 15 bases, and perhaps as few as 9 or so, may provide more than sufficient specificity of targeting. In more complex genomes, it is preferable to have a longer sequence. Thus, a 17 base sequence would be expected to occur once in the entire human genome [8].

It is also the case that overall binding affinity is improved by providing more bases for hydrogen bonding. This explains the correlation observed in antisense ODNs between chain length and antisense activity. For duplexes in the range of 10 to 20 base pairs (bp), the melting temperature increases by roughly three degrees Celsius for every additional base pair formed by two hydrogen bonds (e.g., A:T)

and by roughly six degrees Celsius for every additional base pair formed by three hydrogen bonds (e.g., G:C). Thus, a sequence number selected on the basis of specificity [vis-a-vis the complexity of nucleic acid in the targeted genome(s)] may be extended to influence the affinity of binding. However, the significance of the correlation between length and affinity is greatly reduced once the number of bases exceeds about thirty [8]. Furthermore, longer sequences may be more difficult to synthesize and may penetrate cellular membranes less efficiently. Of course, a preferred approach will be to identify an appropriate range, typically 10 to 25 bases, and then to compare a set of oligomers of differing lengths within that range to determine an optimum length. Synthesizing a range of PENAMs of differing lengths and/or specificities can be easily accomplished using the present invention since the PENAMs are designed to be prepared using modular synthesis on a peptide synthesizer.

The particular bases incorporated within the PENAM will of course depend on the desired nucleic acid target. As is well known to those of skill in the arts of DNA probes and antisense technology, the overall binding of the targeting molecule to its target depends, inter alia, on the length of the complementary sequences and the number of mismatches within those sequences. Preferably, the PENAMs of the present invention will be at least "partially complementary" (60% homologous) to a stretch of bases in the target nucleic acid. More preferably, the PENAM will be "substantially complementary" (at least about 80% homologous); most preferably, the PENAM will be "completely complementary" (100% homologous). As discussed above, however, it is quite feasible to incorporate special base analogs (such as inosine) to effectively broaden the binding capability for one or more positions in the monomer (if, for example, it represents a position that is unidentified, or is likely to vary in a given population of target sequences). It is also feasible to incorporate other analogs to further enhance binding; see the illustrations above regarding the use of modified bases with enhanced affinity, and the use of cross-linking moieties.

PENAMs can also target double-stranded target nucleic acids via triple helix formation, as discussed below.

It is also possible to combine the PENAM technology of the present invention with the use of standard oligo(deoxy) nucleotides (i.e., "ODNs"). Thus, for example, a PENAM might include a sequence of "natural" nucleotides. However, since the predominant activity of exonucleases appears to be 3' to 5' it would be preferable to have at least the 3' end of such an ODN linked to another portion of the PENAM.

Homomorphism

The PENAMs of the present invention have a peptidic backbone that incorporates unusual chiral centers (including D-chiral centers and/or quasi-chiral centers) that can be used to orient the nucleic side chains in such a way that the nucleotidic bases are spatially homomorphic to bases in targeted nucleic acids. The ability to enhance binding by spatial homomorphism is especially significant given that hydrogen bonding interactions between biomolecules typically depend on an aggregation of many relatively weak bonds.

For optimal binding, it is believed that the PENAM should have a conformation in which the nucleotidic bases are stacked approximately at the 3.5 Angstrom interval and are oriented away from the backbone in such a manner that the hydrogen bond donors and acceptors of the nucleotidic bases can directly "read" the complementary bases on the target nucleic acids by specific hydrogen bonding interactions. That is, the PENAM and the target should be substantially homomorphic. In order to achieve such homomorphism, the PENAMs of the present invention comprise strings of NuAA monomers (and may comprise other intervening monomers) in which the NuAA monomers (or the intervening monomers, or both) can incorporate unusual chiral centers, including D-chiral centers and/or quasi-chiral centers.

The various monomers and chiral centers can be incorporated into PENAMs in a variety of different configurations. Thus, PENAMs can incorporate, for example, mixtures of L- and D-chiral centers; which can be in unequal proportions or in roughly equal proportions. PENAMs with roughly equal proportions of L- and D-chiral centers can have these centers dispersed (e.g. wherein at least about 85% or L-chiral centers are flanked by D-chiral centers). Higher proportions of D-chiral centers can also be used (e.g. wherein at least about 80% of the centers are D-chiral centers). Quasi-chiral centers can be incorporated in addition to, or in place of, D- and/or L-chiral centers; and these allow the resulting PENAM to adopt a variety of spatial conformations at the quasi-chiral centers. Molecular modelling with energy minimization of PENAM strands in association with a target DNA strand, as illustrated below, can be used to predict the preferred positioning of the particular chiral centers and/or quasi-chiral centers for a particular PENAM structure.

NuAA monomers can be joined directly to each other or they can be separated by intervening monomers of other types. Preferably, such other monomers (or strings thereof) are amino acids and/or aza-amino acids, or their derivatives, since all of these monomers can then be conveniently polymerized via peptide synthesis techniques. Of course, it will also be possible to separately prepare larger fragments, such as polypeptide fragments, and then incorporate such fragments into a PENAM.

As discussed herein, the peptide backbone of the PENAMs of the present invention serves as a scaffold to orient the side chains (—S3—B in the formulae) in such a way that the nucleic bases substituted in the side chain can "read" the complementary nucleic bases sequence on the target nucleic acid. From the rational drug design point of view, the peptide backbone scaffold can be chemically modified to alter its hydrophobicity/hydrophilicity, or its electronic and/or stereochemical properties [66–68]. An exemplary but not exhaustive list of such chemical modifications includes: 1) modifications of the amide nitrogen; 2) modifications of the alpha-carbon (where E is carbon); 3) modifications of the amide carbonyl; and 4) modifications of the amide bond. Decreasing the hydrophilicity of the backbone can be expected to improve uptake of the molecules. Decreasing the electronegativity of the backbone can also be expected to enhance binding to a complementary nucleic acid (which is itself electronegative). In these regards, the PENAMs of the present invention (in which the polyphosphate-sugar backbone has been entirely replaced) are already substantially improved relative to standard ODNs. However, additional modifications affecting hydrophilicity/electronegativity can also be incorporated. Modifications in the backbone (especially at S2 and/or S3) can be used to favor particular conformations (e.g. helix vs. beta-sheet) and to thereby improve base stacking.

Molecular modelling techniques can be used to assess the likely impact of a particular group (such as a larger spacer group) on binding of the targeting bases of the side chain to their nucleic acid target. A number of suitable molecular modelling techniques are known in the art [69–75], and computer software incorporating such techniques is also available, as described below.

Molecular modelling, often synonymous with computer-aided molecular design, is a general methodology which comprises several computer-based methods for drug design [76, 77]. Using these methodologies, one can readily assess the impact of introducing various modifications into targeting molecules such as the PENAMs of the present invention. A number of publicly available modelling packages, including BIOGRAPH-II®, CHEMLAB-II®, CHEM-X®, HYPERCHEM®, MACRO MODEL®, SYBYL®, and others, can offer some or all of the following advantages that can be used to design and check particular PENAMs of the present invention. Some of the useful features of these systems are outlined below.

Model building and computer graphics programs allow users to "build" a molecule from scratch or import it from 3D structure data bases and also allow manipulations of the displayed model, ranging in size from small molecules to macromolecules in 3D. They also enable the user to dock more than one ligand into the putative active site of the macromolecule and to manipulate the display simultaneously or individually. Publicly available programs of this type include, for example: ALCHEMY®, from Tripos associates; MIDAS PLUS®, from The University of California, San Francisco; FRODO®, from Rice University, Houston; HYDRA® from Polygen; MANOSK® from University of Paris; MOLECULAR GRAPHICS® from ACS software; and MOGLI® from Evans and Sutherland. Molecular model building programs like CONCORD® and COBRA® can also be used to generate low energy 3D structures from 2D on work stations [78].

Molecular mechanics and dynamic simulation programs allow model refinement by optimizing the rough coordinates of the model, utilizing either quantum mechanics or molecular mechanics calculations. Molecular mechanics can optimize the 3D structure of a molecule by moving to the nearest local minimum energy structure. Even though both quantum mechanics and molecular mechanics have their basic differences in calculating the potential energy function of an isolated molecule or a biological system, they complement each other and can be used to optimize the interaction energy and the binding conformation between the ligand and its target macromolecule [79, 80]. Molecular dynamics simulations can be used to follow the solvation and conformational changes involved in the interactions between the ligand and its receptor on initial binding, and also any conformational or covalent rearrangements which may occur on subsequent binding. Molecular dynamics can be used to assess entropies, enthalpies and other thermodynamic quantities for various molecular configurations [81]. Accordingly, these calculations can be used to predict how variations in the basic structure of a PENAM will affect the equilibrium constant for binding to its target. Publicly available programs of this type include, for example: MM2® and MOPAC®, from Quantum Chemistry Program Exchange; and MMP2®, from Molecular Design Ltd. In addition, AMBER® and GROMOS®, from The University of California, San Francisco, are two programs available for molecular mechanics and dynamics simulations [80].

Docking, scoring and screening algorithms can also be used as computer screening procedures to test lead candidates for binding to putative ligands. The docking criteria typically involve either geometric orientation or steric match and evaluating the goodness of fit of the "ligand" to the active site. The scoring algorithms use steric complementarity, full intermolecular force field and other molecular properties as the scoring functions. Publicly available programs of this type include, for example: DOCK®, from The University of California, San Francisco [82–84]; GEOM®, from the Cambridge Structural Data Center; ALADDIN®, from Daylight chemical Information Systems, and MACCS-3D® from Molecular Design Ltd. [78].

Quantitative structure-activity relationships (QSAR) and statistical programs can be used to correlate the biological potency of a series of analogs with the relative values of physical properties such as partition coefficients (log P), $pK_a$, values, and electronic or steric properties and the size of the substituent. In addition to QSAR, the comparative molecular field analysis (CoMFA), which is a combination of receptor mapping, potential energy calculations and QSAR, uses the relative potency of molecules and their superimposed bioactive conformations to calculate steric, electrostatic and hydrogen-bonding interaction energies for each molecule [85, 86]. Statistical analysis of these energy values with respect to their biological potency or affinity can be used to predict the affinity of the proposed molecule for a given target. Publicly available programs of this type include, for example: MEDCHEM®, a modelling and information management program developed by Corwin Hansch at Pomona college [87], which includes algorithms to calculate log P values; and ADAPT®, another complete program, developed by Jurs et al. [88] and marketed by Molecular Design Ltd., which performs all the operations, i.e., vector representation of the molecules, statistical analysis by various methods, data input and management.

As an illustration of these techniques, Example 1 describes the use of molecular modelling to analyze the stereochemical impact of changes to the chirality of the peptidic backbone in the PENAMs of the present invention. In particular, a model of the PENAMs of the present invention was prepared in which the peptide backbone comprises alternating chiral centers, and this was compared to a model in which the backbone was assembled from "natural" L-amino acid-like monomers. As described in the example, the modelling data indicate that the ability to incorporate centers of varying chirality substantially improves the homomorphism or "fit" of the PENAM to its target nucleic acid. As described herein, centers of varying chirality including D-chiral, L-chiral and quasi-chiral centers can also be introduced into spacer monomers such as amino acids, incorporated between adjacent NuAA monomers.

It is known that DNA and RNA can exist in several secondary structures or isoforms such as right-handed A- and B-forms, as well as the left-handed Z-form, and it is believed that these isoforms could be essential for specific biological functions [89]. These polymorphisms in the double helix arise from differences in base stacking, backbone geometry, and the sugar conformation of the particular form. Each of these forms differ distinctly from each other with respect to helical hardness, as well as the shape and size of the helical groove. These distinct features have been effectively exploited to design conformation-specific metal complexes by Barton et al. [90]. Like synthetic ODNs, the PENAMs of the present invention are expected to be capable of binding to each of the various isoforms of the nucleic acids [91–93]. The molecular modelling techniques described above can be effectively used as a selection tool to assess the "homomorphic fit" of a particular PENAM to a generated molecular model of a specific nucleic acid isoform.

Assembly of PENAMs from NuAA Monomers

Since the NuAA monomers can be joined via peptide bonds, the PENAMs of the present invention can be conveniently assembled using well-known peptide synthetic techniques. These building block NuAA monomers thus allow for the rapid production of a variety of "antisense" oligomers, exhibiting differing sequences for targeting complementary nucleic acids, via an automated peptide synthesizer.

Solid phase peptide synthesis (SPPS) is a convenient and powerful methodology for the synthesis of a wide variety of oligopeptides in large quantity and high purity [94]. The methodology involves three basic steps: (i) peptide chain assembly; (ii) peptide cleavage, side chain group(s) deprotection and isolation from polymeric support; and (iii) purification and characterization of the oligopeptide.

The two most common synthesis strategies for SPPS are based on the deprotection chemistry of either t-Boc or Fmoc groups, used for the protection of the amino ($NH_2$) group of the amino acid. The choice of t-Boc or Fmoc depends upon the protection and deprotection chemistry of the functional groups of each monomer.

The first step in chain assembly is to attach the α-carboxyl group of the first t-Boc- or Fmoc-protected amino acid or aminoacyl monomer through a linker to a solid polymeric support. The next step is deprotection or removal of the t-Boc or Fmoc protective group of the first amino acid. The t-Boc protecting group is removed by an acid, usually trifluoroacetic acid (TFA), whereas Fmoc group is deprotected by base, usually piperidine. After deprotection, the next amino acid is coupled to the deprotected amino (NH2) terminus through its α-carboxyl (—COOH) group to form a peptide bond. Through successive cycles of deprotection and coupling, the growing peptide is assembled from the C-terminal towards the N-terminal to a desired chain length. Once the desired chain length is achieved, the oligopeptide is cleaved from the polymeric support either by a strong or weak acid. Also, depending upon the type of the resin linkage on the polymeric support, the cleaved oligopeptide has free carboxyl or carboxyamide at the C-terminus.

As described herein, the PENAMs of the present invention are unlikely to be degraded by either cellular nucleases or peptidases because of their unique structure which no longer resembles either nucleic acids or natural peptides. In addition, the uncharged backbone of PENAMs facilitates transport across the cell membrane. Uptake and transport across cellular membranes can be further enhanced by conjugating the PENAMs with carrier molecules at the N-terminus, at the C-terminus, or at an internal position in the PENAM. Carrier molecules include small reactive chemical groups (e.g., fluorescent dyes, intercalators, cross linking agents, alkylating agents, chain cleaving agents, biotin, digoxigenin, cholesterol, etc.) or stretches of other peptide-based compounds, including natural, modified or synthetic oligopeptides, or proteins (e.g., peroxidases, IgG, alkaline phosphatases and nucleases). They can be readily joined to the PENAMs via peptide bonds either during the synthesis or at the end of the synthesis on the peptide synthesizer [9]. Various strategies known in the art can be used to facilitate the uptake and selective subcellular localization of the PENAMs [95–109]. These strategies include:

1) increasing hydrophobicity by chemical modifications (for example, insertion of small chemical groups such as methylene, ethylene, propylene at S1 or, more preferably at S2 in a NuAA monomer) or by appending lipophilic groups such as cholesteryl and its derivatives and/or other long chain fatty triglyceryl residues;
2) physical or chemical association with polycations (for example, biotinylated molecules complexed to avidin can also exhibit increased cellular uptake, most probably due to the increased binding to the negatively charged cell surface (polycations would also enhance the binding of the PENAM to negatively-charged DNA);
3) conjugation to ligands recognizing membrane proteins and receptors (for example conjugation to mannose-6-phosphate substituted serum albumin or mannosylated streptavidin); of course, conjugation to ligands that associate with cell-specific receptors (e.g. conjugation to a cytokine that binds only to cells bearing a cognate cytokine receptor) can be used to specifically "target" the PENAM to a desired sub-population of cells;
4) delivery through nanoparticles made up of biodegradable polymers, such as polycyanoacrylate;
5) poly(L-Lysine) mediated delivery; and
6) association with lipoprotein or liposomes.

Tandem Targeting

A modification of the approach that may be especially effective is the use of "tandem targeting" in which more than one different oligomer is employed as described by Maher and Dolnick, and Goodchild et al. [110, 111]. In particular, the use of two or more distinct targeting sequences (complementary to adjacent regions of the target) may result in synergistic effects on the modulation of the target. Preferably, the gap between the adjacent regions of complementarity will be less than about 15 bases, still more preferably the gap will be less than about 2 bases, and most preferably there will be no gap.

Triple Helix Formation

Another way of targeting double-stranded DNA is via triple helix formation. There are several different motifs which are known to facilitate triple helix formation. In the "CT" motif, G—C basepairs are recognized by C residues and A—T basepairs are recognized by T residues—resulting in T—A—T and C—G—$C^+$ triplets across the three strands of the triple helical structure. This system is effective where one strand of the double-stranded target sequence contains only, or mostly, purine bases. An exception which may allow for a number of pyrimidine residues in the target sequence has been described by Griffin et al. [112]. The pyrimidine-rich targeting oligomer associates with the duplex such that the polarity of the oligomer is parallel to that of the strand containing the purine-rich target sequence. In situations in which a shorter purine-rich stretch is adjacent to a pyrimidine stretch, the oligomers may be designed to possess corresponding regions of inverted polarity such that the oligomer binds to the purine-rich stretch of one strand and then binds to the adjacent purine-rich stretch of the opposite strand. The recognition rules of the CT motif are further described by, for example, Maher et al. [113]; and Moser et al. [114]. One problem that may affect the use of the CT system is the ionization state of the targeting C residue at physiological pH. In order to facilitate the appropriate hydrogen bonding, the amino group at position 3 of the C must be protonated. This presents no problem when the pH is low; however, at neutral pH, most of the pyrimidines are unprotonated. If the CT system is to be used at physiological pH, it may be preferable to employ 5-methylcytosine or 5-bromouracil in place of cytosine; as described for example by Povsic et al. [115]; and Lee et al. [116]. It may also be especially useful to enhance stability of the triple helix by employing a PENAM which comprises a group which will cross-link or intercalate into the target double helix.

In triple helix formation via the "GT" motif, guanine residues recognize G—C pairs, and thymine or adenine residues recognize A—T pairs, as described for example by Cooney et al. [117]. In the GT motif, the targeting oligomer is in an anti-parallel orientation vis-a-vis the target sequence.

Thus, via one or another sort of triple helix formation, a PENAM can be used to target a complementary sequence on one strand of a double-stranded target [118–137]. The efficiency of Hoogsteen binding can be further enhanced by a number of well-known techniques. For example, as discussed above, 5-methylcytosine or 5-bromouracil in the targeting sequence can be used to enhance binding to complementary G residues in the target sequence. Other approaches to alter the biologic effects of triple helix formation include the introduction of modifying groups onto the targeting nucleic acid or PENAM, such as intercalating or crosslinking groups. For example, an acridine derivative can be introduced onto an end of a targeting sequence to enhance triple helix stability. These and other modifications are further described in Matteucci and Bischofberger and citations therein [2].

Variations of Basic PENAM to Modify Target

As discussed herein, a variety of functional groups can be introduced into the basic PENAM structure in order to further affect the interaction between the PENAM and its target nucleic acid, and/or to affect the target nucleic acid itself. These reactive groups can be appended either at the N-terminus or at the C-terminus or at an intervening position. Examples of such reactive groups, discussed herein and in the art include labeling groups, intercalating groups, cleaving groups and other groups that reconform or bind to nucleic acids or modify the target nucleic acid [3, 9].

One type of modifying group that can be introduced into a PENAM is a nucleic acid intercalating group. A number of such intercalating groups are known in the art, many of which are acridine derivatives [138–148].

Another type of modifying group is a cross linking group. Cross linking can be used to stabilize the interaction between a PENAM and its target, which may be especially useful in achieving and stabilizing triple helix formation. Various approaches to the stabilization of triple helix formation include photochemical crosslinking as described by Le Doan et al. [149] and Praseuth et al. [150], and alkylation of the N7 of specific guanines in the target duplex as described by Vlassov [151] and Fedorova et al. [152].

Crosslinking can also be used to covalently link a new molecular structure, attached to the PENAM, to a particular location within a nucleic acid target. Thus, for example, a label attached to a PENAM could be linked to the particular location targeted by the PENAM. Such labels could be photo-induced cross-linking agents, for example psoralen, coumarin, ellipticine and their derivatives [153–160].

Other labels might not involve a cross-linking group. A number of such labeling groups are known in the art [161–166]. The ability to label particular sequences in a nucleic acid will also be useful in efforts to map and sequence various genomes.

Another type of modifying group that can be introduced into the PENAMs of the present invention are nucleic acid alkylating agents. A number of such alkylating groups are known in the art. For example these include N-mustards as reactive alkylating compounds [167–177], porphyrins [161, 178], psoralens as photochemical activatable agents [158, 179] and quinones as inducible alkylating agents [180].

Another type of modifying group that can be introduced into the PENAMs of the present invention are nucleic acid cleaving groups. There are a number of cleaving groups that can be used to allow a PENAM to act as an artificial sequence-specific nuclease, which have been described in the art [125, 181–192]. The following approaches are intended as an illustrative, not an exhaustive, list of cleaving groups. In one approach, iron(III) EDTA is used as a cleaving group which generates free radicals under appropriate redox conditions as described by Moser et al. [114]. Other redox-activated transition metal cleaving groups include complexes of o-phenanthroline-Cu(I) introduced by Francois et al. [193, 194] and porphyrins-Fe(II) used by Le Doan et al. [195]. These systems may be more useful in vitro, where redox activation is more readily controlled. Another alternative is photochemical cleavage as described by Perrouault et al. [154]. Still another approach is to incorporate as a cleaving group a relatively non-specific nuclease such as DNase I or staphylococcal nuclease and effectively convert it into a specific endonuclease by conjugation to the sequence-specific PENAM, analogous to the work reported by Schultz et al. involving ODNs [196–198]. Yet another possible approach to cleaving target nucleic acids is to incorporate a ribozyme into the PENAM [199–201].

Depending on the particular modifying groups selected, these groups can be incorporated into the PENAM at virtually any position, including positions within and outside of the NuAA monomers. However, there are a number of general considerations that should guide selection of a particular group and location. The most significant consideration is that the group should not be introduced into a position that is likely to prevent sufficient hydrogen bonding between the bases of the PENAM and those of the target nucleic acid. Thus, while small modifying groups can be accommodated within the NuAA monomers engaging in hydrogen bonding to the target, larger groups may be better accommodated outside of the hydrogen bonding monomers. Even large modifying groups such as nuclease enzymes can be attached to such terminal regions of the PENAMs [8]. In some cases, the nature of the interaction between the modifying group will dictate favorable positions in the PENAM. Moreover, molecular modelling can be used to anticipate favorable positions for the incorporation of such groups.

The binding affinity of candidate PENAMs can be readily tested using any of a variety of well-known techniques. These include, for example, standard melting temperature $(T_M)$ measurements [202–204]; as well as chemical, photochemical, physical and/or enzymatic probing [205–213]. Binding can also be effectively probed using "footprinting" techniques. Footprinting was primarily introduced by Galas and Schmitz [214] to detect contacts between DNA and DNA binding proteins. The basic idea behind this methodology is to allow a protein to bind to radioactively-labelled DNA/RNA containing the sequence that is recognized by the protein. After the binding event, the protein-DNA complex is subjected to nuclease digestion, usually using DNAse I. The regions of the DNA molecule covered by the protein are protected from the digestion while the rest of the DNA backbone is digested. The products of this cleavage produce blank regions or "footprints" at the sequence where the protein was bound to the DNA sequence (as visualized on autoradiographs of electrophoretic gels such as those used for DNA sequencing). Thus, by comparision with a DNA sequence marker, one can identify the sequence specificity of a particular DNA binding moiety. Various chemical reagents have been developed to enhance fingerprinting analyses. Among them, reagent systems consisting of $[Fe(EDTA)^2]$, hydrogen peroxide and sodium ascorbate [215–217] and gamma rays [218] are noteworthy. Numerous examples of this technique to study the sequence-specificity of nucleic acids by oligonucleotides are known in the art [128, 148, 219–221].

UTILITY AND ADMINISTRATION

Diagnostic/Analytical/Preparative Applications:

The peptide-based nucleic acid mimics (PENAMs) of the present invention are substantially homomorphic with nucleic acids. This homomorphism facilitates hydrogen bonding and thus hybridization with target nucleic acid sequences.

Diagnostic, analytical and/or preparative uses of PENAMs include the use of PENAMs as "reporter" molecules; use of PENAMs for the capture of complementary DNA/RNA sequences. For example, the PENAMs can be used as hybridization probes to identify target sequences in a particular DNA or RNA of interest [222–233].

Use as a Reporter

Generally, for diagnostic applications, the PENAMs will comprise a labeling or "reporter" group (as described herein) by which the interaction with the proper target sequence can be detected [234–242]. A typical example of such an application would involve a pool of single-stranded polynucleotides (the sample or "analyte" which might contain a target sequence such as a viral nucleic acid). In a typical probe approach, this pool of polynucleotides will be bound to a solid support. A labeled PENAM is then introduced to the polynucleotides under hybridizing conditions and allowed to anneal. After washing away non-hybridized PENAM, the sample bound to the solid support is analyzed for the presence of the labeling group. Such assays can be carried out according to standard hybridization procedures suitable for the degree of complementarity expected. That is, high stringency hybridization can be used for high levels of complementarity (e.g. greater than 90%), lower levels of stringency for lower levels of hybridization, as is well-known in the art. However, given the reduced charge repulsion between PENAMs and nucleic acids, and also the possibility of introducing intercalating or cross-linking groups into the PENAMs, it will be possible to design PENAM probes that can be subjected to even more stringent hybridization conditions (e.g., higher temperature, lower salt) than the corresponding native complementary strand. The ability to use more stringent conditions will reduce the background "noise" caused by non-specific or mismatched binding and, as a result, will reduce the incidence of false-positive results. For a given PENAM and target, the optimum hybridization conditions can be determined by testing the PENAM under varying conditions (particularly the concentration of denaturants, the temperature during hybridization and washing, and the concentration of salts during washing) with both positive and negative controls (known amounts of target sequence decreasing to zero).

Use for Capture

In another type of diagnostic/analytical/preparative application, the PENAMs can be linked to a solid support for capture of complementary (target) nucleic acids to the support [243–245]. In such systems, the PENAMs can also be synthesized directly onto the solid support. The presence of target nucleic acid bound to the solid support via the PENAM can be detected, for example, by using a polycationic molecule which would bind to the negatively charged backbone of the target nucleic acid (but not the peptidic backbone of the PENAM). The polycationic molecule can comprise a labeling group to produce a signal by which the bound complex can be detected. The PENAMs of the present invention can also be employed in the variety of sandwich hybridization assays which are known in the art. As discussed above, one advantage of using PENAMs is the ability to run the assays under more stringent hybridization conditions.

The use of PENAMs as capture probes can also be applied to preparative techniques in which the PENAM, typically bound to some support, is used to attract and thereby retrieve a complementary target nucleic acid using methods analogous to those described for the diagnostic assays above.

Therapeutic Applications:
Antisense and/or Antigene Modulation

The PENAMs of the present invention are also useful, as described herein, for modulating the activity of nucleic acids in an antisense manner. The ability to modulate nucleic acid activity by antisense regulation is well known in the art as described [5, 8, 121, 246–250]. With respect to the control of gene expression, PENAMs can be used not only to inhibit expression but also to activate it in vitro as well as in vivo. Indirect activation of gene expression can be accomplished, for example, by suppressing the biosynthesis of a natural repressor, as described for antisense ODNs by Inoue [251]. Direct activation of gene expression can be accomplished, for example, by reducing termination of transcription as described for antisense ODNs by Winkler et al. [252]. There are several in vitro as well as in vivo test systems known in the art that have been routinely used [95–97, 101, 109, 253–265]. The efficacy of PENAMs as antisense or antigene chemotherapeutics can be easily tested and compared using these test systems The ultimate targets of antisense modulation include viral diseases, bacterial diseases, inborn errors of metabolism, malignant cell growth, and any other conditions associated with the presence of a characteristic DNA or RNA or products thereof [7, 266–270].

Preparation/Administration

Depending on the nature and location of the target nucleic acid, there are a number of different techniques that can be used for promoting contact between a PENAM and its target. For example, where the target nucleic acid is in solution in vitro, the PENAM can simply be added to the solution and the mixture incubated under standard conditions favoring nucleic acid hybridization. Where the target is intracellular, the PENAM must be capable of passing through one or more cellular membrane systems in order to contact the target nucleic. In this regard, the PENAMs of the present invention are already substantially more effective than nucleic acid based targeting molecules such as anti-sense oligodeoxynucleotides (ODNs). In particular, the passage of ODNs through cellular membranes is very inefficient because of their highly-charged backbone. In the case of PENAMs, the bases are attached to a peptidic backbone which is far less charged at physiological pH. If desired, the permeability of PENAMs can be further enhanced by incorporation of additional modifications. A number of such modifications are known in the art and have been described in detail earlier [2, 4]. These modifications include, for example, the attachment of hydrophobic chains to the targeting molecule [271, 272]. Another approach involves the attachment of polylysine [105], however, polylysine may not be applicable in all cell systems [4]. Another non-specific carrier which can be used to improve uptake is cholesterol and its derivatives [102, 273, 274].

Another approach is to utilize receptor-mediated endocytosis to enhance and/or to direct cellular delivery [2, 4]. In this approach, cells with receptors for a particular ligand can be targeted by linking the ligand to the PENAM. By way of example, linking biotin, folate, transferrin or interleukin-1-β(IL-1B) to a PENAM of interest, one can specifically and efficiently target cells expressing biotin, folate, transferrin or IL-1B receptors. For situations in which the receptor status of a cell type is unknown, or where a receptor-ligand pair is known but the ligand cannot be suitably linked to the PENAM, it may also be possible to use more generalized ligands such as lectins (sugar-binding proteins) since most cells are believed to have glycoproteins on their surface. Such a generalized approach may also be useful where targeting a broad range of cellular types is desired. Analogous approaches can be used to target nucleic acids within a cellular organelle. For example, linking a mitochondrial protein to a PENAM can be used to target the PENAM to mitochondria as has been described for incorporating double-stranded DNA into mitochondria [4]. Of course, such receptor-mediated delivery systems may utilize any of a large number of other known cellular receptor systems.

Still another approach is to deliver the PENAMs to target cells using liposomes [98] or antibody targeted "immunoliposomes" [2]. Linking of acridine or benzophenanthridine to the PENAM can be used to improve incorporation into neutral liposomes [4].

The PENAMs are thus useful in therapeutic, diagnostic and research contexts. PENAMs can be administered in the same manner as modified ODNs, which manner of application is conventional in the art. In therapeutic applications, the PENAMs are utilized in a manner appropriate for antisense therapy in general. For such therapy, the PENAMs can be formulated for a variety of modes of administration, including systemic and topical or localized administration. Techniques and formulations may be found, for example, in *Remington's Pharmaceutical Sciences*, Mack Publishing Co., Easton, Pa. (latest edition). The PENAM active ingredient is generally combined with a carrier such as a diluent or excipient which may include, for example, fillers, extenders, wetting agents, disintegrants, surface-active agents, or lubricants, depending on the nature of the mode of administration and the dosage forms. Typical dosage forms include tablets, powders, granules, capsules, suppositories, liquid preparations such as suspensions, emulsions and solutions, and liquid preparations for injections, including liposome preparations. For systemic administration, injection is preferred, including intramuscular, intravenous, intraperitoneal, and subcutaneous. For injection, the PENAMs of the invention are formulated in liquid solutions, preferably in physiologically compatible buffers such as Hank's solution or Ringer's solution. In addition, the PENAMs may be formulated in solid form and redissolved or suspended immediately prior to use. Lyophilized forms are also included. Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example. For oral administration, the PENAMs are formulated into conventional oral administration forms such as tablets, capsules and tonics. For topical administration, the PENAMs of the invention are formulated into ointments, salves, gels or creams, as is generally known in the art.

The PENAMs of the present invention will, by virtue of their unusual structural features, be resistant to the degradative enzymes that are expected to be present in most biological systems. Thus, the PENAMs do not possess the phosphodiester backbone which is the standard target of the nucleases. Also, the peptidic backbone is unlike that of naturally-occurring peptides because of the presence of both D- and L- residues. This basic resistance to degradative enzymes can be further enhanced, if desired, by the addition of protecting groups which interfere with the ability of a degradative enzyme to modify the oligomer.

EXAMPLES

The following examples are intended to illustrate, not to limit, the invention.

General procedures

Unless otherwise noted, the following general procedures were employed in conducting the experiments subsequently described:

All moisture-sensitive chemical reactions, requiring inert atmosphere, were carried out under nitrogen or argon in oven- or flame-dried glassware using septum technique. All chemicals and solvents were of technical or reagent grade and used as received unless otherwise stated. Thin layer chromatography (tlc) was carried out on pre-coated 0.25 mm layer thickness silica gel and/or alumina plates, supplied by Analtech Co. Preparative thin layer plates were coated with 1.5 mm layer thickness silica gel GF-254 (60 mesh, ASTM). Flash column chromatography was carried out using 70–230 mesh silica gel, supplied by E. Merck. Melting points were taken on an electrothermal apparatus and are uncorrected. Infrared spectra were recorded on a Nicolet FT-IR spectrophotometer with samples prepared as potassium bromide pellets or as thin films on NaCl plates. Ultraviolet spectra were recorded in quartz cuvettes on Hewlett Packard UV/VIS spectrophotometer. NMR spectra were recorded on GE 300 MHz or GE 500 MHz spectrometers using deuterated solvents and tetramethylsilane as an internal standard. Mass spectra were recorded at UCSF Mass Spectrometry center. Optical rotations were measured in a 1-dm quartz cell at 22–23 degrees Celsius at the sodium D line on a Perkin-Elmer polarimeter (Model 241 MC). Solid Phase Peptide Synthesis was carried out on an Applied Biosystems Peptide synthesizer (model 431A), using Boc-strategy. Hydrogen fluoride setup was used to cleave the peptides from the resin. The peptides were purified either by HPLC using C18 reverse phase Vydac® column or by FPLC using cation exchange Mono S® column.

Example 1

Basic molecular comparison of PENAMs of the present invention with standard ODNs and with PENAMs that do not contain centers of varying chirality As shown in FIG. 1, the chimeric PENAMs of the present invention are structurally quite distinct from standard oligonucleotides (ODNs). It is by virtue of these differences that PENAMs avoid a number of technical difficulties associated with the transport and stability of ODNs. Functionally, however, the PENAMs are analogous to ODNs in their ability to engage in sequence-specific hydrogen bonding to complementary nucleic acids by virtue of their nucleotidic sidechains being properly "presented" by the peptidic backbone. Molecular modelling has been used to analyze and confirm these structural and conformational relationships.

Design and model building computations were performed on a Silicon Graphics (Mountain View, Calif.) IRIS workstation [275] using the SYBYL® molecular modelling package (v.5.4/6.0), offered by Tripos Associates [276]. There are several ways to generate or build these models. As an illustration, the following approach has been used to build comparative models Firstly, to illustrate the substantial structural differences between the PENAMs of the present invention and standard ODNs, molecular modelling was used to show the steps required to "convert" DNA into a PENAM. The SYBYL DNA sequence builder was used to generate the complementary double stranded DNA decamer, $dT_{10} \cdot dA_{10}$, into B-DNA conformation, based on the crystal structure, solved by Arnott et al. [277]. The purine strand ($dA_{10}$) of the generated DNA decamer, $dT_{10} \cdot dA_{10}$ was then used as a template to construct examples of the PENAMs: Version I (without varying chiral centers) and Version II (with alternating chiral centers).

First, the oxygen atoms (O4') of the ribose rings, along with the C4'—O4' and O4'—C1' bonds, were deleted. Then, all of the O3' oxygen atoms and C4' carbon atoms were substituted by carbonyl (C=C) groups and amide nitrogens (N), respectively. Next, the C5' carbons, the O5' oxygens and the remaining phosphate backbone (O—P=O) were deleted. Next, trans-amide bonds were made between the amide nitrogen (N4') of each monomer and the carbonyl (C=O3') of the next monomer. Appropriate hydrogen atoms were added on all of the modified atoms (C1', N4') to satisfy their hybridization states. Having effectively transformed the sugar-phosphate backbone into a peptidic backbone, the side chains were then substituted with the nucleic bases (adenine in this illustration), to generate a chimeric peptide-based nucleic acid mimic.

In order to compare the homomorphism of PENAMs with and without varying chiral centers, two different versions of the previously described PENAM were constructed. In PENAM Version I (without varying chirality), all of the alpha carbons (C2) were assigned the L-configuration as in the "natural" L-amino acids. PENAM Version I was then energy minimized as a single strand, in beta-sheet-like extended conformation, using force field parameters offered by SYBYL software package.

In PENAM Version II, all alpha carbons (C2) of odd numbered residues were assigned the L-configuration as in "natural" amino acids, and all alpha carbons (C2) of even numbered residues were assigned the D-configuration as in "unnatural" D-amino acids. PENAM Version II was then energy minimized as a single strand, in beta-sheet-like extended conformation, using force field parameters offered by the SYBYL software package.

Figure 2A:
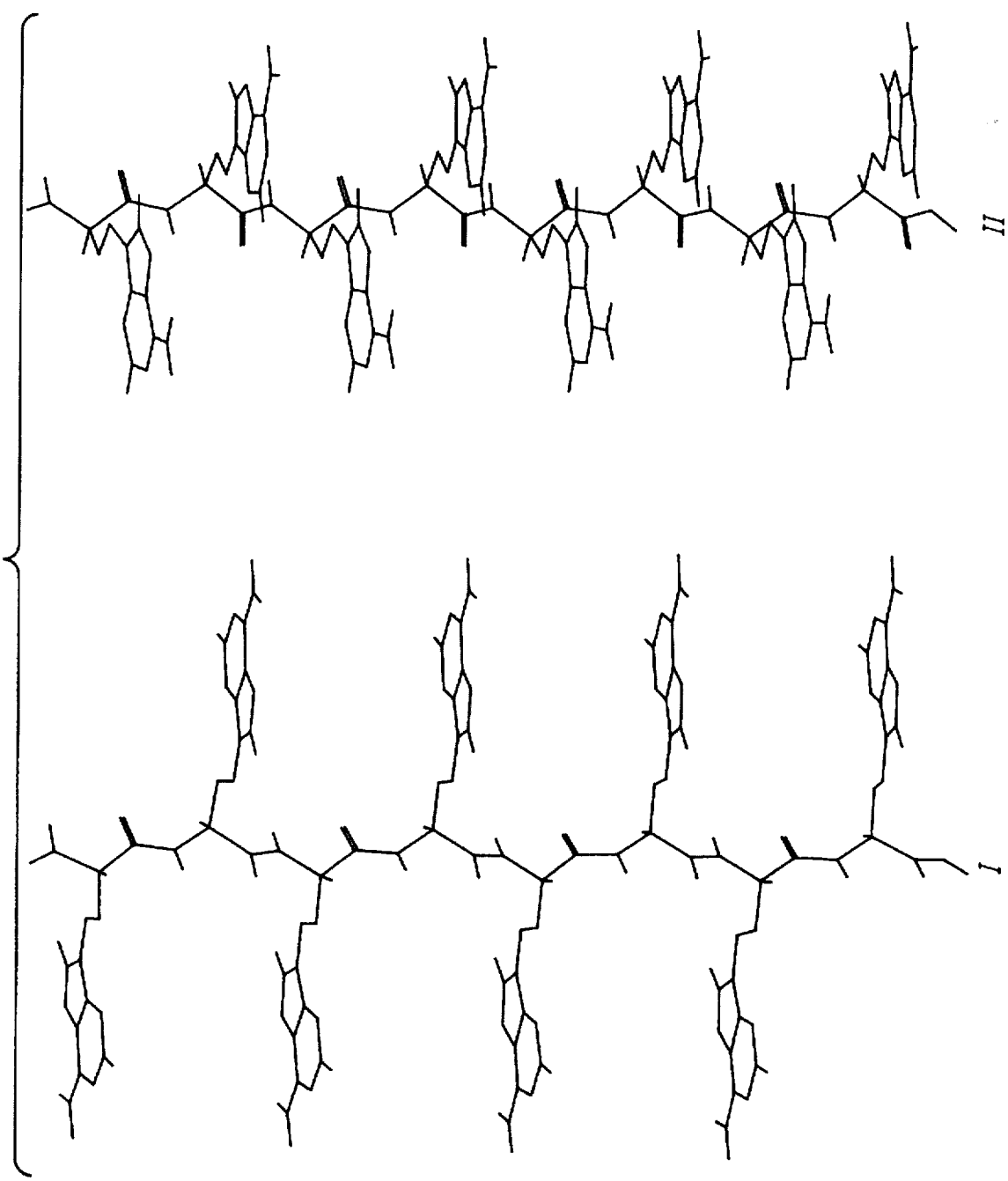
FIG. 2(a and b) is an illustrative example of molecular modelling of an (L)-PENAM (Version I, constructed from L-NuAA monomers) and a (D/L)-PENAM (Version II, constructed from alternating D- and L-NuAA monomers), shown in beta-sheet conformation in both a "side view" (FIG. 2a) and a "top view" (FIG. 2b).
Figure 2B:
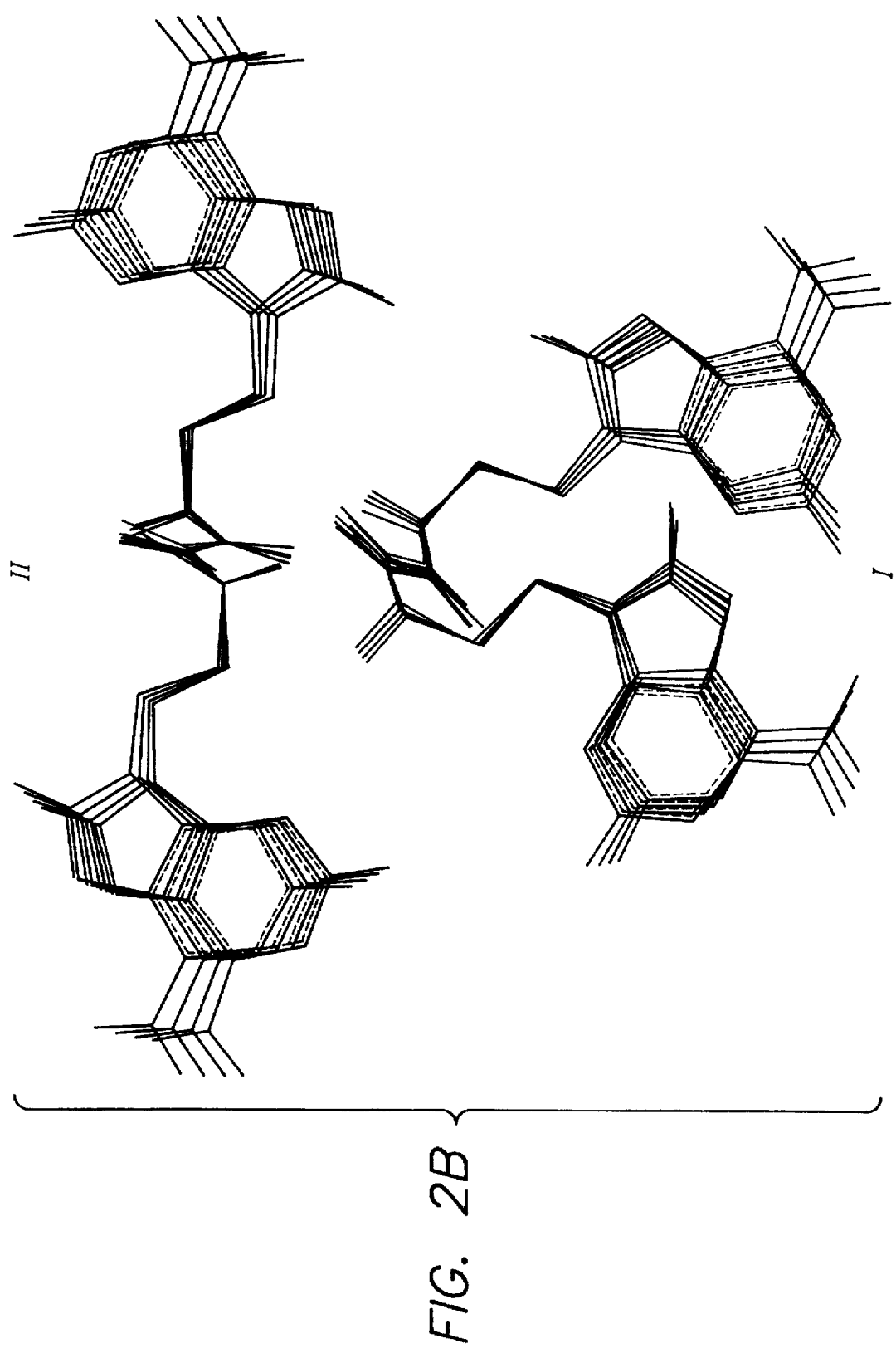
Figure 3A:
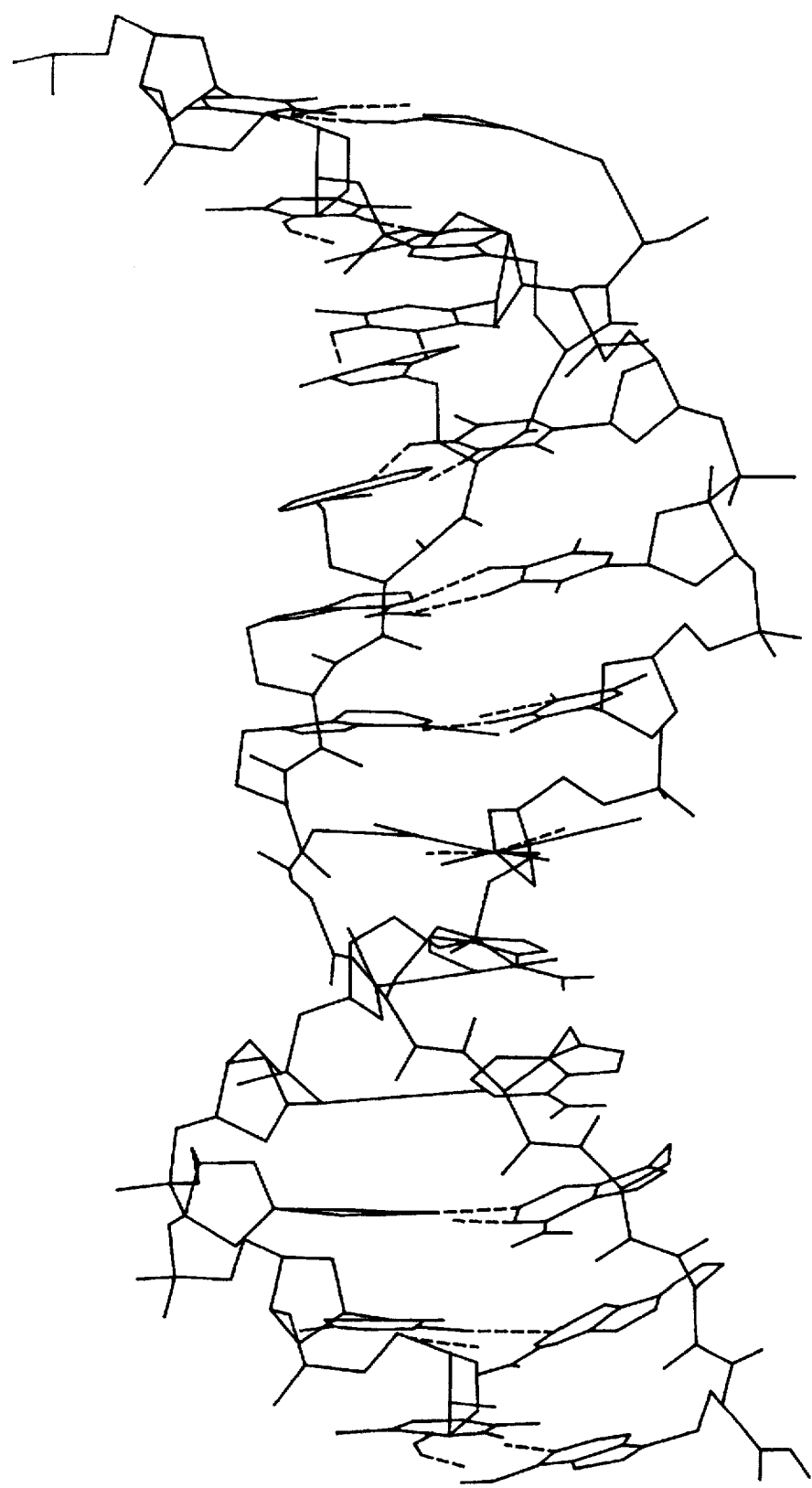
FIG. 3(a–e) is an illustrative example of molecular modelling comparisons of various PENAMs (differing in the length of their "S2" spacer group), each bound to a complementary strand of target DNA. The S2 spacer group positions are occupied by bonds (FIG. 3a), methylene groups (FIG. 3b), ethylene groups (FIG. 3c), or propylene groups (FIG. 3d); as described in Example 2 below.
FIG. 3e is a corresponding model illustrating the interaction between two complementary DNA strands.
Figure 3B:
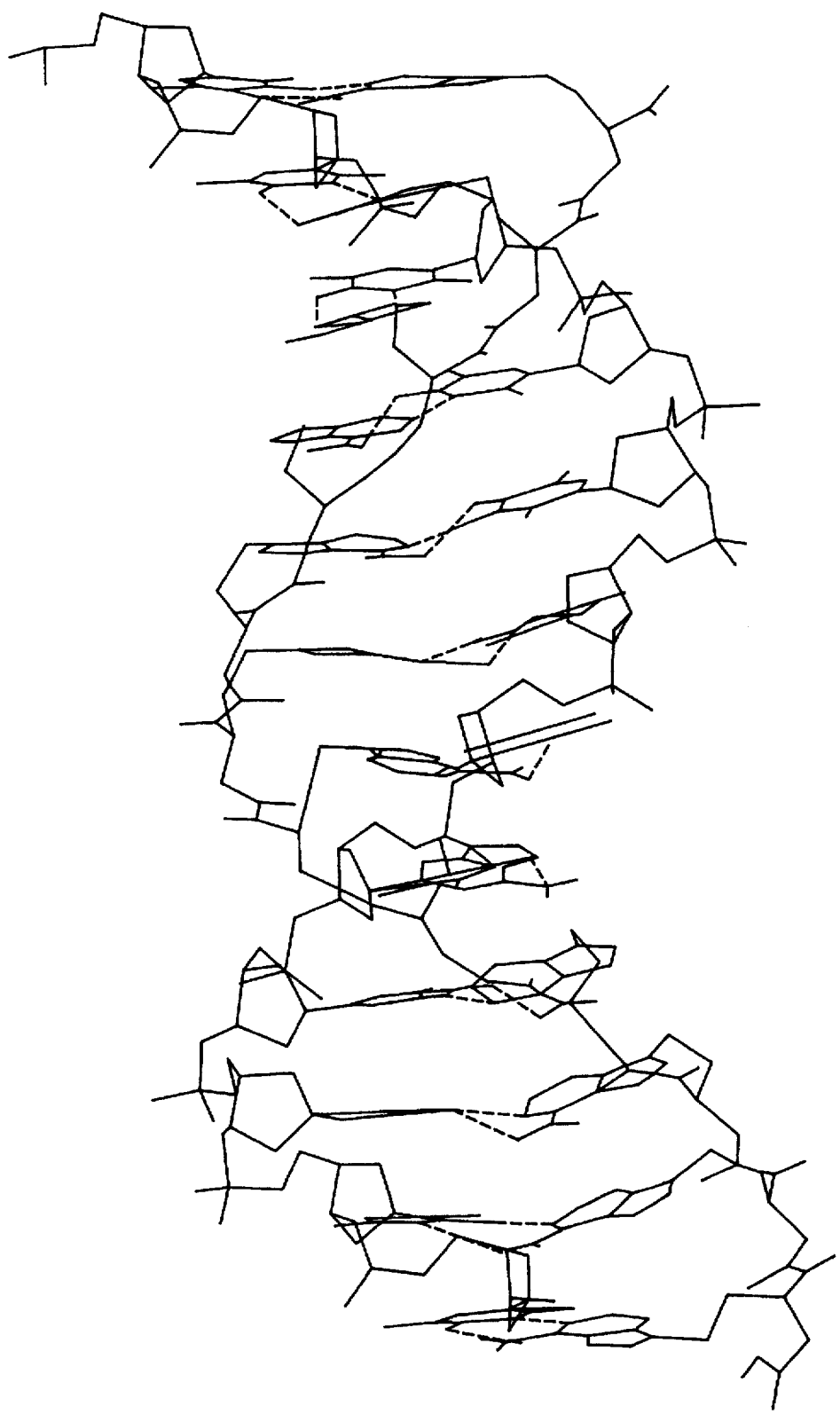
Figure 3C:
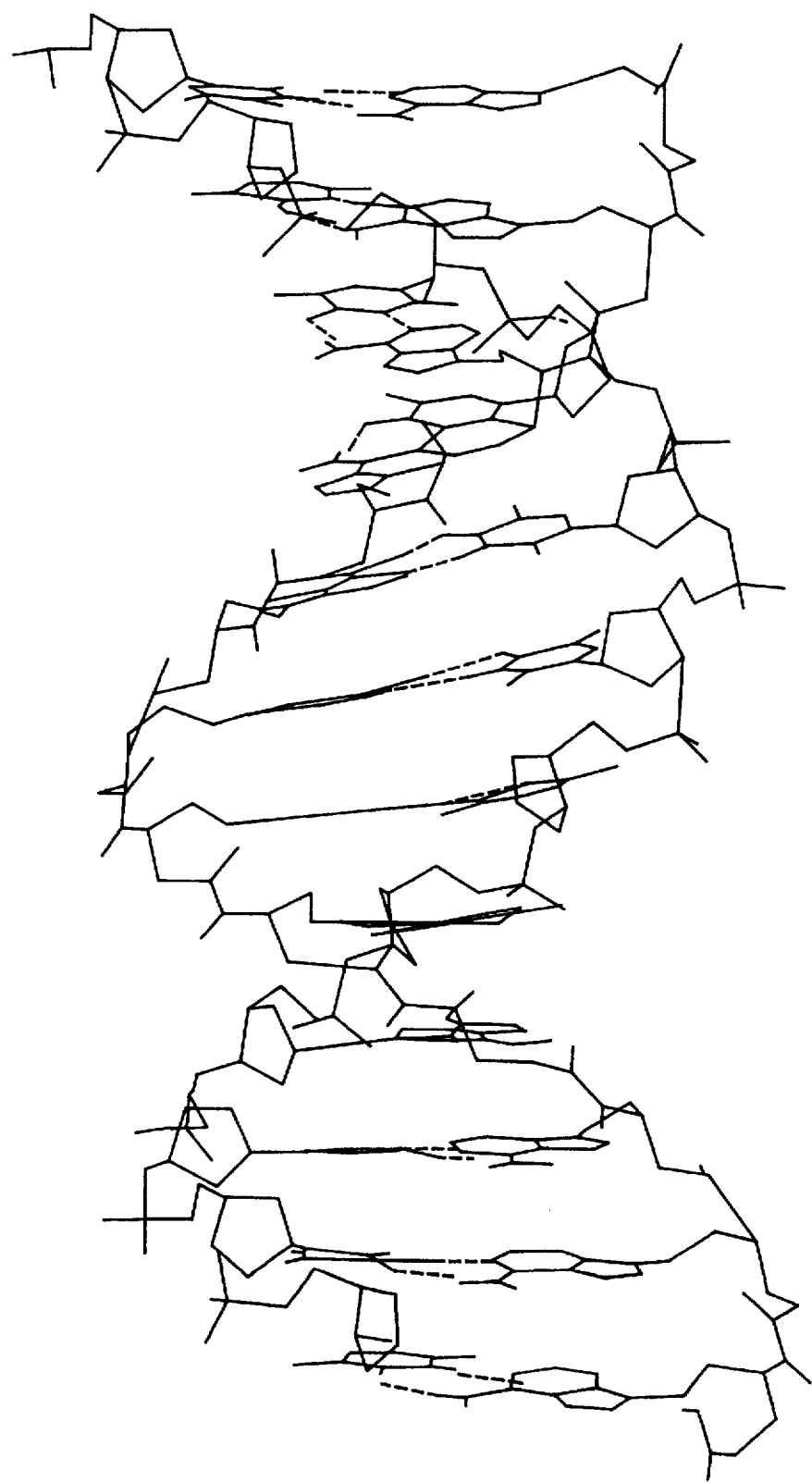
Figure 3D:
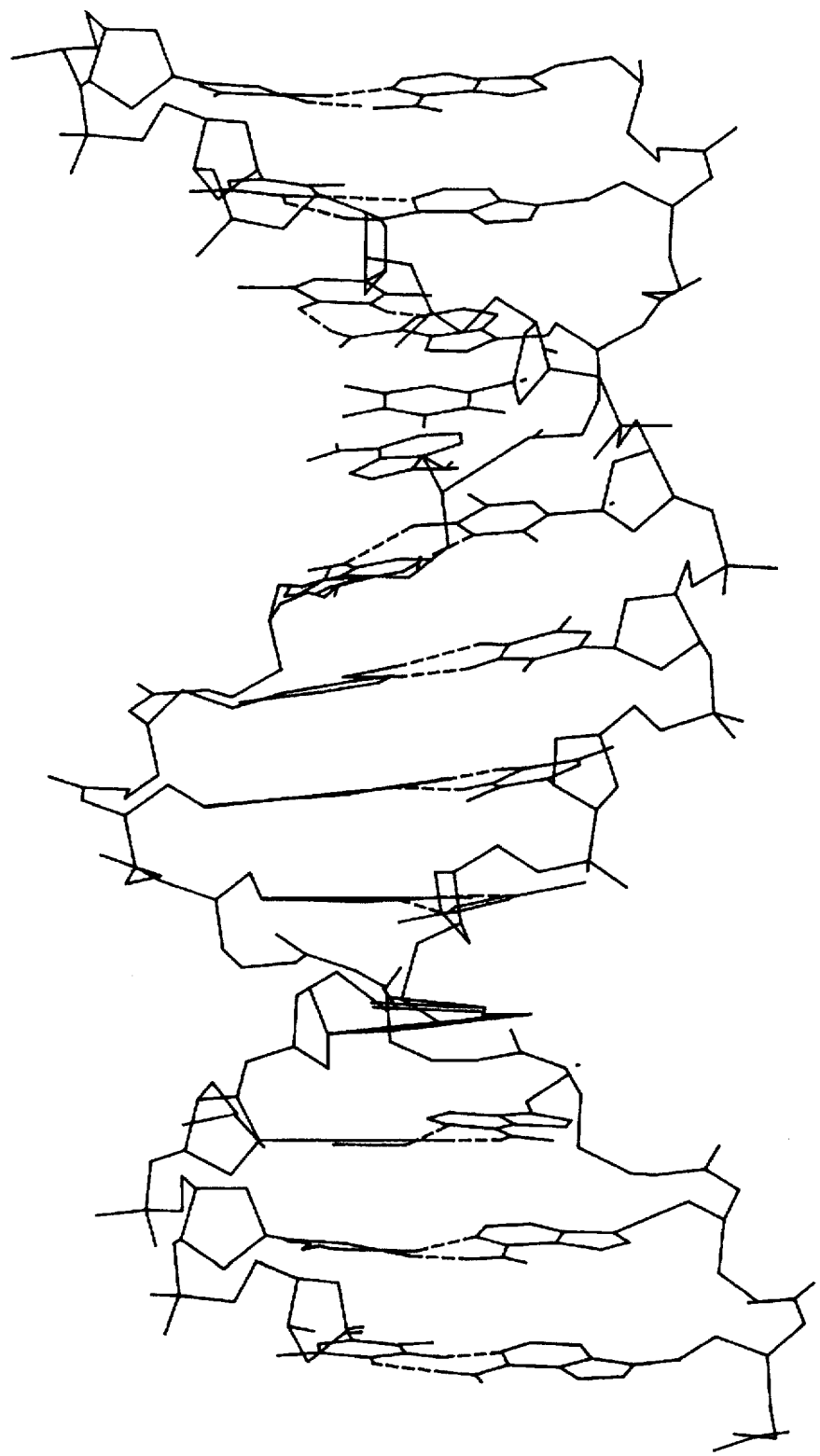
Figure 3E:
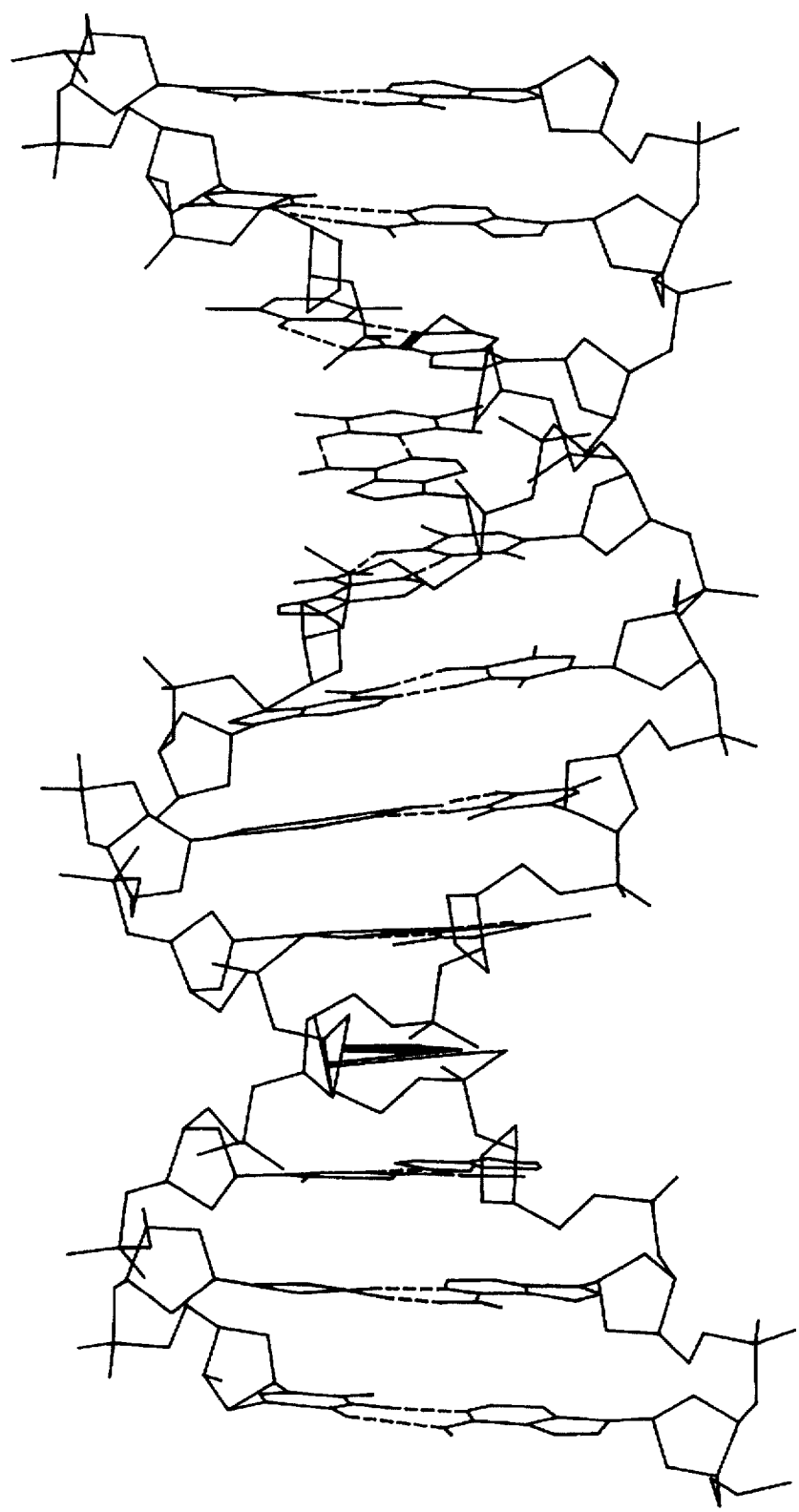

As discussed above, it is believed that for optimal binding the PENAM should have a conformation in which the nucleotidic bases are stacked approximately at the 3.5 Angstrom interval and are oriented away from the backbone in such a manner that the hydrogen bond donors and acceptors of the nucleotidic bases can directly "read" the complementary bases on the target nucleic acids by specific hydrogen bonding interactions. The differences can be visualized most readily when the PENAMs are viewed in beta-sheet-like extended conformation. FIG. 2a presents a "side view" illustration of the two versions. The differences in estimated orientation are even more striking when viewed from the "top" (i.e. along the length of the polymer) as illustrated in FIG. 2b. In particular, in Version I, the adenine moieties in the side chains were approximately 180° apart on the alpha carbons of each pair of adjacent monomers and, as a result, the adenine moieties could not be effectively stacked or aligned at the interval of 3.5 Angstrom spatial distance. In contrast, in PENAM Version II, the adenine moieties were much closer to each other in space (at an angle of approximately 65°) and could therefore be stacked at a spatial distance of approximately 3.7 Angstrom, which substantially enhances their ability to hybridize with a target nucleic acid.

Similar molecular models were constructed using other nucleic bases (e.g., B=thymine, guanine, cytosine, uracil), and confirmed the preceding results.

Example 2

Use of molecular modelling to predict homomorphism between PENAMs of the present invention and target DNA As an illustration of the use of molecular modelling to assess the likely homomorphism between a particular version of the PENAMs and a target nucleic acid, we used the molecular modelling techniques referred to in Example 1 to assess several types of PENAMs having varying spacer groups. In particular, we examined models of a single strand of DNA (a thymine 12-mer) in association with complementary PENAMs having NuAA monomers of the following formula:

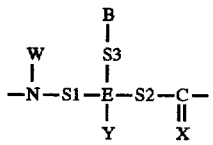

in which E is carbon; W is hydrogen; Y is hydrogen; S1 is a bond; S3 is an ethylene group; X is oxygen; B is adenine; N is nitrogen; and wherein S2 was selected from the group consisting of a bond, a methylene group, an ethylene group and a propylene group.

Energy minimization (100 cycles) was performed using Tripos force field parameters provided in the Sybyl software package. Following the teachings of the present invention, the energy minimization was carried out in a manner that allowed for the introduction of varying chiral centers in the peptidic backbone of the PENAM such that the overall energy state of the molecule was minimized.

The resulting energy-minimized models are shown in FIG. 3(a–d). Although all of the models exhibited the formation of double helices between the PENAM and the target DNA, the modelling predicted an increasing homomorphism (which appears as an increasingly regular helicity) when the S2 spacer group was increased in length from a bond (FIG. 3a), to a methylene group (FIG. 3b), to an ethylene group (FIG. 3c), and finally to a propylene group (FIG. 3d). The corresponding model for an interaction between two complementary strands of DNA is shown in FIG. 3e. While the increase from methylene to ethylene to propylene is believed to be advantageous, further increasing the length of the S2 group (beyond that of a three-atom bridge as in propylene) is believed to be less advantageous.

Additional estimates of the relative homomorphism were obtained by assessing the total energy for the resulting molecules. The total energy was estimated as a sum of bond stretching energy, angle bending energy, torsional energy, out of plane bending energy and van der Waals energy, using the same molecular modelling software. Consistent with the apparently enhanced helicity, as described above, the resulting total energy estimates revealed a considerable decrease in total energy (suggesting an increase in homomorphism) when the length of the S2 spacer group was increased from 0 (in the case of a bond), to 1 (methylene), to 2 (ethylene), to 3 (propylene).

In all cases, the energy-minimized structures incorporated D-chiral centers into the peptidic backbone. For example, for the particular PENAMs modeled in this illustration, the following D-containing sequences were obtained after 100 cycles of energy minimization: DLLLDDDDDLL in FIG. 3a; LDDDDDDDDDDD in FIG. 3b; DDDDDDDDDDDD in FIG. 3c; and DDDDDDDDDDDD in FIG. 3d. These modeling data, as well as physical data involving PENAMs with alternating D- and L-chiral centers described below, suggest that the ability to incorporate D-chiral centers into the PENAM can be used to substantially enhance the homomorphism between particular PENAMs and their target nucleic acids.

Example 3

Use of retrosynthesis and molecular modelling to identify synthetic schemes for the preparation of NuAA monomers The NuAA monomers of the present invention can be synthesized from available starting compounds, such as amino acids, via a number of different synthetic pathways. As described herein, the preferred NuAA monomers contain a nucleic base that is substituted on the side chain at a distance which is similar to that between the nucleic base and the sugar-phosphate backbone in standard ODNs. Molecular modelling and retrosynthesis techniques have been used to identify conveniently-prepared intermediates and corresponding synthetic steps for the production of NuAA monomers of the present invention. An example of such a retrosynthetic analysis has been illustrated in FIG. 4a, as is described in more detail below.

We have used these techniques to develop a convergent modular synthetic approach for the synthesis of these stereo-specific PENAMs via NuAA monomers. This strategy includes a basic set of chemical building blocks of the structural units which allow for the synthesis of a diverse class of novel chemotherapeutic agents in an efficient and cost effective manner. The chemistry involved in the synthesis of these key intermediates is fairly easy, extensively studied and is well established in the literature [63–65, 278, 279]. As described herein, the preferred building blocks include: (i) NuAA monomers and their derivatives; (ii) amino acids (AA) and their derivatives; and (iii) Exampo acids and their derivatives.

Example 4

Figure 4A:
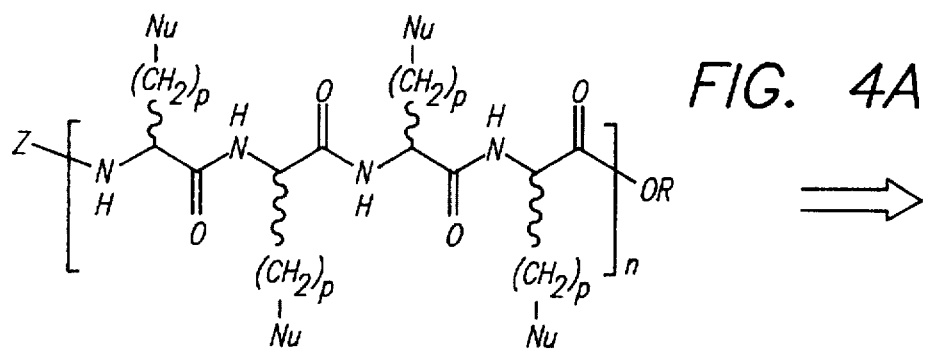
Figure 4A:
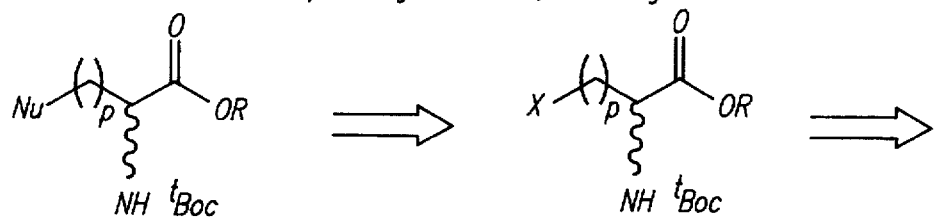
Figure 4A:
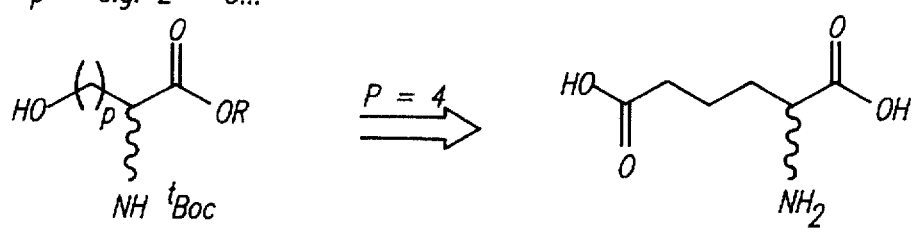
Figure 4A:
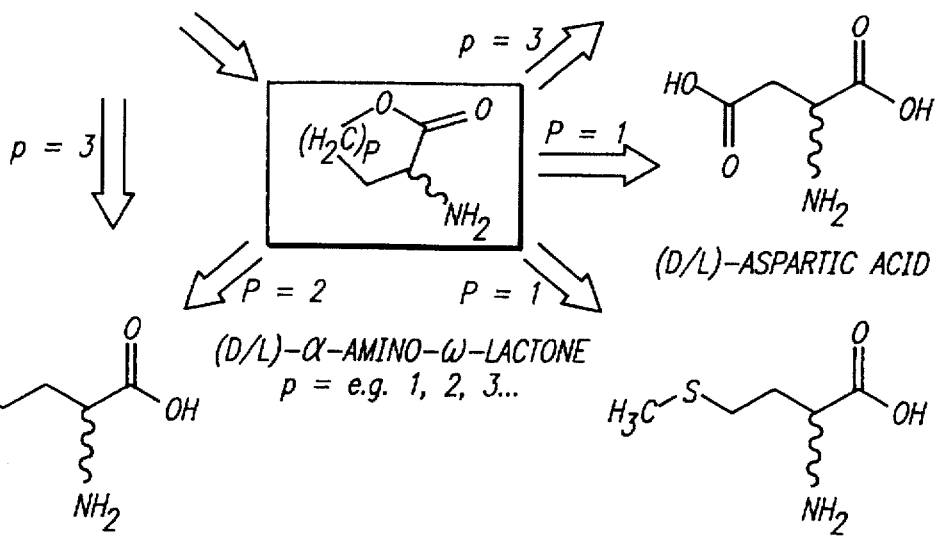

Use of α-amino-α-carboxylic acids as substrates for the preparation of NuAA Monomers As defined earlier, NuAA monomers are amino acids that have purine/pyrimidine nucleic bases or their heterocyclic analogs substituted in the aminoacyl side chain depending from the alpha carbon. These key intermediates can have L- or D-configurations at the alpha carbon (except for the aza-NuAA monomers, in which case the α-carbon is replaced by nitrogen, as described herein). The distance between the nucleic base and the peptidic backbone can be easily manipulated by varying the length of the side chain of these nucleicamino acids, i.e., the S3 position in the formula of the NuAA monomer. Molecular modelling has been used to show that, in order to mimic the homomorphism of native nucleic acids, the nucleic base is preferably sustituted on the side chain at least two carbon units distance from the peptidic backbone (e.g., γ-substituted), and is preferably not more than four carbon units away from the backbone. Thus, S3 is preferably a spacer group with a backbone of at least 2 atoms, preferably at least three atoms. Such NuAA monomers can be easily synthesized from commercially available starting materials, for example, natural alpha-amino acids (an illustrative example of the retrosynthesis of PENAMs and NuAA monomers from α-amino-α-carboxylic acids is shown in FIG. 4a). These natural amino acids provide a rich source of diverse chemical functionality, which are convenient for suitable chemical transformations using well-known synthetic techniques; and, in addition, they also serve as chiral templates by virtue of the chiral center generally present at the alpha-carbon. As discussed herein, the use of chiral monomers to introduce varying centers of chirality (or "antipodes") into the peptidic backbone allows for the production of PENAMs that are homomorphic to their target nucleic acids, allowing for efficient stacking and hydrogen bonding.

The purine/pyrimidine nucleic bases or their heterocyclic analogs can be introduced as aliphatic, acyl, amide or amine side chain substituents by chemical manipulations of these alpha-amino acids (as described herein). Especially convenient precursors for such manipulations are "omega"-halogenated (i.e. terminally halogenated) amino acids. Thus, as illustrated in FIG. 4a, NuAA monomers can be readily synthesized from ω-halogenated amino acids and any nucleic base. These ω-substituted haloamino acids can themselves be easily synthesized from commercially available natural amino acids, as described below.

Example 5

Preparation of haloamino acids (XAAs)

Based on the retrosynthetic analysis illustrated above, haloamino acids (XAAs) have been identified as convenient chemical building blocks in the synthesis of NuAA monomers. These haloamino acids are modified amino acids in which at least one of the hydrogens on the side chain carbons has been substituted by a halogen group (especially Cl, Br, I). The side chain distance can be readily varied by substituting the halogen group at, e.g., the β-, γ-, δ- or ω- carbon in the side chain. Subsequent nucleophilic substitution of the halogen group by a nucleic base gives ready access to a wide variety of NuAA monomers, which can then be used to prepare stereo specific α-amide linked PENAMs using synthetic techniques analogous to those described in, e.g., references [21–25]. The molecular modelling analyses discussed above suggested that NuAA monomers in which the nucleic base is either at γ (C3) or δ (C4) carbon atoms in the side chain are likely to position and orient the nucleic base at particularly effective distances from the peptidic backbone.

Although any halo derivative, including chloro-, bromo- or iodo-amino acids is suitable for synthesis of the NuAA monomers, bromo-derivatives were selected as an initial example because there are a number of well-known synthetic routes available for the preparation of brominated amino acids [278, 279]. Of those routes, the conversion of ω-hydroxyamino acids to corresponding ω-bromoamino acids appeared to be especially convenient. In particular, several brominating reagents such as hydrobromic acid, phosphorous tribromide, phosphorous pentabromide, thionyl bromide, methanesulfonybromide and carbon tetrabromide/tertiary organophosphine have been used effectively for the bromination of hydroxy compounds (primary and secondary hydroxyl groups) to bromides [278, 279]. The use of carbon tetrahalide-organophosphine is advantageous for converting primary hydroxyl groups to corresponding halides [280]. An illustrative retrosynthetic scheme is shown in FIG. 4b.

As will be appreciated by those of skill in the art, advantageous reagents are characterized by simplicity of experimental procedure, good yields, and relatively mild, essentially neutral reaction conditions. In addition, a number of these hydroxyamino acids are commercially available or can be easily prepared in large quantities from their corresponding dicarboxylic esters by reduction with common reducing agents [278, 284]. Accordingly, γ-brominated-α-aminobutyric acid (4-bromo-2-amino-butanoic acid) and its homologue, δ-brominated-α-amino-valeric acid (5-halo-2-amino-pentanoic acid) were identified as particularly convenient intermediates. By way of illustration, the preparation of 4-bromo-2-amino-butanoic acid is described below.

In addition to the halogenation of hydroxy compounds, halogenation of ω-lactones is another useful synthetic meth-

29 odology for the preparation of halogenated carboxylic acids and their derivatives [22–25, 279, 281, 282].

Example 6

Synthesis of 4-bromo-2-amino-butanoic acid

For use in the synthesis of NuAA monomers, we prepared enantiomerically pure 4-bromo-2-amino-butanoic acid as L-, D-, and racemic D/L- stereoisomers, suitably protected at their amino and carboxylic acid functional groups in order to facilitate their use in existing solution and solid phase peptide synthesis procedures. As described earlier, 4-bromo-2-amino-butanoic acid can be conveniently prepared from an optically active 4-hydroxy-2-amino-butanoic acid (homoserine) by carbon tetrabromide-triphenylphosphine. However, if the starting material homoserine is not appropriately protected at carboxyl and amino groups, then the chemical conversion can lead to a cyclized product (α-amino-γ-butyrolactone) instead of 4-bromo-2-amino-butanoic acid. In addition, protection of the e-amino and α-carboxyl groups of homoserine can be affected by its tendency to lactonize. This problem can be readily circumvented by using α-amino-γ-butyrolactone as the starting material. The racemic and L-isomer of 4-bromo-2-amino-butanoic acid have been prepared as hydrogen bromide salts in good yield and high optical purity from their corresponding α-amino-γ-butyrolactones by bromination with hydrogen bromide in acetic acid [281]. Although α-amino-γ-butyrolactone is readily available only as a racemate, α-amino-γ-butyrolactone can be synthesized in all stereoisomeric forms either from the corresponding homoserine (γ-hydroxy-α-amino-butanoic acids) or from the corresponding methionine [283]. Even though both D- and L-homoserine are commercially available, their costs currently make them less desirable as starting materials. Alternatively, D- and L- homoserine can be easily synthesized from readily available D- and L- aspartic acids, respectively. Reduction of the β-carboxyl group of appropriately protected D- and L- aspartic acid can provide corresponding protected homoserine derivatives in gram quantities [284], which in turn can be cyclized in the presence of mineral acid (hydrochloric acid) to yield the required lactones.

We used methionine instead of aspartic acid as the starting material for the synthesis of α-amino-γ-butyrolactone since the D/L-, D- and L-stereoisomers of methionine are readily available as inexpensive chiral amino acids and can be converted in one step to the corresponding D/L-, D-, and L-α-amino-γ-butyrolactones in high enantiomeric purity and in excellent yields [283].

All the three stereo isomers, D/L-, D-, and L-α-amino-γ-butyrolactones were synthesized in about 85% yield, by modifying the literature procedure of Natelson [283], as described below.

Example 7

Figure 5:
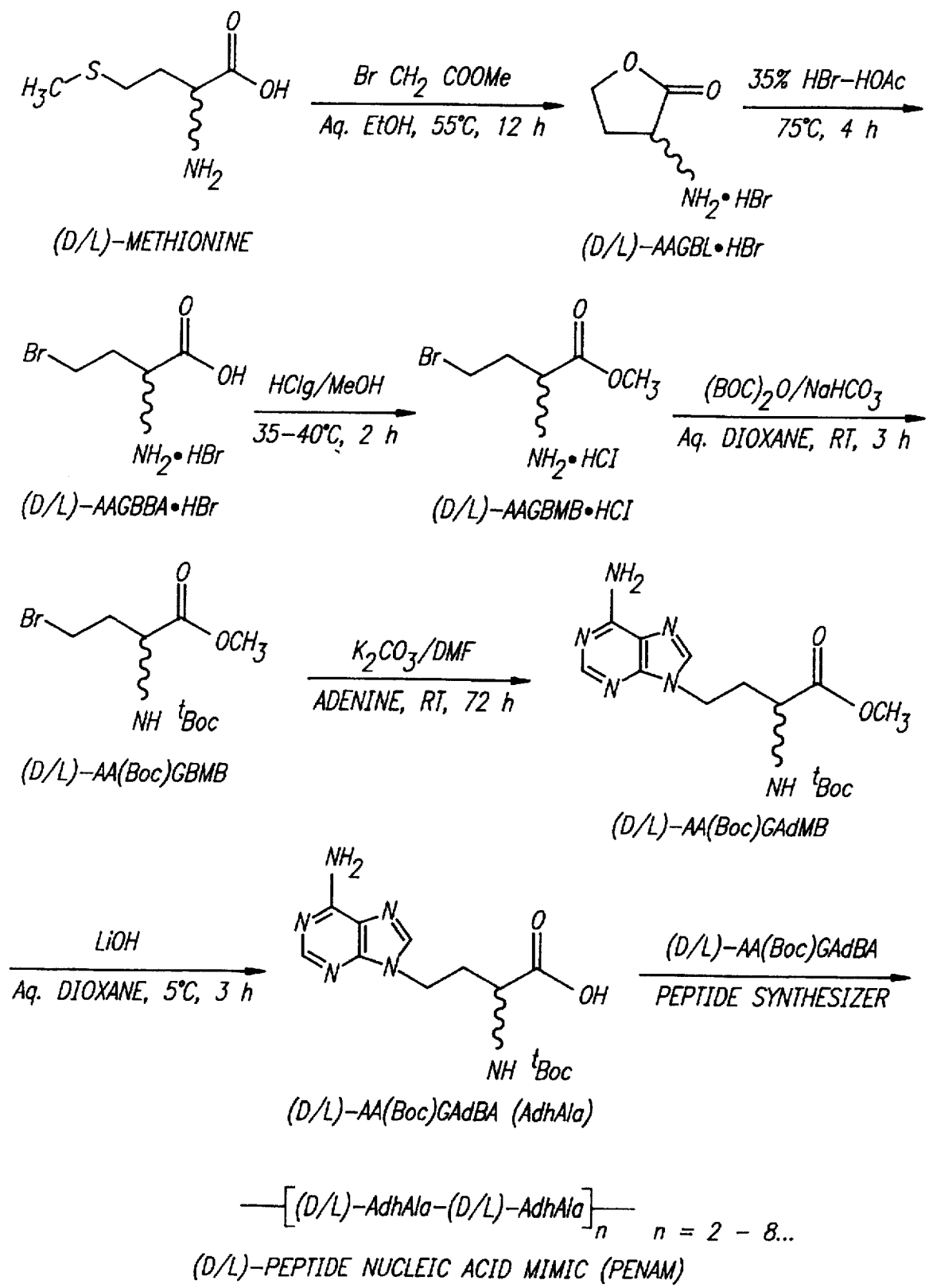
FIG. 5 is an illustrative example of the synthesis of a NuAA monomer and a PENAM starting from (D/L)-methionine.

Synthesis of the NuAA monomer 4-(N9-adeninyl)-2-(t-butyloxycarbonylamino)-butanoic acid As an illustration of the synthetic procedures, we synthesized D/L-, L- and D- stereo isomers of the NuAA monomer, 4-(N9-Adeninyl)-2-(t-butyloxycarbonylamino)-butyric acid [(D/L)-AA(Boc)GAdBA=AdhAla], in good yield and high optical purity (i.e., greater than 99%), using D/L-, L- and D- methionine as the chiral precursors, respectively. The synthetic procedure is illustrated in FIG. 5, showing the synthesis of racemic NuAA monomers [(D/L)-AA(Boc) GAdBA=AdhAla] using D/L-methionine as the starting material. The structures of the various intermediates were confirmed using standard techniques including $^1$H NMR, $^{13}$C NMR, specific rotation and mass spectrometry.

To summarize this illustrative synthetic procedure, D/L-methionine, on alkylation at the methylmercapto group with bromomethylacetic acid or its ester, formed corresponding sulfonium salts in situ, which on heating underwent nucleophilic attack by water to eliminate methanethiomethylacetate to give corresponding homoserine in situ. This homoserine on further heating at high temperature (>90° C.) cyclized to yield the known intermediate α-amino-γ-butyrolactone hydrobromide salt (AAGBL.HBr) in about 85–90% yield. By following the literature procedure [282], this lactone, on treatment with 35% HBr-HOAc at about 75 degrees Celsius, gave corresponding γ-bromoamino acid hydrobromide salt (AAGBBA.HBr). The α-amino group and the α-carboxylic group need to be protected to prevent them from reacting with the γ-bromo group and causing any side reactions during the subsequent synthesis. The α-carboxylic group of γ-bromoamino acid.HBr was protected as its methyl ester (AAGBMB.HCl) by passing dry HCl gas into a methanolic solution, while the α-amino group was protected as a carbamate by treating the methyl estere-.HCl with t-butyloxy carbonate in the presence of aqueous NaHCO$_3$ to yield 4-bromo-2-(t-butyloxycarbonylamino)-methylbutyrate, [AA(Boc)GBMB]. The NuAA monomer (D/L)-4-(N$^9$-adeninyl)-2-amino($^t$Boc)-butanoic acid [(D/L)-AA(Boc)GAdBA=AdhAla] was prepared essentially in accordance with these known synthetic procedures [21]. The reaction of this bromo carbamate [AA(Boc)GBMB] with adenine in the presence of dry potassium carbonate and DMF as a solvent gave approximately 70% yield of fully protected NuAA monomer [(D/L)-AA(Boc)GAdMB].

Figure 6:
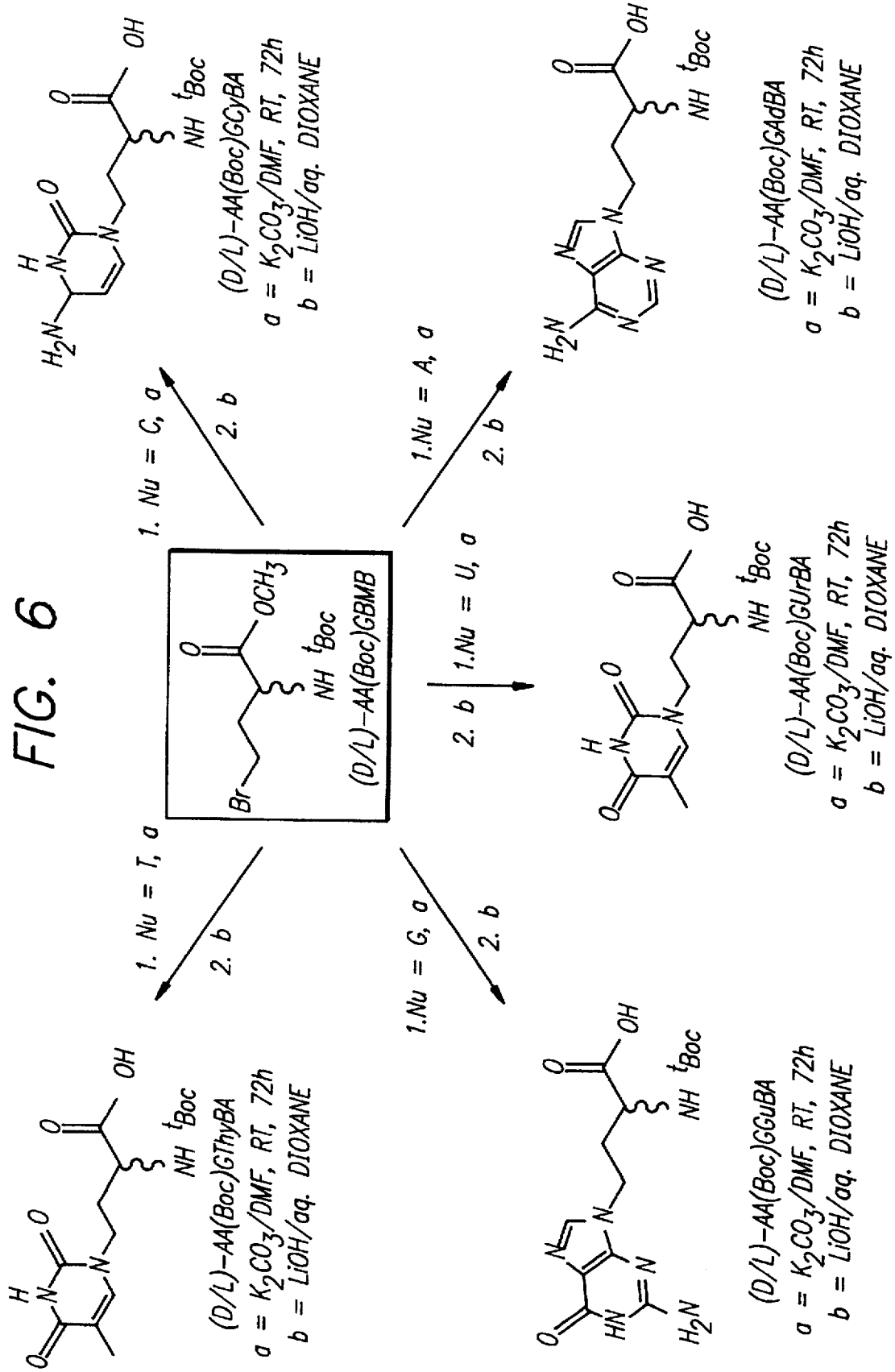
FIG. 6 illustrates a synthetic strategy for preparing NuAA monomers containing various nucleic bases (A, T, G, C, U).

As shown in FIG. 6, NuAA monomers in which the nucleic base is other than adenine (A) can be prepared similarly by reacting 4-bromo-2-(t-butyloxycarbonylamino) -methylbutyrate [AA(Boc)GBMB] with the appropriately protected nucleic base, such as guanine (G), cytosine (C), thymine (T), uracil (U) or their heterocyclic analogs.

The individual chemical reactions summarized above were carried out essentially as described in the literature. The following detailed description of the individual steps is provided for the further convenience of the reader.

(1) Synthesis of (D/L)-α-Amino-γ-butyrolactone hydrobromide [(D/L)-AAGBL.HBr]:

(D/L)-α-Amino-γ-butyrolactone hydrobromide [(D/L)-AAGBL.HBr] was synthesized from (D/L)-methionine by following the modified literature procedure referred to above. To an aqueous ethanolic solution (1:1, 200 mL), (D/L)-methionine (0.1M, 14.92 g) and methylbromoacetate (0.11M, 17.17 g) were added at room temperature. The resulting suspension was heated to 55–60° C. in an oil bath until it became a homogeneous solution (about 1.5–2 hrs). It was left at that temperature overnight (12 hrs). After 12 hrs the resulting dark yellow solution was heated at reflux for about 3–5 hrs. The thin layer chromatograph (tlc) (n-BuOH:H$_2$O:HOAc=4:1:1) of this reaction mixture showed that the reaction had gone to completion. The dark brown solution was cooled to room temperature and evaporated to dryness under vacuum using a water aspirator. To this viscous dark brown residue a mixture of isopropanol and toluene (1:1, 50 mL) was added, and the last traces of water were removed by evaporating the resulting solution to dryness. The precipitated, off white crystalline solid was suspended in cold absolute ethanol (50 mL), filtered off, washed thoroughly with a mixture of cold ethanol and toluene (1:1, 50 mL) and air dried. The filtrate and the washings were combined and re-evaporated to generate a viscous liquid which was stirred with 4M HCl in dioxane (60 mL) at −40° C. for 4–6 hrs. It was left in a refrigerator overnight. The second crop of the precipitated white crystals were filtered off, washed thoroughly with cold ethanol and air dried. The overall yield of the product (D/L)-AAGBL.HBr was about 15–15.5 g. (80–85%). Analogously, the enantiomers (L)-AAGBL.HBr and (D)-AAGBL.HBr were synthesized from (L)-methionine and (D)-methionine, respectively, and were purified by recrystallization from 10% aqueous ethanol in about 75% yield. The structures of all of the stereoisomers were confirmed by $^1$H, $^{13}$C NMR, specific rotation and mass spectrometry.

(2) Synthesis of (D/L)-α-Amino-γ-bromo butyric acid Hydrogen bromide [(D/L)-AAGBBA.HBr]:

(D/L)-AAGBL.HBr (0.05M, 9.101 g, Aldrich Chemical Co.) was heated with freshly made 35% HBr-HOAc solution (10 equiv, 0.5M) in a teflon vessel containing a steel bomb at 75' C. for 3 hrs. The steel bomb was cooled to room temperature. The reaction mixture had precipitated and formed white crystals. This slurry was transferred to a flask and the contents were evaporated at 40° C. using a water aspirator vacuum to remove excess HBr and HOAc. The resultant yellowish white crystalline solid was suspended in a 1:1 mixture of MeOH and toluene and evaporated again to remove traces of HOAc. The yellowish white crystalline solid was resuspended in diethylether, filtered off, washed thoroughly with diethyl ether and air dried to give white crystalline product in almost quantitative yield (>95%). The proton NMR of this crude product showed that about 10–15% of the lactone remained unreacted. The product bromoamino acid, (D/L)-AAGBBA.HBr could be recrystallized from absolute ethanol but it was used without any further purification for the next step.

The enantiomers (L)-AAGBBA.HBr and (D)-AAGBBA.HBr were synthesized from (L)-AAGBL.HBr and (D)-AAGL.HBr, respectively, by following the same procedure and were recrystallized from absolute ethanol. The structures of all of the stereoisomers were confirmed by $^1$H, $^{13}$C NMR, specific rotation and mass spectrometry.

(3) Synthesis of (D/L)-α-amino-γ-bromomethylbutyrate hydrogen chloride [(D/L)-AAGBMB.HCl]:

The methyl ester (D/L)-AAGBMBe.HCl was prepared in quantitative yield by dissolving the bromoamino acid, (D/L)-AAGBBA.HBr (0.05M, 13.15 g) in an excess of absolute methanol (5 mL/mM) and bubbling dry HCl gas through this methanolic solution for about 2 hrs while maintaining the reaction temperature between 35–40° C. The light yellow solution was evaporated below 40° C. using a water aspirator vacuum to remove th excess HCl gas and methanol. The residual yellow liquid was diluted with a mixture of methanol and toluene (1:1, 50 mL) and evaporated again to dryness to give a syrupy liquid which on further drying at high vacuum gave ivory-white crystals of bromoamino methyl ester, (D/L)-AAGBMB.HCl, which could be purified by crystallization from CHCl$_3$-diethyl ether mixture. For practical purposes, the product was pure enough for the ensuing step.

The enantiomers (L)-AAGBMB.HBr and (D)-AAGBMB.HBr were synthesized similarly from (L)-AAGBBA.HBr and (D)-AAGBBA.HBr respectively and were recrystallized from absolute ethanol and diethylether as co-solvent. The structures of all of the stereoisomers were confirmed by $^1$H, $^{13}$C NMR, specific rotation and mass spectrometry.

(4) Synthesis of (D/L)-α-(t-Boc)amino-γ-bromo methylbutyrate [(D/L)-AA(Boc)GBMB]:

The carbamate, (D/L)-AA(Boc)GBMB, was prepared by treating the haloamino ester, (D/L)-AAGBMB.HCl with t-butyloxycarbonate in the presence of NaHCO$_3$. To an aqueous solution of (D/L)-AAGBMB.HCl(0.05M, 11.63 g; 15 mL H2O), an aqueous solution of NaHCO$_3$ (0.11M, 9.24 g, 110 mL H$_2$O) was added at 0° C. After the initial evolution of CO$_2$ gas, a solution of t-butyloxycarbonate (0.055M, 12 g) in p-dioxane (65 mL) was added. The resulting reaction mixture was vigorously stirred at 0° C. for an hour and then warmed up to room temperature gradually. The reaction mixture was stirred at room temperature and was monitored by thin layer chromatography. The reaction went to completion within 4–6 hrs. The precipitated oily liquid (denser than water) was separated and the supernatant was extracted with chloroform. The chloroform extract was combined with the oil liquid and was then thoroughly washed with water. The organic extract after evaporation at room temperature provided a light yellow oil with characteristic odor of tBuOH. The product (D/L)-AA(Boc)GBMB was purified as white crystals in about 85% yield by flash chromatography using a gradient of 7.5–15% ethylacetate (EA) in hexane. It could also be crystallized from diethyl ether-petroleum ether mixture.

The enantiomeric methyl esters, (L)-AA(Boc)GBMB and (D)-AA(Boc)GBMB, were synthesized similarly from (L)-AAGBMB.HBr and (D)-AAGBMB.HBr, respectively, and were recrystallized from a diethyl ether and petroleum ether as co-solvents. The structures of all of the stereoisomers were confirmed by $^1$H, $^{13}$C NMR, specific rotation and mass spectrometry.

(5) Synthesis of (D/L)-α-Amino(tBoc)-γ-(N9)-adeninyl methylbutyrate [(D/L)-AA(Boc)GAdMB]:

To an oven-dried flask containing a suspension of adenine (0.025M, 3.378 g) in freshly distilled dimethylformamide (DMF) (90 mL; 3.5 mL/mM base), anhydrous K$_2$CO$_3$ was added. This mixture was stirred for 15 min at room temperature and (D/L)-AA(Boc)GBMB (0.025M, 7.4 g) was added in 25 mL dry DMF under an inert atmosphere. The reaction was monitored by thin layer chromatography and the condensation went to completion by leaving the reaction mixture stirred under inert atm at room temperature over 72 hrs. The reaction mixture was filtered off to remove the precipitated salts (KBr, KHCO$_3$). The filter cake was thoroughly washed with DMF. The washings were combined with the filtrate and the resulting solution was evaporated to dryness to give a slurry containing precipitated solid. This viscous liquid was diluted with CHCl$_3$ (50 mL) and was filtered to remove the solid. The organic filtrate was thoroughly washed with water, dried over Na$_2$SO$_4$ and evaporated to give a yellowish liquid. The N9-substituted product (D/L)-AA(Boc)GAdMB, was purified by flash chromatography using 4–7% MeOH-EA solvent system in about 80–85% yield.

The adeninyl carbamate methylester enantiomers, (L)-AA(Boc)GAdMB and (D)-AA(Boc)GAdMB were synthesized similarly from the corresponding bromocarbamate esters, (L)-AA(Boc)GBMB and (D)-AA(Boc)GBMB and adenine, respectively. The structures of all of the stereoisomers were confirmed by $^1$H, $^{13}$C NMR, specific rotation and mass spectrometry.

(6) Synthesis of (D/L)-α-Amino(tBoc)-γ-(N9)-adeninyl butyric acid [(D/L)-AA (Boc)GAdBA]:

The hydrolysis of the methyl ester was carried out to provide the corresponding tBoc-protected amino acid as a building block for the solid phase peptide synthesis. The methyl ester (D/L)-AA(Boc)GAdMB (0.01M, 3.50 g) was dissolved in aqueous dioxane (1:1), and the clear solution was chilled to 0° to 5° C. To this cold solution an aqueous solution of LiOH.H$_2$O (0.0115M, 0.5 g) was added. The hydrolysis was complete within 3 hrs. of stirring the solution below 5° C. The reaction solution was evaporated on a rotovap below 5° C. and the last traces of water and dioxane were removed azeotropically using benzene as co-solvent. The white solid that was obtained was redissolved in a minimum amount of aqueous dioxane and then acidified to pH 4–6 with HCl-dioxane solution. The precipitated white solid was filtered, washed with dioxane and dried under high vacuum. The yield of the nucleic aminoacyl monomer (D/L)-AA(Boc)GAdBA was about 90–95%.

The nucleic aminoacyl enantiomers (L)-AA(Boc)GAdBA and (D)-AA(Boc)GAdBA were prepared similarly by hydrolysis of the corresponding methylesters. (L)-AA(Boc) GAdMB and (D)-AA(Boc)GAdMB. The structures of all of the stereoisomers were confirmed by $^1$H, $^{13}$C NMR, specific rotation and mass spectrometry.

Example 8

Figure 7:
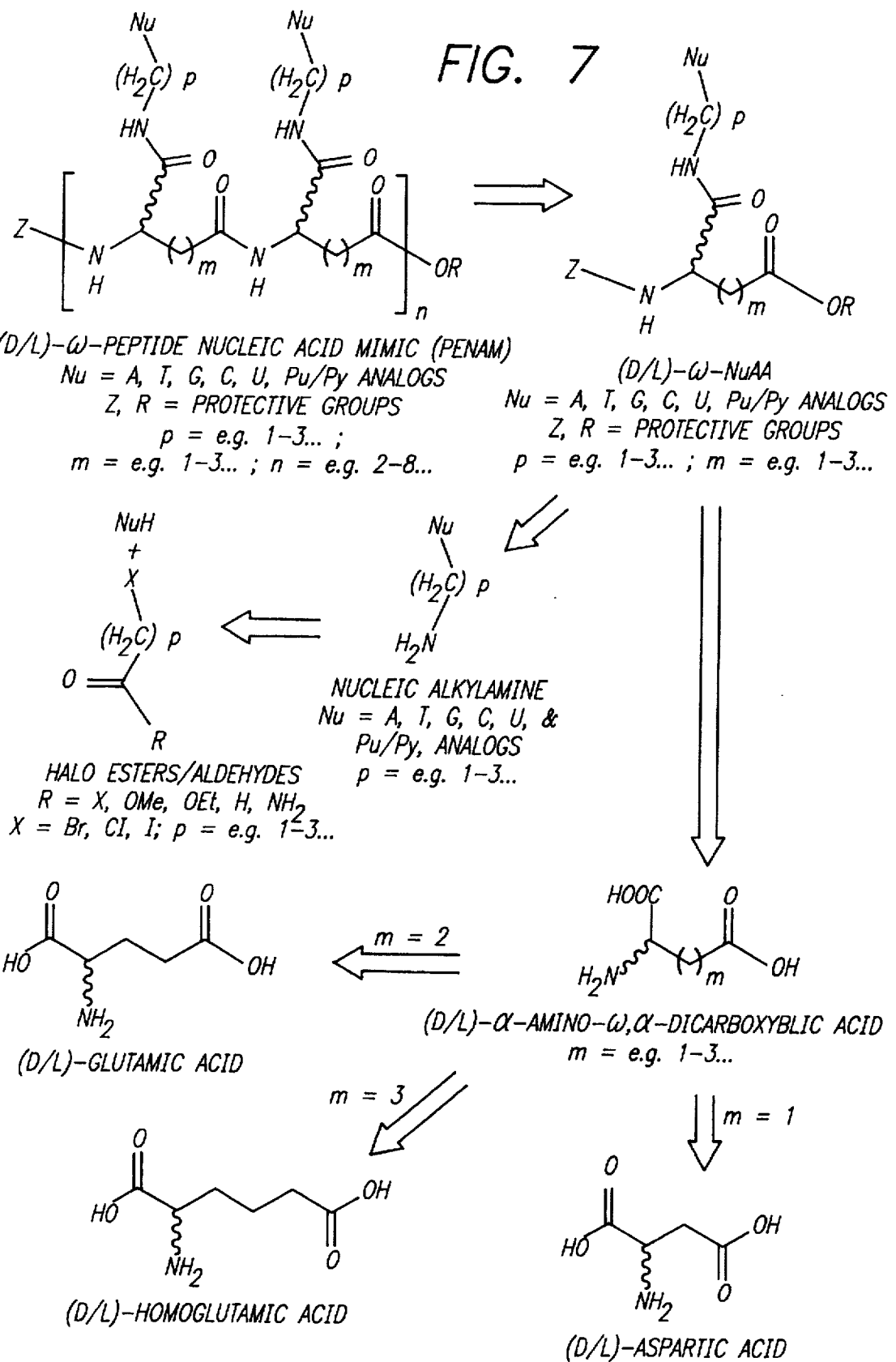
FIG. 7 is an illustrative example of the retrosynthesis of PENAMs and NuAA monomers from α-amino-ω, α-dicarboxylic acids.

Synthesis of NuAA monomers derived from α-amino-(β-/γ-/δ-),α-dicarboxylic acids:

α-amino-(β-/γ-/δ-), α-dicarboxylic acids offer the unique advantage of forming amide bonds (peptide bonds) either at α-carboxylic group or at β-/γ-/δ-carboxylic group. As a consequence α-amino-(β-/γ-/δ-), α-dicarboxylic acids can be used to introduce flexibility via β-/γ-/δ-amide linkages in the peptide backbone over α-amino-α-carboxylic acids. The α-carboxylic acid group could be chemically manipulated to a suitable side chain, on which the nucleic base is introduced at a homomorphic distance. Various synthetic transformations known in the art can be utilized to prepare these NuAA monomers [63–65]. As an example, a retrosynthetic strategy has been illustrated in FIG. 7.

Example 9

Figure 8:
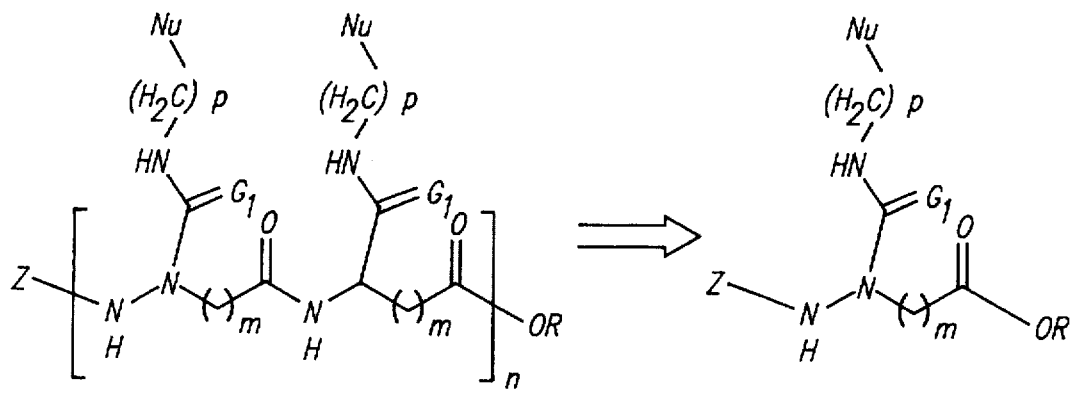
FIG. 8 is an illustrative example of the retrosynthesis of aza-NuAA monomers from aza-amino acids.
Figure 8:
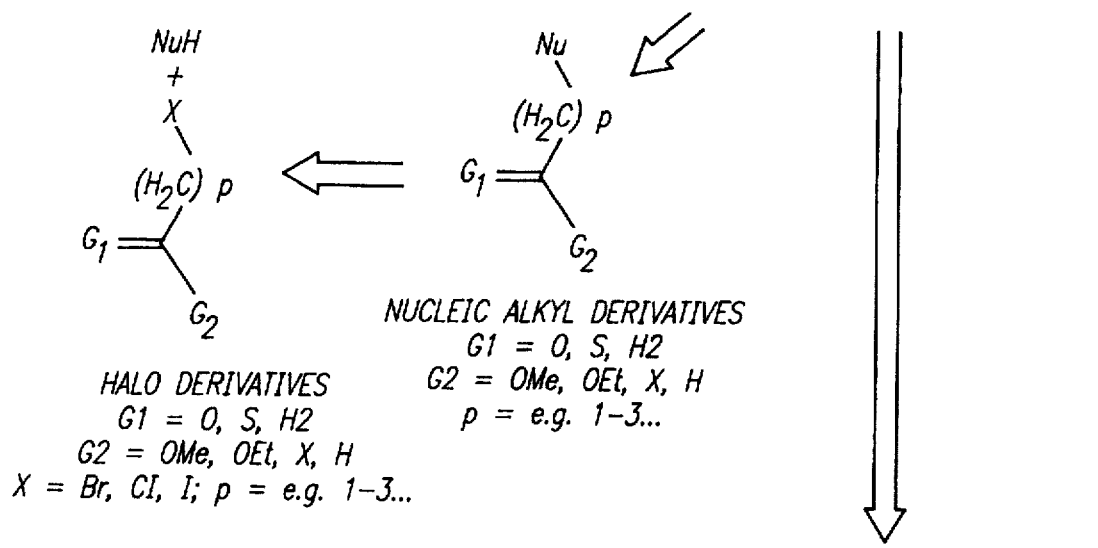
Figure 8:
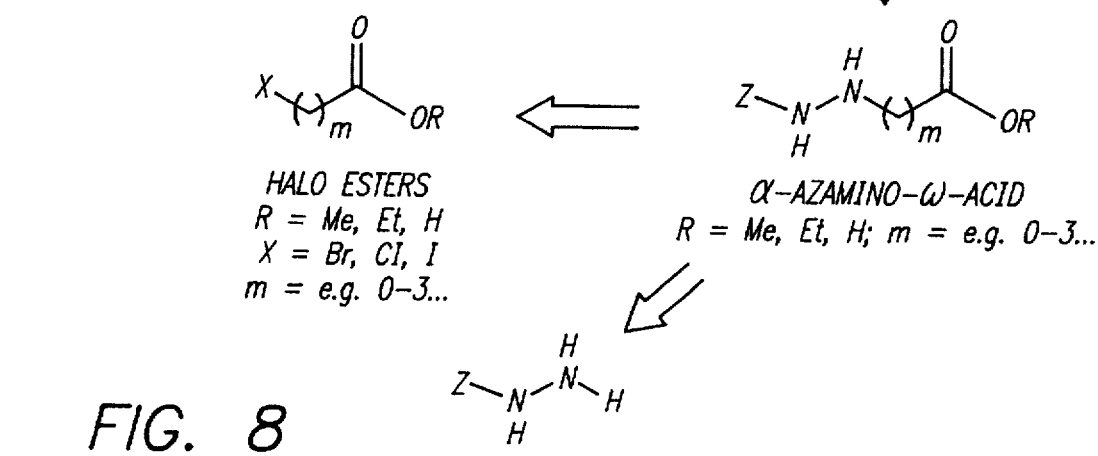

Synthesis of aza-NuAA monomers:

Aza-NuAA monomers can be derived from nucleic "aza-amino acids". The nucleic aza-amino acids can be easily prepared from aza-amino acid derivatives, such as semicarbazides (aza-amino acid amides) and carbazic acid (hydrazinecarboxylic acid) esters. Usually the aza-amino acid is relatively unstable unless protected at the carboxylic group, due to the fact that N-carboxylic acids are readily decarboxylated. Various synthetic methods, known in the art can be utilized to synthesize these aza-amino acid derivatives [68]. Preparation of aza-amino acid derivatives can be based on hydrazine chemistry. In general, a nucleic base or its analog with suitable linker is condensed with hydrazine or a protected hydrazine. This alkylated or nucleic base substituted hydrazine is then treated with an appropriate "carbonyl donor" such as carbonochloridic esters or carbonic diesters or haloesters. Such a retrosynthetic strategy is illustrated in FIG. 8.

Example 10

Assembly of PENAMs from NuAA monomers via solid phase peptide synthesis

Protected NuAA monomers, as described in Example 7, can be oligomerized using the t-butyloxycarbamate (tBoc) strategy on the automated peptide synthesizer to prepare PENAMs of the desired chain length. To summarize, this strategy requires deprotection of the methyl ester to free the carboxylic acid. The methyl ester (D/L)-AA(Boc)GAdMB was hydrolyzed by LiOH to yield t-BOC protected NuAA monomer, (D/L)-AA(Boc)GAdBA. Similarly, (L)-4-(N9-adeninyl)-2-amino(tBoc)-butyric acid, [(L)-AA(Boc) GAdBA] and (D)-4-(N9-adeninyl)-2-amino(tBoc)-butyric acid [(D)-AA(Boc)GAdBA] have also been synthesized from (L)-methionine and (D)-methionine, respectively.

The following is an even more detailed description of the individual synthetic steps:

All three stereoisomers, D/L-, L- and D- of the unnatural NuAA monomer 4-(N9-Adeninyl)-2-amino-butyric acid [also abbreviated as GAdAABA or AdhAla] and their derivatives were synthesized in the laboratory in enantiomerically pure form, as described in the preceding examples. All other amino acid derivatives were of the L-configuration unless stated, purchased either from Applied Biosystems Inc. (ABI) or Bachem Inc. and were checked for purity by thin layer chromatography, melting point, and optical rotation. p-methylbenzhydrylamine (MBHA) resin, (copolystyrene-1% divinylbenzene, 0.69 meq/g, 100–200 mesh) was purchased from Peninsula Laboratory, CA. All solvents were purchased either from ABI or Burdick and Jackson (distilled in glass grade). Dimethylformamide (DMF) and disopropylethylamine (DIPEA) were distilled from ninhydrin, followed by calcium hydride at reduced pressure and stored over molecular sieves (Linde, 4 Angstrom). Boc deprotection reagent, trifluoroacetic acid (TFA), and peptide coupling reagents, dicyclohexylcarbodiimide (DCC), 1-hydroxybenzotriazole (HOBT) were purchased from ABI and were used as supplied. 1-Benzotriazolyloxy-tris(dimethylamino)-phosphonium hexafluorophosphate (BOP) and O-(benzotriazol-1-yl-)-1,1,3,3-tetramethyluronium hexafluorophosphate (HBTU) were purchased from Richielu Chemicals Co., Canada. 1-Hydroxy-7-azabenzotriazole (HOAT) was either synthesized in the laboratory or was purchased from the Miligen Corporation.

Solid phase peptide synthesis was carried out on an Applied Biosystem Inc. (ABI) automated peptide synthesizer, model 431A, using standard BOC chemistry protocols. In order to obtain the end product as an amide at the C-terminus after HF cleavage, p-methylbenzhydrylamine (MBHA) resin was used as a polymeric support to anchor the growing peptide chain. The peptide synthesizer was operated in a semi-automated manner and all the cycles were modified according to the scale of the reaction and to facilitate the completion of each coupling reaction.

The PENAMs were synthesized with L-lysine residues flanking both the N-terminus and the C-terminus because they are believed to enhance the solubility of the resulting PENAM in aqueous solutions.

A racemic PENAM [H-Lys-{(D/L)-(AdhAla)$_{10}$}-Lys-NH$_2$] was synthesized from 4-(N9-adeninyl)-2-amino-butyric acid [(D/L)-GAdAABA] and L-lysine on a peptide synthesizer on 0.2 mM scale. DCC and HOBT were used as the coupling reagents to couple the lysine residues whereas BOP and HOBT were used to couple the nucleic aminoacid monomers.

As anticipated, the purification of this racemic PENAM resulted in the generation of a large number of diastereomers ($2^{10}$=1024), which were isolated as a mixture by HPLC on C-18 reverse phase column. The molecular weight of this PENAM was in accordance with its calculated mass as determined by mass spectrometry.

Similarly, the enantiomerically pure PENAMs [H-Lys-{(D-AdhAla)-(L-AdhAla)-}$_5$-Lys-NH2] and [H-Lys-(L-AdhAla)$_{10}$-Lys-NH2] were synthesized from the corresponding nucleicamino acids. (D)-4-(N9-adeninyl)-2-amino-butyric acid [(D)-GAdAABA or (D)-γ-adeninyl-α-amino-butyric acid] and (L)-4-(N9-adeninyl)-2-amino-butyric acid [(L)-GAdAABA or (L)-γ-adeninyl-α-amino-butyric acid] and (L)-lysine on 0.2 mM scale, by following the protocols used for the racemic PENAM, [H-Lys-{(D/L)-(AhAla)$_{10}$}-Lys-NH$_2$]. The only difference was the use of a new coupling reagent HOAT in combination with HBTU which is believed to increase the coupling yield and to minimize racemization at the alpha-carbon [285].

Example 11

Binding of a PENAM to a target nucleic acid

Thermal denaturation of an ordered, native structure of a nucleic acid disrupts the base-pair stacking and, as a result, the UV absorbance increases. The change in UV absorbance, known as hypochromicity, is a measure of base-pairing and base-stacking between the two complementary strands. The UV absorbance profile as a function of temperature is called a melting curve and the midpoint of this curve is defined as the melting temperature, $T_m$, at which 50% of the double strand is dissociated into its two single strands. Thus, the measurement of UV absorbance melting curves provides qualitative and quantitative structural information about the nucleic acid bound to its complementary ligand. $T_m$ also depends on the concentration of the oligonucleotide and the properties of the solvent (buffer: pH, ionic strength, etc.).

Binding studies were carried out by hybridizing the isolated PENAM described above to its complementary oligonucleotide "dT$_{10}$" followed by thermal denaturation and measurement of UV absorbance as a function of temperature. The synthetic oligodeoxynucleotide (ODN) dT$_{10}$ and its complementary oligodeoxynucleotide dA$_{10}$ were used as the reference nucleic acids. The samples prepared in phosphate buffer (Na$_x$PO$_4$) can precipitate magnesium phosphate at high temperature during the thermal denaturation cycle. This problem was readily avoided by repeating the experiment in 10 mM sodium cacodylate buffer (Me$_2$AsO$_2$Na) instead of the phosphate buffer. The results are summarized in TABLE 1.

TABLE 1

| Reference Strand | Complementary Strand | Stoichio- | T$_m$ (°C.) | |
|---|---|---|---|---|
| dNu | dNu pNu | metry | Na$_x$PO$_4$ | Me$_2$AsO$_2$Na |
| dT$_{10}$ | dA$_{10}$ — | 1:1:0 | 28.045 | 29.41 |
| dT$_{10}$ | — KpA$_{10}$K$_m$ | 1:0:1 | 31.26 | 31.00 |
| dT$_{10}$ | dA$_{10}$ KpA$_{10}$K$_m$ | 1:1:1 | 31.41 | 31.052 |
| dT$_{10}$ | — 2KpA$_{10}$K$_m$ | 1:0:2 | 30.8 | 32.57 |
| dT$_{10}$ | dA$_{10}$ 2KpA$_{10}$K$_m$ | 1:1:2 | 30.07 | 32.26 |
| 2dT$_{10}$ | — KpA$_{10}$K$_m$ | 2:0:1 | — | 32.28 |
| — | — 2KpA$_{10}$K$_m$ | 0:0:1 | no real transition | no real transition | dNu = deoxyoligonucleotide; pNu = nucleic oligopeptide; pA$_{10}$ = PENAM A10; K$_m$ = lysine amide at the C-terminus.

These data confirm that the PENAM binds to its complementary nucleic acid strand, and that it exhibits a real transition from an ordered structure to a disordered one on thermal denaturation.

Strikingly, the PENAM was observed to melt at an even higher temperature than the reference ODN, dT$_{10}$:dA$_{10}$. Although the increase in melting temperature was somewhat modest, it is a significant result because it shows that, in spite of being a complex diastereomeric mixture, the PENAMs recandized and bound quite effectively to their complementary oligodeoxynucleotide strands. It is thus expected that certain stereospecific PENAMs will bind to their complementary oligonucleotide targets even more tightly than the observed average for the mixture.

In addition, the binding affinity of these PENAMs can be further enhanced by introducing modified nucleic bases which can improve base pairing by forming additional hydrogen bonds or by conjugation with known nucleic acid intercalating agents such as acridines, anthraquinones, phenanthridines, phenazines, as described above.

REFERENCES

1. Miller, P. S. and Ts'o, P. O. P. "Oligonucleotide Inhibitors of Gene Expression in Living Cells: New Opportunities in Drug Design". Ann. Rep. Med. Chem. 23: 295–304, 1988. Review.

2. Matteucci, M. D. and Bischofberger, N. "Sequence-defined Oligonucleotides as Potential Therapeutics". Ann. Rep. Med. Chem. 26: 287–296, 1991. Review.

3. Cohen, J. S. Oligodeoxynucleotides: Antisense Inhibitors of Gene Expression. Topics in Molecular and Structural Biology. 1–255, 1989, CRC Press, Boca Raton, Fla.

4. Ghosh, M. K. and Cohen, J. S. "Oligodeoxynucleotides as antisense inhibitors of gene expression". Prog. in Nu. Acid Res. and Mol. Biol. 42(79): 79–126, 1992. Review.

5. Helene, C. and Toulme, J. -J. "Specific Regulation of Gene Expression by Antisense, Sense and Antigene Nucleic Acids". Biochim. Biophys. Acta. 1049: 99–125, 1990. Review.

6. Stein, C. A. and Cohen, J. S. "Oligodeoxynucleotides as Inhibitors of Gene Expression: A Review". Cancer Res. 48: 2659, 1988. Review.

7. Stein, C. A. and Cheng, Y. "Antisense Oligonucleotides as Therapeutic Agents-Is the Bullet Really Magic?". Science. 261: 1004–1011, 1993. Review.

8. Uhlmann, E. and Peyman, A. "Antisense Oligonucleotides: A New Therapeutic Principle". Chem. Rev. 90(4): 544–579, 1990. Review.

9. Goodchild, J. "Conjugates of oligonucleotides and modified oligonucleotides: a review of their synthesis and properties". Bioconjug Chem. 1(3): 165–87, 1990. Review.

10. Stein, C. A., Tonkinson, J. L., and Yakubov, L. "Phosphorothioate oligodeoxynucleotides—anti-sense inhibitors of gene expression?". Pharmacol Ther. 52(3): 365–84, 1991. Review.

11. Zon, G. and Geiser, T. G. "Phosphorothioate oligonucleotides: chemistry, purification, analysis, scale-up and future directions". Anticancer Drug Des. 6(6): 539–68, 1991. Review.

12. Beaucage, S. L. and Iyer, R. P. "Advances in the Synthesis of Oligonucleotides by the Phosphoramidite Approach". Tetrahedron. 48(12): 2223–2311, 1992. Review.

13. Tidd, D. M. "Methylphosphonodiester/phosphodiester chimeric oligodeoxynucleotides". Biochem Soc Trans. 20(4): 746–9, 1992.

14. Beaucage, S. L. and Iyer, R. P. "The Synthesis of Modified Oligonucleotides by the Phosphoramidite Approach and their Applications". Tetrahedron. 49(28): 6123–6194, 1993. Review.

15. Stirchak, E. P., Summerton, J. E., and Weller, D. E. J. Org. Chem. 52: 4202–4206, 1987.

16. Stirchak, E. P., Summerton, J. E., and Weller, D. D. "Uncharged stereoregular nucleic acid analogs: 2. Morpholino nucleoside with oligomers with carbamate internucleoside linkages". Nucl. Acids Res. 15: 6129–6140, 1989.

17. Pitha, J. and Pitha, P. M. Biopolymers. 9: 965, 1970.

18. Pitha, J., Pitha, P. M., and Ts'o, P. O. P. *Biochem. Biophys. Acta.* 204: 39, 1970.

19. Kropachev, V. A., et al. *Makromol. Chem. Suppl.* 9: 47–51, 1985.

20. Takemoto, K. and Inaki, Y. *Polym. Mat. Sci. Eng.* 58: 250, 1988.

21. Doel, M. T., Jones, A. S., and Taylor, N. "An Approach to the Synthesis of Peptide Analoges of Oligonucleotides (Nucleopeptides)" *Tettrahedron Lett.* 27: 2285–2288, 1969.

22. Nollet, A. J. H., Huting, C. M., and Pandit, U. K. "Unconventional Nucleotide Analogues-I: $N^9$-Purinyl a-amino acids". *Tetrahedron.* 25: 5971–5981, 1969.

23. Nollet, A. J. H. and Pandit, U. K. "Unconventional Nucleotide Analogues-II: Synthesis of the Adenyl Analogue of Willardine". *Tetrahedron.* 25: 5983–5887, 1919.

24. Nollet, A. J. H. and Pandit, U. K. "Unconventional Nucleotide Analogues-III: 4-(N1-Pyrimidyl)-2-Aminobutyric Acids". *Tetrahedron.* 25: 5989–5994, 1969.

25. De Koning, H. and Pandit, U. K. "Unconventional Nucleotide Analogues. VI.: Synthesis of Purinyl- and Pyrimidinyl- Peptides". *Rec. Trav. Chim.* 91: 1069–1081, 1971.

26. Buttery, J. D., Jones, A. S., and Walker, R. T. "Synthetic Analogues of Polynucleotides-XIII: The Resolution of DL-b-(Thymin-1-yl)alanine and Polymerization of the b-(Thymin-1-yl)alanines". *Tetrahedron.* 31: 73–75, 1975.

27. Lidak, M. Y., et al. *Khim. Getero. Sodinenii.* 11: 1560–63, 1975.

28. Draminski, M. and Pitha, J. "Polypeptides Containing Adenine and Uracil Residues". *Makromol. Chem.* 179: 2195–2200, 1978.

29. Olsuf'eva, E. N. and Shvachkin, Y. P. *Zh. Obs. Khim.* 49: 1147–51, 1979.

30. Semiletov, Y. A., et al. *Zh. Obs. Khim.* 51: 230–8, 1981.

31. Raukas, E., et al. *Stud. Biophys.* 89: 187–195, 1982.

32. Lidak, M. Y., et al. *Khim. Getero. Soedinenii.* 3: 402–5, 1983.

33. Cheikh, A. B. and Orgel, L. E. "Polymerization of Amino Acids containing Nucleotide Bases". *J. Mol. Evol.* 30: 315–321, 1990.

34. Huang, S. -B., Nelson, J. S., and Weller, D. D. "Acyclic Nucleic Acid Analogues: Synthesis and Oligomerization of gamma,4-Diamino-2-oxo-1(2H)-pyrimidinepentanoic Acid and delta,4-Diamino-2-oxo-1(2H)-pyrimidinehexanoic acid". *J. Org. Chem.* 56: 6007–6018, 1991.

35. Weller, D. D., et al. "Molecular Modelling of Acyclic Polyamide Oligonucleotide Analogues". *J. Org. Chem.* 56: 6000–6006, 1991.

36. Nielsen, P. E., et al. "Sequence-selective recognition of DNA by strand displacement with a thymine-substituted polyamide". *Science.* 254(5037): 1497–500, 1991.

37. Egholm, M., et al. "Peptide Nucleic Acids (Pna) -Oligonucleotide Analogues With An Achiral Peptide Backbone". *Journal Of The American Chemical Society.* 114(5): 1895–1897, 1992.

38. Egholm, M., et al. "Recognition Of Guanine And Adenine In Dna By Cytosine And Thymine Containing Peptide Nucleic Acids (Pna)(1,2)". *Journal Of The American Chemical Society.* 114(24): 9677–9678, 1992.

39. Egholm, M., et al. "Peptide Nucleic Acids Containing Adenine Or Guanine Recognize Thymine And Cytosine In Complementary Dna Sequences". *Journal Of The Chemical Society-Chemical Communications.* (N9): 800–801, 1993.

40. Egholm, M., et al. "PNA hybridizes to complementary oligonucleotides obeying the Watson-Crick hydrogen-bonding rules [see comments]". *Nature.* 365(6446): 566–8, 1993.

41. Dueholm, K. L., et al. "Peptide Nucleic Acid (Pna) With A Chiral Backbone Based On Alanine". *Bioorganic & Medicinal Chemistry Letters.* 4(8): 1077–1080, 1994.

42. Nielsen, P. E., Egholm, M., and Buchardt, O. "Peptide Nucleic Acid (Pna)—A Dna Mimic With A Peptide Backbone". *Bioconjugate Chemistry.* 5(1): 3–7, 1994.

43. Martin, F. H. and Castro, M. M. *Nucleic Acids Res.* 13: 8927, 1985.

44. Chollet, A. and Kawashima, E. *Nucleic Acids Res.* 16: 305, 1988.

45. Inoue, H., Imura, A., and Ohtsuka, E. *Nucleic Acids Res.* 13: 7119, 1985.

46. Summerton, J. and Bartlett, P. A. *J. Mol. Biol.* 122: 145, 1978.

47. Webb, T. R. and Matteucci, M. D. *J. Am. Chem. Soc.* 108: 2764, 1986.

48. Cowart, M., et al. *Biochemistry.* 28: 1975, 1989.

49. Conholly, B. A. "Synthetic oligodeoxynucleotides containing modified bases". *Methods Enzymol.* 211(36): 36–53, 1992. Review.

50. Griffin, L. C., et al. "Recognition Of All 4 Base Pairs Of Double-Helical Dna By Triple-Helix Formation—Design Of Nonnatural Deoxyribonucleosides For Pyrimidine.Purine Base Pair Binding". *Journal Of The American Chemical Society.* 114(21): 7976–7982, 1992.

51. Miller, P. S., et al. "Recognition Of A Guanine Cytosine Base Pair By 8-Oxoadenine". *Biochemistry.* 31(29): 6788–6793, 1992.

52. Xu, Y. Z., Zheng, Q., and Swann, P. F. "Synthesis By Post-Synthetic Substitution Of Oligomers Containing Guanine Modified At The δ-Position With S-Derivatives, N-Derivatives, O-Derivatives". *Tetrahedron.* 48(9): 1729–1740, 1992.

53. Xu, Y. Z., Zheng, Q. G., and Swann, P. F. "Synthesis Of Dna Containing Modified Bases By Postsynthetic Substitution-Synthesis of Oligomers Containing 4-Substituted Thymine-O4-Alkylthymine, 5-Methylcytosine, N4-(Dimethylamino)-5-Methylcytosine, And 4-Thiothymine". *Journal Of Organic Chemistry.* 57(14): 3839–3845, 1992.

54. Kurfurst, R., et al. "Oligo-Alpha-Deoxyribonucleotides With A Modified Nucleic Base And Covalently Linked To Reactive Agents". *Tetrahedron.* 49(32): 6975–6990, 1993.

55. Mohan, V., et al. "Molecular Recognition Of Watson-Crick Base-Pair Reversals In Triple-Helix Formation—Use of Nonnatural Oligonucleotide Bases". *Biopolymers.* 33(9): 1317–1325, 1993.

56. Sagi, J., et al. "Base-Modified Oligodeoxynucleotides 1. Effect Of 5-Alkyl, 5-(1-Alkenyl) And 5-(1-Alkynyl) Substitution Of The Pyrimidines On Duplex Stability And Hydrophobicity". *Tetrahedron Letters.* 34(13): 2191–2194, 1993.

57. Sanghvi, Y. S., et al. "Antisense Oligodeoxynucleotides—Synthesis, Biophysical And Biological Evaluation Of Oligodeoxynucleotides Containing Modified Pyrimidines". *Nucleic Acids Research.* 21(14): 3197–3203, 1993.

58. Solomon, M. S. and Hopkins, P. B. "Chemical Synthesis And Characterization Of Duplex Dna Containing A New Base Pair—A Nondisruptive, Benzofused Pyrimidine Analog". *Journal Of Organic Chemistry.* 58(8): 2232–2243, 1993.

59. Grein, T., et al. "3-Deaza- And 7-Deazapurines - Duplex Stability Of Oligonucleotides Containing Modified Adenine Or Guanine Bases". *Bioorganic & Medicinal Chemistry Letters.* 4(8): 971–976, 1994.

60. Lin, P. K. and Brown, D. M. "Oligonucleotides containing degenerate bases. Synthesis and uses". *Methods Mol Biol.* 26(187): 187–206, 1994. Review.

61. Meyer, R. J. "Incorporation of modified bases into oligonucleotides". *Methods Mol Biol.* 26(73): 73–91, 1994. Review.

62. Reese, C. B. and Varaprasad, C. V. N. S. "Synthesis Of Some 2',3'-Didehydro-2',3'-Dideoxynucleosides Derived From Modified Pyrimidine Bases". *Journal of The Chemical Society-Perkin Transactions* 1. (N2): 189–195, 1994.

63. Coppola, G. M. and Schuster, H. F. "Asymmetric Synthesis: Construction of Chiral Molecules Using Amino Acids." 1987 John Wiley & Sons. New York.

64. O'Donnell, M. J. "a-Amino Acid Synthesis". *Tetrahedron.* 44: 5253–5614, 1988. Review.

65. Williams, R. M. "Synthesis of Optically Active a-Amino Acids." 1989 Pergamon Press. Oxford, U.K.

66. Roberts, D. C. and Vellaccio, F. "Unusual Amino Acids in Peptide Synthesis." The Peptides. 1983 Academic Press Inc.

67. Spatola, A. F. "Peptide Backbone Modifications: A Structure-Activity Analysis of Peptides containing Amide Bond Surrogates." C.hemistry and Biochemistry of Amino Acids Peptides and Proteins. Weinstein ed. 1983 Marccel Dekker Inc. New York.

68. Gante, J. "Azapeptides". *Synthesis.* : 405–413, 1989. Review.

69. Blaney, F. "Molecular Modelling In The Pharmaceutical Industry". *Chemistry & Industry.* (N23): 791–794, 1990.

70. Laughton, C. A., et al. "Interaction of Berenil With The Tyrt Dna Sequence Studied By Footprinting And Molecular Modelling - Implications For The Design of Sequence-Specific Dna Recognition Agents". *Nucleic Acids Research.* 18(15): 4479–4488, 1990.

71. Sansom, C. E., et al. "Structural Studies On Bio-Active Compounds .14. Molecular Modelling of The Interactions Between Pentamidine And Dna". *Anti-Cancer Drug Design.* 5(3): 243–248, 1990.

72. Crabbe, M. J. C. and Falkingbridge, S. S. "Molecular Modelling Of Hiv-1 Reverse Transcriptase Inhibitors". *Aids Research And Human Retroviruses.* 7(3): 261–264, 1991.

73. Letellier, R., et al. "Molecular Modelling of 9-Aminoellipticine Interactions With Abasic Oligonucleotides". *Journal of Biomolecular Structure & Dynamics.* 9(3): 579–597, 1991.

74. Jaroszewski, J. W., et al. "Towards rational design of antisense DNA: molecular modelling of phosphorothioate DNA analogues". *Anticancer Drug Des.* 7(3): 253–62, 1992.

75. Diana, G. D., et al. "Antipicornavirus Compounds—Use of Rational Drug Design And Molecular Modelling". *Antiviral Chemistry & Chemotherapy.* 4(1): 1–10, 1993.

76. Ramsden, C. A. Quantitative Drug Design. Comprehensive Medicinal Chemistry. 4: 33–58, 83–104, 105–124, 125–138, 413–498, 1990, Pergammon Press, Oxford, U. K.

77. Martin, Y. C. "Computer-Assisted Rational Drug Design." in "Molecular Design and Modelling: Concepts and Applications", Langone, J. J., ed., Methods in Enzymology, 203:587–612, 1991 Academic Press Inc. San Diego.

78. Choplin, F. "Computers and the Medicinal Chemist." Quantitative Drug Design. Ramsden, C. A., ed., Comprehensive Medicinal Chemistry, 4:33–58, 1990 Pergammon Press. Oxford, U. K.

79. Loew, G. H. and Burt, S. K. "Quantum Mechanics and the Modelling of Drug Properties." Quantitative Drug Design. Ramsden, C. A., ed., Comprehensive Medicinal Chemistry, 4:105–124, 1990 Pergammon Press. Oxford, U. K.

80. Seibel, G. L. and Kollman, P. A. "Molecular Mechanics and the Modelling of Drug Structure." Quantitative Drug Design. Ramsden, C. A., ed., Comprehensive Medicinal Chemistry, 4:125–138, 1990 Pergammon Press. Oxford, U. K.

81. McCammon, J. A. "Dynamic Simulation and its Applications in Drug Research." Quantitative Drug Design. Ramsden, C. A., ed., Comprehensive Medicinal Chemistry, 4:139–152, 1990 Pergammon Press. Oxford, U. K.

82. Desjarlais, R., et al. *J. Med. Chem.* 31: 722, 1988.

83. Shoichet, B. K., Bodian, D. L., and Kuntz, I. D. *J. Comput. Chem.* 13: 380, 1992.

84. Meng, E. C., Shoichet, B. K., and Kuntz, I. D. *J. Comut. Chem.* 13: 505, 1992.

85. Blaney, J. M. and Hansch, C. "Application of Molecular Graphics to the Analysis of Macromolecular Structure." Quantitative Drug Design. Ramsden, C. A., ed., Comprehensive Medicinal Chemistry, 4:460–496, 1990 Pergammon Press. Oxford, U. K.

86. Marshall, G. R. and Naylor, C. B. "Use of Molecular Graphics for Structural Analysis of Small Molecules." Quantitative Drug Design. Ramsden, C. A., ed., Comprehensive Medicinal Chemistry, 4:432–458, 1990 Pergammon Press. Oxford, U. K.

87. Hansch, C. and et al. MEDCHEM®. Pomona College Medicinal Chemistry Laboratory, Seaver Chemistry Laboratory, Claremont, Calif. 91771.

88. Jurs, P. C., et al. "ADAPT". *J. Chem. Inf. Comput. Sci.* 25: 296, 1985.

89. Rich, A. "DNA Comes in Many Forms". *Gene.* 135 (1–2): 99–109, 1993. Review.

90. Fleisher, M. B., Mei, H., and Barton, J. K. "Metal Complexes which Target DNA Sites: Coupling Recognition to Reactivity." Nucleic Acids and Molecular Biology. Eckstein and Lilley ed. 1988 Springer-Verlag. Berlin, FRG.

91. Chassagne, C. and Schwartz, K. "Mapping of mRNA isoforms with an oligonucleotide probe: exonuclease VII compared with endonucleases". *Nucleic Acids Res.* 20(12): 3256, 1992.

92. Murray, V., et al. "Detection of polymorphisms using thermal cycling with a single oligonucleotide on a DNA sequencing gel". *Hum Mutat.* 2(2): 118–22, 1993.

93. Stahl, W. L., Eakin, T. J., and Baskin, D. G. "Selection of oligonucleotide probes for detection of mRNA isoforms". *J Histochem Cytochem.* 41(12): 1735–40, 1991.

94. Stewart, J. M. and Young, J. D. "Solid Phase Peptide Synthesis." 198.4 Pierce Chemical Company. Rockford, Ill.

95. Boado, R. J. and Pardridge, W. M. "Complete protection of antisense oligonucleotides against serum nuclease degradation by an avidin-biotin system". *Bioconjug Chem.* 3(6): 519–23, 1992.

96. Bunnell, B. A., Askari, F. K., and Wilson, J. M. "Targeted delivery of antisense oligonucleotides by molecular conjugates". *Somat Cell Mol Genet.* 18(6): 559–69, 1992.

97. Chavany, C., et al. "Polyalkylcyanoacrylate nanoparticles as polymeric carriers for antisense oligonucleotides". *Pharm Res.* 9(4): 441–9, 1992.

98. Juliano, R. L. and Akhtar, S. "Liposomes as a drug delivery system for antisense oligonucleotides". *Antisense Res Dev.* 2(2): 165–76, 1992.

99. MacKellar, C., et al. "Synthesis and physical properties of anti-HIV antisense oligonucleotides bearing terminal lipophilic groups". *Nucleic Acids Res.* 20(13): 3411–7, 1992.

100. Manoharan, M., et al. "Chemical modifications to improve uptake and bioavailability of antisense oligonucleotides". *Ann N Y Acad Sci.* 660(306): 306–9, 1992.

101. Ortigao, J. F., et al. "Antisense effect of oligodeoxynucleotides with inverted terminal internucleotidic linkages:

a minimal modification protecting against nucleolytic degradation". *Antisense Res Dev.* 2(2): 129–46, 1992.

102. Ryte, A. S., et al. "Interaction of cholesterol-conjugated alkylating oligonucleotide derivatives with cellular biopolymers". *Febs Lett.* 299(2): 124–6, 1992.

103. Barry, E. L., Gesek, F. A., and Friedman, P. A. "Introduction of antisense oligonucleotides into cells by permeabilization with streptolysin O". *Biotechniques.* 15(6): 1016–8, 1020, 1993.

104. Capaccioli, S., et al. "Cationic lipids improve antisense oligonucleotide uptake and prevent degradation in cultured cells and in human serum". *Biochem Biophys Res Commun.* 197(2): 818–25, 1993.

105. Clarenc, J. P., et al. "Delivery of antisense oligonucleotides by poly(L-lysine) conjugation and liposome encapsulation". *Anticancer Drug Des.* 8(1): 81–94, 1993. Review.

106. Gamper, H. B., et al. "Facile preparation of nuclease resistant 3' modified oligodeoxynucleotides". *Nucleic Acids Res.* 21(1): 145–50, 1993.

107. Khan, I. M. and Coulson, J. M. "A novel method to stabilise antisense oligonucleotides against exonuclease degradation". *Nucleic Acids Res.* 21(18): 4433, 1993.

108. Leonetti, J. P., et al. "Cell delivery and mechanisms of action of antisense oligonucleotides". *Prog Nucleic Acid Res Mol Biol.* 44(143): 143–66, 1993. Review.

109. Zelphati, O., Zon, G., and Leserman, L. "Inhibition of HIV-1 replication in cultured cells with antisense oligonucleotides encapsulated in immunoliposomes". *Antisense Res Dev.* 3(4): 323–38, 1993.

110. Maher(IIIrd), L. J. and Dolnick, B. J. *Biochem. Biophys.* 253: 214, 1987.

111. Goodchild, J., et al. *Arch. Biochem. Biophys.* 263: 401, 1988.

112. Griffin, L. C. and Dervan, P. B. "Recognition of Thymine-Adenine Base Pairs by Guanine in a Pyrimidine Triple Helix Motif". *Science.* 245: 967–971, 1989.

113. Maher(IIIrd), L. J., Wold, B., and Dervan, P. B. "Inhibition of Dna Binding Proteins By Oligonucleotide-Directed Triple Helix Formation". *Science.* 245(4919): 725–730, 1989.

114. Moser, H. E. and Dervan, P. B. "Sequence-Specific Cleavage of Double Helical DNA by Triple Helix Formation". *Science.* 238: 645–650, 1987.

115. Povsic, T. J. and et al. *J. Am. Chem. Soc.* 111: 3059–3061, 1989.

116. Lee, J. S. and et al. *Nucleic Acids Res.* 12: 6603–6614, 1984.

117. Cooney, M. and et al. *Science.* 241: 456–459, 1988.

118. Giovannangeli, C., et al. "Single-Stranded Dna As A Target For Triple-Helix Formation". *Journal Of The American Chemical Society.* 113(20): 7775–7777, 1991.

119. Beal, P. A. and Dervan, P. B. "Recognition Of Double Helical Dna By Alternate Strand Triple Helix Formation". *Journal Of The American Chemical Society.* 114(13): 4976–4982, 1992.

120. Giovannangeli, C., et al. "Triple-helix formation by oligonucleotides containing the three bases thymine, cytosine, and guanine". *Proc Natl Acad Sci U S A.* 89(18): 8631–5, 1992.

121. Helene, C., Thuong, N. T., and Harel, B. A. "Control of gene expression by triple helix-forming oligonucleotides. The antigene strategy". *Ann N Y Acad Sci.* 660(27): 27–36, 1992. Review.

122. Maher(IIIrd), L. J. "Dna Triple-Helix Formation—An Approach To Artificial Gene Repressors". *Bioessays.* 14(12): 807–815, 1992.

123. Mergny, J. L., et al. "Triple helix-specific ligands". *Science.* 256(5064): 1681–4, 1992.

124. Ono, A., Tso, P. O. P., and Kan, L. S. "Triplex Formation Of An Oligonucleotide Containing 2'-O-Methylpseudoisocytidine With A Dna Duplex At Neutral Ph". *Journal of Organic Chemistry.* 57(11): 3225–3230, 1992.

125. Strobel, S. A. and Dervan, P. B. "Triple helix-mediated single-site enzymatic cleavage of megabase genomic DNA". *Methods Enzymol.* 21(309): 309–21, 1992.

126. Ts'o P. O. et al. "Nonionic oligonucleotide analogs (Matagen) as anticodic agents in duplex and triplex formation". *Ann N Y Acad Sci.* 660: 159–77, 1992.

127. Asseline, U. and Thuong, N. T. "Oligonucleotides Tethered Via Nucleic Bases—A Potential New Set Of Compounds For Alternate Strand Triple-Helix Formation". *Tetrahedron Letters.* 34(26): 4173–4176, 1993.

128. Brossalina, E., Pascolo, E., and Toulme, J. J. "The binding of an antisense oligonucleotide to a hairpin structure via triplex formation inhibits chemical and biological reactions". *Nucleic Acids Res.* 21(24): 5616–22, 1993.

129. Davison, E. C. and Johnsson, K. "Triple Helix Binding Of Oligodeoxyribonucleotides Containing 8-Oxo-2'-Deoxyadenosine". *Nucleosides And Nucleotides.* 22(2): 237–243, 1993.

130. Han, H. and Dervan, P. B. "Sequence-specific recognition of double helical RNA and RNA.DNA by triple helix formation". *Proc Natl Acad Sci U S A.* 90: 3806–10, Z993.

131. Huang, C. Y., Cushman, C. D., and Miller, P. S. "Triplex Formation By An Oligonucleotide Containing N(4)-(3-Acetamidopropyl)Cytosine". *Journal Of Organic Chemistry.* 58(19): 5048–5049, 1993.

132. Jetter, M. C. and Hobbs, F. W. "7,8-Dihydro-8-Oxoadenine As A Replacement For Cytosine In The 3Rd Strand of Triple Helices—Triplex Formation Without Hypochromicity". *Biochemistry.* 32(13): 3249–3254, 1993.

133. Milligan, J. F., et al. "An anti-parallel triple helix motif with oligodeoxynucleotides containing 2'-deoxyguanosine and 7-deaza-2'-deoxyxanthosine". *Nucleic Acids Res.* 2Z(2): 327–33, 1993.

134. Sun, J. S. and Helene, C. "Oligonucleotide-Directed Triple-Helix Formation". *Current Opinion In Structural Biology.* 3(3): 345–356, 1993.

135. Tung, C. H., Breslauer, K. J., and Stein, S. "Polyamine-linked oligonucleotides for DNA triple helix formation". *Nucleic Acids Res.* 2Z(23): 5489–94, 1993.

136. Colocci, N. and Dervan, P. B. "Cooperative Binding Of 8-Mer Oligonucleotides Containing 5-(1-Propynyl)-2'-Deoxyuridine To Adjacent Dna Sites By Triple-Helix Formation". *Journal Of The American Chemical Society.* 16(2): 785–786, 1994.

137. Rao, T. S., et al. "Synthesis Of Triple Helix Forming Oligonucleotides With A Stretched Phosphodiester Backbone". *Nucleosides And Nucleotides.* 13(1–3): 255–273, 1994.

138. Helene, C. and Thuong, N. T. "Control of Gene Expression by Oligonucleotides Covalently Linked to Intercalating Agents". *Genome.* 31(1): 413–421, 1989. Review.

139. Sun, J. S., et al. "Sequence-Specific Intercalating Agents- Intercalation at Specific Sequences on Duplex DNA via Major Groove Recognition by Oligonucleotide Intercalator Conjugates". *Proc. Nat. Acad. Sci. USA.* 60(N2): 157–160, 1989.

140. Asseline, U. and Thuong, N. T. "Synthesis of Oligonucleotides covalently Linked to Intercalating Agents and to Reactive Groups". *Nucleosides and Nucleotides.* 10(1–3): 359–362, 1991.

141. Baguley, B. C. "DNA intercalating anti-tumour agents". *Anticancer Drug Des.* 6(1): 1–35, 1991. Review.

142. Bailly, C. and Henichart, J. P. "DNA recognition by intercalator-minor-groove binder hybrid molecules". *Bioconjug Chem.* 2(6): 379–93, 1991. Review.

143. Helene, C. "The anti-gene strategy: control of gene expression by triplex-forming-oligonucleotides". *Anticancer Drug Des.* 6(6): 569–84, 1991. Review.

144. Helene, C. and Thuong, N. T. "Design of bifunctional oligonucleotide intercalator conjugates as inhibitors of gene expression". *Nucleic Acids Symp Ser.* 1991(24): 133–7, 1991.

145. Sun, J. S., et al. "Triple-helix formation by alpha oligodeoxynucleotides and alpha oligodeoxynucleotide-intercalator conjugates" *Proc Natl Acad Sci U S A.* 88: 6023–7, 1991.

146. Pilch, D. S., et al. "Characterization of a triple helix-specific ligand. BePI (3-methoxy-7H-8-methyl-11-[(3,-amino)propylamino]-benzo[e] pyrido[4,3-b] indole) intercalates into both double-helical and triple-helical DNA". *J Mol Biol.* 232(3): 926–46, 1993.

147. Wilson, W. D., et al. "DNA triple-helix specific intercalators as antigene enhancers: unfused aromatic cations". *Biochemistry.* 32(40): 10614–21, 1993.

148. Mouscadet, J. F., et al. "Triple helix formation with short oligonucleotide-intercalator conjugates matching the HIV-1 U3 LTR end sequence". *Biochemistry.* 33(14): 4187–96, 1994.

149. Le Doan, T., et al. *Nucleic Acids Res.* 15: 7749, 1987.

150. Praseuth, D., et al. *Proc Natl. Acad. Sci. USA.* 85: 1349, 1988.

151. Vlassov, V. V., et al. *Gene.* 72: 313, 1988.

152. Fedorova, O. S., et al. *FEBS Lett.* 228: 273, 1988.

153. Greenfield, L., Bloch, W., and Moreland, M. "Thiol-containing cross-linking agent with enhanced steric hindrance". *Bioconjug Chem.* 1(6): 400–10, 1990.

154. Perrouault, L., et al. "Sequence-specific artificial photo-induced endonucleases based on triple helix-forming oligonucleotides". *Nature.* 344(6264): 358–60, 1990.

155. Jackson, C., et al. "N2,N4,N6-tri(hydroxymethyl)-N2,N4,N6-trimethylmelamine (trimelamol) is an efficient DNA cross-linking agent in vitro". *Biochem Pharmacol.* 42(11): 2091–7, 1991.

156. Le Doan, T., et al. "Recognition and photo-induced cleavage and cross-linking of nucleic acids by oligonucleotides covalently linked to ellipticine". *Antisense Res Dev.* 1(1): 43–54, 1991.

157. Giovannangeli, C., Thuong, N. T., and Helene, C. "Oligodeoxynucleotide-directed photo-induced cross-linking of HIV proviral DNA via triple-helix formation". *Nucleic Acids Res.* 20(16): 4275–81, 1992.

158. Miller, P. S. "Preparation of psoralen-derivatized oligodeoxyribonucleoside methylphosphonates". *Methods Enzymol.* 211(54): 54–64, 1992. Review.

159. Havre, P. A., et al. "Targeted mutagenesis of DNA using triple helix-forming oligonucleotides linked to psoralen". *Proc Natl Acad Sci U S A.* 90(16): 7879–83, 1993.

160. Rajagopalan, K., et al. "Synthesis and application of bidentate photoaffinity cross-linking reagents. Nucleotide photoaffinity probes with two photoactive groups". *J Biol Chem.* 268(19): 14230–8, 1993.

161. Boutorine, A. S., et al. "Rapid routes of synthesis of chemically reactive and highly radioactively labeled alpha- and beta-oligonucleotide derivatives for in vivo studies". *Bioconjug Chem.* 1(5): 350–6, 1990.

162. Farquharson, M., Harvie, R., and McNicol, A. M. "Detection of messenger RNA using a digoxigenin end labelled oligodeoxynucleotide probe". *J Clin Pathol.* 43(5): 424–8, 1990.

163. Haralambidis, J., et al. "The preparation of polyamide-oligonucleotide probes containing multiple non-radioactive labels". *Nucleic Acids Res.* 18(3): 501–5, 1990.

164. Strobel, O. K., et al. "Preparation and characterization of spin-labeled oligonucleotides for DNA hybridization". *Bioconjug Chem.* 2(2): 89–95, 1991.

165. Nelson, P. S., Kent, M., and Muthini, S. "Oligonucleotide labeling methods. 3. Direct labeling of oligonucleotides employing a novel, non-nucleosidic, 2-aminobutyl-1, 3-propanediol backbone". *Nucleic Acids Res.* 20(23): 6253–9, 1992.

166. Durrant, I. and Chadwick, P. M. "Hybridization of fluorescein-labeled oligonucleotide probes and enhanced chemiluminescence detection". *Methods Mol Biol.* 28(141): 141–8, 1994. Review.

167. Brossalina, E., Demchenko, E., and Vlassov, V. "Sequence specific alkylation of dsDNA by 2-chloroethylamine derivatives of purine oligonucleotides". *Nucleic Acids Symp Ser.* 1991(24): 262, 1991.

168. Brossalina, E. B., et al. "Sequence-specific alkylation of dsDNA with derivatives of pyrimidine oligonucleotides conjugated to 2-chloroethylamine groups". *Antisense Res Dev.* 1(3): 229–42, 1991.

169. Gourdie, T. A., et al. "Synthesis and evaluation of DNA-targeted spatially separated bis(aniline mustards) as potential alkylating agents with enhanced DNA cross-linking capability". *J Med Chem.* 34(1): 240–8, 1991.

170. Gravatt, G. L., et al. "DNA-directed alkylating agents. 4.4-anilinoquinoline-based minor groove directed aniline mustards". *J Med Chem.* 34(5): 1552–60, 1991.

171. Prakash, A. S., et al. "Synthesis and anti-tumour activity of the spatially-separated mustard bis-N,N'-[3-(N-(2-chloroethyl)-N-ethyl)amino-5-[N,N-dimethyla mino) methy 1)-aminophenyl]-1,4-benzenedicarboxamide, which alkylates DNA exclusively at adenines in the minor groove". *Anticancer Drug Des.* 6(3): 195–206, 1991.

172. Zarytova, V. F., et al. "[Sequence-specific modification of nucleic acids by oligonucleotide derivative containing alkylating groups in the C-5-position of deoxyuridine]". *Bioorg Khim.* 18(5): 640–5, 1992.

173. Berger, N. A. "Alkylating agents". *Cancer Chemother Biol Response Modif.* 14(26): 26–36, 1993. Review.

174. Lee, M., et al. "Design, synthesis, and biological evaluation of DNA sequence and minor groove selective alkylating agents". *Anticancer Drug Des.* 8(3): 173–92, 1993.

175. Yamamoto, K., Sugiyama, H., and Kawanishi, S. "Concerted DNA recognition and novel site-specific alkylation by duocarmycin A with distamycin A". *Biochemistry.* 32(4): 1059–66, 1993.

176. Zhang, Y., et al. "Groove- and sequence-selective alkylation of DNA by sulfonate esters tethered to lexitropsins". *Biochemistry.* 32(31): 7954–65, 1993.

177. Lee, M., et al. "In vitro photoinduced cytotoxicity and DNA binding properties of psoralen and coumarin conjugates of netropsin analogues: DNA sequence-directed alkylation and cross-link formation". *J Med Chem.* 37(8): 1208–13, 1994.

178. Le Doan, T., et al. *Bioconjugate Chem.* 1: 108, 1990.

179. Bhan, P. and Miller, P. S. "Photo-cross-linking of psoralen-derivatized oligonucleoside methylphosphonates to single-stranded DNA". *Bioconjug Chem.* 1(1): 82–8, 1990.

180. Chatterjee, M. and Rokita, S. E. *J. Am. Chem. Soc.* 112: 9387, 1990.

181. Celander, D. W. and Cech, T. R. "Iron(II)-ethylenediaminetetraacetic acid catalyzed cleavage of RNA and DNA oligonucleotides: similar reactivity toward single- and double-stranded forms". *Biochemistry.* 29(6): 1355–61, 1990.

182. Sigman, D. S. and Chen, C. H. "Chemical nucleases: new reagents in molecular biology". *Annu Rev Biochem.* 59(207): 207–36, 1990. Review.

183. Nagai, K. and Hecht, S. M. "Site-specific DNA cleavage by antisense oligonucleotides covalently linked to phenazine di-N-oxide". *J Biol Chem.* 266(35): 23994–4002, 1991.

184. Jayasena, S. D. and Johnston, B. H. "Site-specific cleavage of the transactivation response site of human immunodeficiency virus RNA with a tat-based chemical nuclease". *Proc Natl Acad Sci U S A.* 89(8): 3526–30, 1992.

185. Podhajska, A. J., Kim, S. C., and Szybalski, W. "Conferring new specificities on restriction enzymes: cleavage at any predetermined site by combining adapter oligodeoxynucleotide and class-IIS enzyme". *Methods Enzymol.* 216 (303): 303–9, 1992.

186. Casas, C., Lacey, C. J., and Meunier, B. "Preparation of hybrid "DNA cleaver-oligonucleotide" molecules based on a metallotris(methylpyridiniumyl)porphyrin motif". *Bioconjug Chem.* 4(5): 366–71, 1993.

187. Chen, C. B., Gorin, M. B., and Sigman, D. S. "Sequence-specific scission of DNA by the chemical nuclease activity of 1,10-phenanthroline-copper(I) targeted by RNA". *Proc Natl Acad Sci U S A.* 90(9): 4206–10, 1993.

188. Huber, P. W. "Chemical nucleases: their use in studying RNA structure and RNA-protein interactions". *Faseb J.* 7(14): 1367–75, 1993. Review.

189. Kappen, L. S. and Goldberg, I. H. "DNA conformation-induced activation of an enediyne for site-specific cleavage". *Science.* 261(5126): 1319–21, 1993.

190. Sigman, D. S., Chen, C. H., and Gorin, M. B. "Sequence-specific scission of DNA by RNAs linked to a chemical nuclease". *Nature.* 363(6428): 474–5, 1993.

191. Zarytova, V. F., Sergeyev, D. S., and Godovikova, T. S. "Synthesis of bleomycin A5 oligonucleotide derivatives and site-specific cleavage of the DNA target". *Bioconjug Chem.* 4(3): 189–93, 1993.

192. Shimizu, M., Inoue, H., and Ohtsuka, E. "Detailed study of sequence-specific DNA cleavage of triplex-forming oligonucleotides linked to 1,10-phenanthroline". *Biochemistry.* 33(2): 606–13, 1994.

193. Froncois, et al. *Proc. Natl. Acad. Sci. USA.* 86: 9702, 1989.

194. Froncois, et al. *J. Biol. Chem.* 264: 5891, 1989.

195. Le Doan, T., et al. *Nucleic Acids Res.* 15: 8643, 1987.

196. Corey, D. R. and Schultz, P. G. *Science.* 238: 1401, 1987.

197. Zuckermann, R. N., Corey, D. R., and Schultz, P. G. *J. Am. Chem. Soc.* 110: 1614, 1988.

198. Pei, D., Corey, D. R., and Schultz, P. G. "Site-specific cleavage of duplex DNA by a semisynthetic nuclease via triple-helix formation". *Proc Natl Acad Sci U S A.* 87(24): 9858–62, 1990.

199. Haseloff, J. and Gerlach, W. L. *Nature.* 334: 585, 1988.

200. Jeffries, A. C. and Symons, R. H. *Nucleic Acids Res.* 17: 1371, 1989.

201. Van, A. R. and Hecht, S. M. "A ribozyme model: site-specific cleavage of an RNA substrate by Mn2+". *Adv Inorg Biochem.* 9(1): 1–40, 1994. Review.

202. Puglisi, J. D. and Tinoco, I. J. "Absorbance melting curves of RNA". *Methods Enzymol.* 180(304): 304–25, 1989. Review.

203. Jaeger, J. A., SantaLucia, J. J., and Tinoco, I. J. "Determination of RNA structure and thermodynamics". *Annu Rev Biochem.* 62(255): 255–87, 1993. Review.

204. Breslauer, K. J. "Extracting thermodynamic data from equilibrium melting curves for oligonucleotide order-disorder transitions". *Methods Mol Biol.* 26(347): 347–72, 1994. Review.

205. Nielsen, P. E. "Chemical and photochemical probing of DNA complexes". *J Mol Recognit.* 3(1): 1–25, 1990. Review.

206. Zhong, W. X., et al. "DNA solution conformation via infrared circular dichroism: experimental and theoretical results for B-family polymers". *Biochemistry.* 29(32): 7485–91, 1990.

207. Gray, D. M., Ratliff, R. L., and Vaughan, M. R. "Circular dichroism spectroscopy of DNA". *Methods Enzymol.* 211(389): 389–406, 1992. Review.

208. Lilley, D. M., Bhattacharyya, A., and McAteer, S. "Gel electrophoresis and the structure of RNA molecules". *Biotechnol Genet Eng Rev.* 10(379): 379–401, 1992. Review.

209. Ussery, D. W., Hoepfner, R. W., and Sinden, R. R. "Probing DNA structure with psoralen in vitro". *Methods Enzymol.* 212(242): 242–62, 1992. Review.

210. Freedman, T. B. and Nafie, L. A. "Infrared circular dichroism". *Methods Enzymol.* 226(306): 306–19, 1993. Review.

211. Jones, C. "Applications of nuclear magnetic resonance, circular dichroism and fluorescence spectroscopy to the characterization of biological products". *Biologicals.* 21(2): 119–24, 1993.

212. Sylvers, L. A. and Wower, J. "Nucleic acid-incorporated azidonucleotides: probes for studying the interaction of RNA or DNA with proteins and other nucleic acids". *Bioconjug Chem.* 4(6): 411–8, 1993.

213. Thomson, A. J., Cheesman, M. R., and George, S. J. "Variable-temperature magnetic circular dichroism". *Methods Enzymol.* 226(199): 199–232, 1993. Review.

214. Galas, D. J. and Schmitz, A. "Footprinting". *Nucleic Acids Res.* 5: 3157, 1978.

215. Tullius, T. D., et al. "Hydroxy Radical Footprinting: A High Resolution Method for Mapping Protein-DNA Contacts." Recombinant DNA (Part F). Wu ed. 1987 Academic Press Inc. New York, N.Y.

216. Dixon, W. J., et al. "Hydroxyl radical footprinting". *Methods Enzymol.* 208(380): 380–413, 1991. Review.

217. Tullius, T. D. "DNA footprinting with the hydroxyl radical". *Free Radic Res Commun.* 2(521): 521–9, 1991. Review.

218. Hayes, J. J., Kam, L., and Tullius, T. D. "Footprinting Protein-DNA Complexes with Gamma-rays." Oxygen Radicals in Biological Systems (Part B: Oxygen Radicals and Antioxidants. WU ed. 1990 Academic Press Inc. New York, N.Y.

219. Duval, V. G., Thuong, N. T., and Helene, C. "Specific inhibition of transcription by triple helix-forming oligonucleotides". *Proc Natl Acad Sci U S A.* 89(2): 504–8, 1992.

220. Metzger, W., et al. "Hydroxyl radical footprint analysis of human immunodeficiency virus reverse transcriptase-template.primer complexes". *Proc Natl Acad Sci U S A.* 90(13): 5909–13, 1993.

221. Mah, S. C., Townsend, C. A., and Tullius, T. D. "Hydroxyl radical footprinting of calicheamicin. Relationship of DNA binding to cleavage". *Biochemistry.* 33(2): 614–21, 1994.

222. "NACB 13th annual symposium: diagnostic applications of nucleic acid probes in the clinical laboratory. Toronto, Canada, Jun. 2–3, 1989. Proceedings". *Clin Biochem.* 23(4): 253–340, 1990. Review.

223. Barker, R. J. "DNA probe diagnosis of parasitic infections". *Exp Parasitol.* 70(4): 494–9, 1990.

224. Gillespie, D. "The magic and challenge of DNA probes as diagnostic reagents". *Vet Microbiol.* 24(3–4): 217–33, 1990. Review.

225. Kohne, D. E. "The use of DNA probes to detect and identify microorganisms". *Adv Exp Med Biol.* 263(11): 11–35, 1990. Review.

226. Char, S. and Farthing, M. J. "DNA probes for diagnosis of intestinal infection". *Gut.* 32(1): 1–3, 1991.

227. Pfaller, M. A. "Diagnostic applications of DNA probes". *Infect Control Hosp Epidemiol.* 12(2): 103–10, 1991. Review.

228. Peters, C., et al. "Individual-specific DNA fingerprinting in man using the oligonucleotide probe (GTG) 5/(CAC) 5". *Eur J Clin Chem Clin Biochem.* 29(5): 321–5, 1991.

229. Wetmur, J. G. "DNA probes: applications of the principles of nucleic acid hybridization". *Crit Rev Biochem Mol Biol.* 26(3–4): 227–59, 1991. Review.

230. Narayanan, S. "Overview of principles and current uses of DNA probes in clinical and laboratory medicine". *Ann Clin Lab Sci.* 22(6): 353–76, 1992. Review.

231. Rotbart, H. A. "DNA probes for viral diagnosis". *Adv Exp Med Biol.* 312(201): 201–9, 1992. Review.

232. Krawczak, M., et al. "Paternity testing with oligonucleotide multilocus probe (CAC) 5/(GTG)5: a multicenter study". *Forensic Sci Int.* 59(2): 101–17, 1993.

233. Utz, E. D., et al. "Detection of human tRNAs with antisense oligonucleotides". *Anal Biochem.* 216(1): 110–7, 1994.

234. Agrawal, S. and Zamecnik, P. C. "Site specific functionalization of oligonucleotides for attaching two different reporter groups". *Nucleic Acids Res.* 18(18): 5419–23, 1990.

235. Misiura, K., et al. "Biotinyl and phosphotyrosinyl phosphoramidite derivatives useful in the incorporation of multiple reporter groups on synthetic oligonucleotides". *Nucleic Acids Res.* 18(15): 4345–54, 1990.

236. Tang, J. Y. and Agrawal, S. "Incorporation of multiple reporter groups on synthetic oligonucleotides". *Nucleic Acids Res.* 18(21): 6461, 1990.

237. Dirks, R. W., et al. "3'-end fluorochromized and haptenized oligonucleotides as in situ hybridization probes for multiple, simultaneous RNA detection". *Exp Cell Res.* 194 (2): 310–5, 1991.

238. Murakami, A., et al. "Fluorescent-labeled oligonucleotide probes: detection of hybrid formation in solution by fluorescence polarization spectroscopy". *Nucleic Acids Res.* 19(15): 4097–102, 1991.

239. Will, D. W., Pritchard, C. E., and Brown, T. "The synthesis of oligonucleotides that contain 2,4-dinitrophenyl reporter groups". *Carbohydr Res.* 216(315): 315–22, 1991.

240. Grzybowski, J., et al. "Synthesis and antibody-mediated detection of oligonucleotides containing multiple 2,4-dinitrophenyl reporter groups". *Nucleic Acids Res.* 21(8): 1705–12, 1993.

241. Agrawal, S. "Functionalization of oligonucleotides with amino groups and attachment of amino specific reporter groups". *Methods Mol Biol.* 26(93): 93–120, 1994. Review.

242. Fidanza, J. A., Ozaki, H., and McLaughlin, L. W. "Functionalization of oligonucleotides by the incorporation of thio-specific reporter groups". *Methods Mol Biol.* 26(121): 121–43, 1994. Review.

243. Balaguer, P., et al. "Detection of single base substitutions in polynucleotides by capture with immobilized oligonucleotides". *Mol Cell Probes.* 7(2): 155–9, 1993.

244. Kawasaki, E., Saiki, R., and Erlich, H. "Genetic analysis using polymerase chain reaction-amplified DNA and immobilized oligonucleotide probes: reverse dot-blot typing". *Methods Enzymol.* 218(369): 369–81, 1993. Review.

245. Kawasaki, E. S. and Chehab, F. F. "Analysis of gene sequences by hybridization of PCR-amplified DNA to covalently bound oligonucleotide probes. The reverse dot blot method". *Methods Mol Biol.* 28(225): 225–36, 1994. Review.

246. Boiziau, C., et al. "Ribonuclease H-mediated inhibition of translation and reverse transcription by antisense oligodeoxynucleotides". *Biochem Soc Trans.* 20(4): 764–7, 1992.

247. Calabretta, B., et al. "Prospects for gene-directed therapy with antisense oligodeoxynucleotides". *Cancer Treat Rev.* 19(2): 169–79, 1993. Review.

248. Cumin, F., et al. "Modulation of human prorenin gene expression by antisense oligonucleotides in transfected CHO cells". *Eur J Biochem.* 212(2): 347–54, 1993.

249. Nagel, K. M., Holstad, S. G., and Isenberg, K. E. "Oligonucleotide pharmacotherapy: an antigene strategy". *Pharmacotherapy.* 13(3): 177–88, 1993. Review.

250. Schreier, H. "The new frontier: gene and oligonucleotide therapy". *Pharm Acta Helv.* 68(3): 145–59, 1994. Review.

251. Inoue, M. *Gene.* 72: 25, 1988.

252. Winkler, M. E., et al. *Proc. Natl. Acad. Sci. USA.* 79: 2181, 1982.

253. Crooke, R. M. "In vitro toxicology and pharmacokinetics of antisense oligonucleotides". *Anticancer Drug Des.* 6(6): 609–46, 1991. Review.

254. Mirabelli, C. K., et al. "In vitro and in vivo pharmacologic activities of antisense oligonucleotides". *Anticancer Drug Des.* 6(6): 647–61, 1991.

255. Whitesell, L., Rosolen, A., and Neckers, L. M. "In vivo modulation of N-myc expression by continuous perfusion with an antisense oligonucleotide". *Antisense Res Dev.* 1(4): 343–50, 1991.

256. Bordier, B., et al. "In vitro effect of antisense oligonucleotides on human immunodeficiency virus type 1 reverse transcription". *Nucleic Acids Res.* 20(22): 5999–6006, 1992.

257. Hanvey, J. C., et al. "Antisense and antigene properties of peptide nucleic acids". *Science.* 258(5087): 1481–5, 1992.

258. Lisziewicz, J., et al. "Specific inhibition of human immunodeficiency virus type 1 replication by antisense oligonucleotides: an in vitro model for treatment". *Proc Natl Acad Sci U S A.* 89(23): 11209–13, 1992.

259. Woolf, T. M., Melton, D. A., and Jennings, C. G. "Specificity of antisense oligonucleotides in vivo". *Proc Natl Acad Sci U S A.* 89(16): 7305–9, 1992.

260. Wu, G. Y. and Wu, C. H. "Specific inhibition of hepatitis B viral gene expression in vitro by targeted antisense oligonucleotides". *J Biol Chem.* 267(18): 12436–9, 1992.

261. Nielsen, P. E., et al. "Peptide nucleic acids (PNAs): potential antisense and anti-gene agents". *Anticancer Drug Des.* 8(1): 53–63, 1993.

262. offensperger, W. B., et al. "In vivo inhibition of duck hepatitis B virus replication and gene expression by phosphorothioate modified antisense oligodeoxynucleotides". *Embo J.* 12(3): 1257–62, 1993.

263. Praseuth, D., et al. "Unexpected effect of an anti-human immunodeficiency virus intermolecular triplex-forming oligonucleotide in an in vitro transcription system due to RNase H-induced cleavage of the RNA transcript". *Antisense Res Dev.* 3(1): 33–44, 1993.

264. Volkmann, S., Dannull, J., and Moelling, K. "The polypurine tract, PPT, of HIV as target for antisense and triple-helix-forming oligonucleotides". *Biochimie.* 75(1–2): 71–8, 1993.

265. Bennett, C. F., et al. "Inhibition of endothelial cell adhesion molecule expression with antisense oligonucleotides". *J Immunol.* 152(7): 3530–40, 1994.

266. Alama, A., et al. "The use of antisense oligodeoxynucleotides (aODNs) for the therapy of cancer". *Drugs Exp Clin Res.* 17(12): 575–9, 1991.

267. Cohen, J. S. "Antisense oligodeoxynucleotides as antiviral agents". *Antiviral Res.* 16(2): 121–33, 1991. Review.

268. Agrawal, S. "Antisense Oligonucleotides as Antiviral Agents". *TIBTECH.* 10: 152–158, 1992. Review.

269. Coulson, J. and Malcolm, A. D. "Antisense oligonucleotides as antiviral agents". *Ann N Y Acad Sci.* 660(339): 339–41, 1992.

270. Cantin, E. M. and Woolf, T. M. "Antisense oligonucleotides as antiviral agents: prospects and problems". *Trends Microbiol.* 1(7): 270–6, 1993. Review.

271. Kabanov, A. V., et al. *FEBS Lett.* 259: 327, 1990.

272. Shea, R. G., Masters, J. C., and Bischofberger, N. *Nucleic Acids Res.* 18: 3777, 1990.

273. Boutorin, A., et al. "Synthesis of Alkylating Oligonucleotide Derivatives Containing Cholesterol or Pheneze-niumresidues at 3'-terminusand Their Interaction with mammalian Cells". *FEBS Lett.* 254: 129, 1989.

274. Oberhauser, B. and Wagner, E. "Effective Incorporation of 2'-O-methyl oligoribonucleotides into Liposomes and Enhanced Cell Association through Modfication with Thio-cholesterol". *Nucleic Acids Res.* 20: 533, 1992.

275. SGI. IRIS Work-Station. Silicon Graphics Inc., Mountain View, Calif.

276. SYBYL. SYBYF Molecular Modelling Package. V 5.4/6.0, 1992, TRIPOS Associates Inc., St. Louis, Missouri 63144–2913.

277. Arnott, S. and Hukins, D. W. L. "Crystal-structure of ds-DNA". *Biochem. Biophys. Res. Commun.* 47: 1504, 1972.

278. March, J. "Advanced Organic Chemistry: Reactions, Mechanisms and Structure." 1992 John Wiley & Sons. New York, N.Y.

279. Larock, R. C. "Comprehensive Organic Transformations: A Guide to Functional Group Preparations." 1989 VCH Publishers, Inc. New York.

280. Hooz, J. and Gilani, S. S. H. "A Rapid, Mild Procedure for the Preparation of Alkyl Chlorides and Bromides". *Canadian J. Chem.* 46: 86–87, 1968.

281. Bajgrowicz, J. A., et al. "Organocuperates Mediated Carbon-Carbon Bond Formation in gamma position of alpha-amino esters without racemization". *Tetrahedron Lett.* 25: 2231–2234, 1984.

282. Jost, K. and Rudinger, J. "Amino Acids and Peptides. LXXIV.: Derivatives of L-Cystathione suitable for Peptide Synthesis". *Coll. Czech. Chem. Commun.* 32: 2485–2490, 1967.

283. Natelson, S. and Natelson, E. A. "Preparation of D-, DL-, and L-Homoserine Lactone from Methionine". *Microchemical Journal.* 40: 226–232, 1989.

284. Valerio, R. M., Alewood, P. F., and Johns, R. B. "Synthesis of Optically Active 2-(tert-Butyloxycarbonylamino)-4-dialkoxyphosphoryl-butanoate Protected Isosteres of O-phosphonoserine for Peptide Synthesis". *Synthesis. :* 786–789, 1988.

285. Carpino, L. A. "1-Hydroxy-7-azabenzotriazole. An efficient Peptide Coupling Additive". *J. Am. Chem. Soc.* 115: 4397–98, 1993.

We claim:

1. A composition useful in targeting a nucleic acid comprising a stereochemically-selected population of peptide-based nucleic acid mimics (PENAMs) each member of which comprises a sequence of at least about 4 NuAA monomers, wherein said NuAA monomers are each of the following formula:

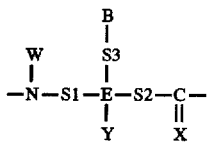

wherein:

E is carbon (C) or nitrogen (N);

W is hydrogen or a spacer group;

Y is hydrogen or a spacer group (when E is carbon), or Y is a lone pair of electrons (when E is nitrogen);

S1 is a bond or a first spacer group;

S2 is a bond or a second spacer group;

S3 is a bond or a third spacer group;

X is oxygen (O) or sulfur (S);

B is a base segment comprising a nucleotidic base or an analog thereof; and

N is nitrogen, and wherein at least one of said PENAMs is a homomorphicaily-preferred PENAM comprising a D-chiral center and wherein said homomorphically-preferred PENAM makes up at least about 10% of the stereochemically-selected population of PENAMs wherein said D-chiral center is located within a NuAA at position E wherein E is carbon.

2. A PENAM composition of claim 1, wherein the NuAA monomers in said homomorphically-preferred PENAM are joined directly to each other via peptide bonds and at least one of S1 and S2 in each of the adjacent NuAA monomers is a spacer group.

3. A PENAM composition of claim 1, wherein the NuAA monomers in said homomorphically-preferred PENAM are joined via intervening aminoacyl residues and S2 in each of the NuAA monomers is a bond.

4. A PENAM composition of claim 1, wherein said D-chiral center is located between two NuAA monomers at a chiral carbon in an intervening amino acid residue.

5. A PENAM composition of claim 1, wherein at least about 50% of the chiral centers in said homomorphically-preferred PENAM are D-chiral centers.

6. A PENAM composition of claim 1, wherein about 50% of the chiral centers in said homomorphically-preferred PENAM are D-chiral centers, and 50% of the chiral centers are L-chiral centers, and wherein at least about 80% of L-chiral centers are flanked by D-chiral centers.

7. A PENAM composition of claim 1, wherein at least about 80% of the chiral centers in said homomorphically-preferred PENAM are D-chiral centers.

8. A PENAM composition of claim 1, wherein at least one of S1 and S2 is a spacer group having a backbone of two to three atoms, S3 is a spacer group having a backbone of two to three atoms, W is hydrogen, E is carbon, and Y is hydrogen.

9. A PENAM composition of claim 1, wherein said homomorphically-preferred PENAM comprises a quasi-chiral center and said quasi-chiral center is located within a NuAA monomer at position E wherein E is nitrogen.

10. A PENAM composition of claim 1, wherein said homomorphically-preferred PENAM comprises a quasi-chiral center and said quasi-chiral center is located between two NuAA monomers in an intervening aza-amino acid residue.

11. A PENAM composition of claim 1, wherein said homomorphically-preferred PENAM further comprises a target modifying group.

12. A PENAM composition of claim 11, wherein said target modifying group is located within a NuAA monomer.

13. A PENAM composition of claim 11, wherein said target modifying group is located between NuAA monomers or outside of a string of NuAA monomers.

14. A free NuAA monomer that is a precursor of a NuAA monomeric subunit comprising a D-chiral center wherein said NuAA monomeric subunit comprising a D-chiral center is of the following formula:

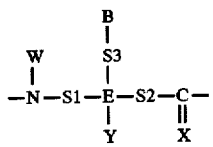

wherein:
E is said D-chiral center and is carbon (C);
W is hydrogen or a spacer group;
Y is hydrogen or a spacer group;
S1 is a bond or a first spacer group;
S2 is a bond or a second spacer group;
S3 is a third spacer group with a backbone of at least two atoms;
X is oxygen (O) or sulfur (S);
B is a base segment comprising a nucleotidic base or an analog thereof; and
N is nitrogen;
and wherein at least one of S1 and S2 is a spacer group, and wherein S3 is a spacer group with a backbone of at least two atoms;
wherein said free NuAA monomer is of the same formula except that the N-terminus is in the form of an amine group or a protected amine group and the C-terminus is in the form of a carboxyl group or a protected carboxyl group.

15. A method of preparing a PENAM composition of claim 1 for targeting a target nucleic acid comprising:
(a) providing at least about 4 NuAA monomers wherein at least one of said NuAA monomers comprises a D-chiral center at portion E wherein E is carbon; and
(b) synthesizing an oligomer of the monomers such that the arrangement of bases in the oligomer is substantially complementary to a sequence of nucleotidic bases in a portion of the target nucleic acid.

16. A method of claim 15, wherein said NuAA monomers are linked to each other directly via peptide bonds.

17. A method of claim 15, wherein said NuAA monomers are linked to each other indirectly via intervening aminoacyl monomers.

18. A method of claim 15, further comprising the step of synthesizing a NuAA monomer having a D-chiral center at position E wherein E is carbon wherein said NuAA monomer having a D-chiral center at position E wherein E is carbon is present at a purity of at least about 90% enantiomeric excess relative to its enantiomeric NuAA monomer having an L-chiral center.

19. A method of claim 15, further comprising the step of synthesizing a NuAA monomer having a quasi-chiral center.

20. A method of targeting a target nucleic acid comprising:
(a) providing a PENAM composition according to claim 1; and
(b) contacting said PENAM composition with the target nucleic acid.

21. A method of modulating a target nucleic acid in an antisense manner comprising:
(a) providing a PENAM composition according to claim 1 wherein the sequence of bases in said NuAA monomers is substantially complementary to a sequence of bases in the target nucleic acid; and
(b) contacting said PENAM composition with the target nucleic acid.

22. A method of modifying a target nucleic acid comprising:
(a) providing a PENAM composition of claim 1 wherein said homomorphically-preferred PENAM further comprises a target modifying group; and
(b) contacting said PENAM composition with the target nucleic acid.

23. A method of detecting a target nucleic acid comprising:
(a) providing a PENAM composition according to claim 1 wherein the sequence of bases in said NuAA monomers is substantially complementary to a sequence of bases in the target nucleic acid; and
(b) contacting said PENAM composition with the target nucleic acid; and
(c) detecting a target complex comprising said nucleic acid mimic and said target nucleic acid or detecting a modification in the target nucleic acid.

24. A method of isolating a target nucleic acid comprising:
(a) providing a PENAM composition according to claim 1 wherein the sequence of bases in said NuAA monomers is substantially complementary to a sequence of bases in the target nucleic acid; and
(b) contacting said PENAM composition with the target nucleic acid; and
(c) isolating PENAMs bound to said target nucleic acid or isolating a modified target nucleic acid.

* * * * *